US008293786B2

(12) United States Patent
Stinchcomb et al.

(10) Patent No.: US 8,293,786 B2
(45) Date of Patent: Oct. 23, 2012

(54) PRODRUGS OF CANNABIDIOL, COMPOSITIONS COMPRISING PRODRUGS OF CANNABIDIOL AND METHODS OF USING THE SAME

(75) Inventors: Audra Lynn Stinchcomb, Lexington, KY (US); Miroslaw Jerzy Golinski, Lexington, KY (US); Dana Carmel Hammell, Georgetown, KY (US); Jeffrey Lynn Howard, Richmond, KY (US); Stan Lee Banks, Frankfort, KY (US)

(73) Assignee: Alltranz Inc., Lexington, KY (US)

( * ) Notice: Subject to any disclaimer, the term of this patent is extended or adjusted under 35 U.S.C. 154(b) by 779 days.

(21) Appl. No.: 12/182,974

(22) Filed: Jul. 30, 2008

(65) Prior Publication Data
US 2009/0036523 A1 Feb. 5, 2009

Related U.S. Application Data

(60) Provisional application No. 60/952,746, filed on Jul. 30, 2007.

(51) Int. Cl.
A61K 31/27 (2006.01)
A61K 31/265 (2006.01)
A61K 31/22 (2006.01)
C07C 271/08 (2006.01)
C07C 69/66 (2006.01)

(52) U.S. Cl. ........ 514/483; 514/512; 514/551; 560/158; 560/159; 560/163; 560/179

(58) Field of Classification Search ............... None
See application file for complete search history.

(56) References Cited

U.S. PATENT DOCUMENTS

| | | | |
|---|---|---|---|
| 3,968,125 A | 7/1976 | Archer | |
| 4,206,225 A | 6/1980 | Johnson | |
| 4,232,018 A | 11/1980 | Johnson | |
| 4,235,913 A | 11/1980 | Johnson et al. | |
| 4,243,674 A | 1/1981 | Bindra | |
| 4,260,764 A | 4/1981 | Johnson | |
| 4,263,438 A | 4/1981 | Althuis et al. | |
| 4,270,005 A | 5/1981 | Althuis et al. | |
| 4,283,569 A | 8/1981 | Althuis et al. | |
| 4,371,720 A | 2/1983 | Johnson et al. | |
| 4,663,474 A | 5/1987 | Urban | |
| 4,876,276 A | 10/1989 | Mechoulam et al. | |
| 5,223,262 A | 6/1993 | Kim et al. | |
| 5,254,346 A | 10/1993 | Tucker et al. | |
| 5,310,561 A | 5/1994 | Jao et al. | |
| 5,521,215 A | 5/1996 | Mechoulam et al. | |
| 5,624,941 A | 4/1997 | Barth et al. | |
| 5,716,928 A | 2/1998 | Benet et al. | |
| 5,804,592 A | 9/1998 | Volicer | |
| 5,847,128 A | 12/1998 | Martin et al. | |
| 5,925,768 A | 7/1999 | Barth et al. | |
| 6,017,919 A | 1/2000 | Inaba et al. | |
| 6,028,084 A | 2/2000 | Barth et al. | |
| 6,100,259 A | 8/2000 | Xiang et al. | |
| 6,113,940 A | 9/2000 | Brooke et al. | |
| 6,132,762 A | 10/2000 | Cristobal | |
| 6,162,829 A | 12/2000 | Burstein | |
| 6,284,788 B1 | 9/2001 | Mittendorf et al. | |
| 6,328,992 B1 | 12/2001 | Brooke et al. | |
| 6,344,474 B1 | 2/2002 | Maruani et al. | |
| 6,503,532 B1 | 1/2003 | Murty et al. | |
| 6,509,352 B1 | 1/2003 | Inaba et al. | |
| 6,566,560 B2 * | 5/2003 | Travis | 568/715 |
| 2002/0111377 A1 | 8/2002 | Stinchcomb | |
| 2003/0166727 A1 | 9/2003 | Mechoulam et al. | |
| 2005/0266061 A1 | 12/2005 | Stinchcomb et al. | |

FOREIGN PATENT DOCUMENTS

| | | |
|---|---|---|
| EP | 0570920 A1 | 11/1993 |
| EP | 0670826 B1 | 9/1995 |
| EP | 0799188 B1 | 9/1999 |
| GB | 2439393 A | 12/2007 |
| JP | 11080124 A | 3/1999 |
| WO | 89/07959 A1 | 9/1989 |
| WO | 98/31227 A1 | 7/1998 |
| WO | 98/41519 A1 | 9/1998 |
| WO | 99/24471 A1 | 5/1999 |
| WO | 99/53917 A1 | 10/1999 |
| WO | WO-99/53917 A | 10/1999 |
| WO | 00/16756 A2 | 3/2000 |
| WO | 00/32200 A1 | 6/2000 |
| WO | 2004/039317 A2 | 5/2004 |
| WO | WO-2004/039317 A | 5/2004 |
| WO | 2004/082620 A2 | 9/2004 |
| WO | WO-2004/082620 A | 9/2004 |
| WO | 2006/133941 A2 | 12/2006 |
| WO | WO-2006/133941 A | 12/2006 |
| WO | 2007/001891 A1 | 1/2007 |
| WO | 2008/107879 A1 | 9/2008 |
| WO | WO-2008/107879 A | 9/2008 |
| WO | 2009/018389 A1 | 2/2009 |

OTHER PUBLICATIONS

Morrow et al, The Open Drug Delivery Journal, Innovative Strategies for Enhancing Topical and Transdermal Drug Delivery, 2007, 1, pp. 36-59.*

Abu-Lafi, et al., "Role of Hydroxyl Groups in Chiral Recognition of Cannabinoids by Carmbamated Amylose", Journal of Chromatography, vol. 679, pp. 47-58 (1994); XP002505687.

Database CA [Online] Chemical Abstracts Service, Columbus, Ohio, US; Weiner, et al., "Monomers and Polymers of .DELTA.1(6)-Tetrahydrocannabinol and Cannabidiol", European Journal of Medicinal Chemistry, vol. 10(1), pp. 79-83 (1975); XP002505688 retrieved from STN Database accession No. 84:59754.

(Continued)

Primary Examiner — Paul A Zucker
(74) Attorney, Agent, or Firm — Foley & Lardner LLP

(57) ABSTRACT

Described herein are cannabidiol prodrugs, methods of making cannabidiol prodrugs, formulations comprising cannabidiol prodrugs and methods of using cannabidiols. One embodiment described herein relates to the transdermal or topical administration of a cannabidiol prodrug for treating and preventing diseases and/or disorders.

26 Claims, 8 Drawing Sheets

OTHER PUBLICATIONS

Database CA [Online] Chemical Abstracts Service, Columbus, Ohio, US; Handrick, et al., "Hashish 20. Synthesis of (.+-.)-.DELTA. 1- and .DELTA.6-3, 4-cis-cannabidiols and Their Isomerization by Acid Catalysis", Journal of Organic Chemistry, vol. 42(15), pp. 2563-2568. (1977); XP002505689 retrieved from STN Database accession No. 87:68497.

Database CA [Online] Chemical Abstracts Service, Columbus, Ohio, US; Knaus, et al., "The Separation, Identification, and Quantitation of Cannabinoids and Their T-Butyldimethylsilyl, Trimethylsilylacetate, and Diethylphosphate Derivatives Using High-Pressure Liquid Chromatography, Gas-Liquid Chromatography, and Mass Spectrometry", Journal of Chromatographic Science, vol. 14(11), pp. 525-30 (1976); XP002505690 retrieved from STN Database accession No. 86:38182.

Database CA [Online] Chemical Abstracts Service, Columbus, Ohio, US; Mechoulam, et al., "Hashish. IV. Isolation and Structure of Annabinolic, Cannabidiolic, and Cannabigerolic Acids", Tetrahedron, vol. 21(5), pp. 1223-1229 (1965); XP002505691 retrieved from STN Database accession No. 63:16677.

Database CA [Online] Chemical Abstracts Service, Columbus, Ohio, US; Petrzilka, et al., "Synthesis of Hashish Components. IV", Helvetica Chimica Acta, vol. 52(4), pp. 1102-1134 (1969); XP002505692 retrieved from STN Database accession No. 71:21989.

Database CA [Online] Chemical Abstracts Service, Columbus, Ohio, US; Madinaveitia, et al., "Cannabis Indica. XI. An Examination of the Alkali-Soluble Portion of American-Hemp Resin", Journal of the Chemical Society, pp. 628-630 (1942); XP002505693 retrieved from STN Database accession No. 37:3626.

Database CA [Online] Chemical Abstracts Service, Columbus, Ohio, US; Hattori, et al., "Gas Chromatography/Negative Ion Chemical Ionization Mass Spectrometry of Cannabinoids in Human Samples", Iyo Masu Kenkyukai Koenshu, vol. 8, pp. 159-160 (1983); XP002505694 retrieved from STN Database accession No. 100:97716.

Pillai, et al., "Physicochemical Evaluation, in Vitro Human Skin Diffusion, and Concurrent Biotransformation of 3-O-Alkyl Carbonate Prodrugs of Naltrexone", Pharmaceutical Research, vol. 21, No. 7, pp. 1146-1152 (2004); XP002469233 ISSN: 0724-8741.

Stinchcomb, et al., "Permeation of Buprenorphine and Its 3-Alkyl-Ester Prodrugs Through Human Skin", Pharmaceutical Research, vol. 13, No. 10, pp. 1519-1523 (1996); XP008016388 ISSN: 0724-8741.

International Search Report for PCT/US2008/071659, Dec. 12, 2008.

Written Opinion of the International Searching Authority for PCT/US2008/071659, Dec. 12, 2008.

Abu-Lafi, et al., "Role of hydroxyl groups in chiral recognition of cannabinoids by carbamated amylose," Journal of Chromatography A, 679: 47-58(1994).

Handrick, et al., "Hashish. 20. Synthesis of (+/-)-delta1- and delta 6-3,4-cis-cannabidiols and their isomerization by acid catalysis," Journal of Organic Chemistry, 42(15): 2563-8 (1977) [Chemical Abstract].

Hattori, et al., "Gas chromatography/negative ion chemical ionization mas spectrometry of cannabinoids in human samples," Iyo Masu Kenkyukai Koenshu, 8: 159-60 (1983) [Chemical Abstract].

Knaus, et al., "The separation, identification, and quantitation of cannabinoids and their t-butyldimethylsilyl, trimethylsilylacetate, and diethylphosphate derivatives using high-pressure liquid chromatography, gas-liquid chromatography, and mass spectrometry," Journal of Chromatography Science, 14(11): 525-30 (1976) [Chemical Abstract].

Madinaveitia et al., "Cannabis indicia. XI. An examination of the alkali-soluble portion of American-hemp resin." Journal of the Chemical Society, 628-30 (1942) [Chemical Abstract].

Mechoulam, et al., "Hashish. IV. The isolation and structure of cannabinolic, cannabidiolic and cannabigerolic acids," Tetrahedron, 21(5): 1223-9 (1965) [Chemical Abstract].

PCT/US2008/071659, PCT Article 19(1) Amendment, submitted Feb. 12, 2009.

PCT/US2008/071659, Informal Comments to the Dec. 12, 2008 Written Opinion, submitted Oct. 16, 2009.

PCT/US2008/071659, International Preliminary Report on Patentability, issued Feb. 2, 2010.

PCT/US2008/071659, International Search Report, mailed Dec. 12, 2008.

Petrzilka, et al., "Synthesis of hashish components. IV," Helvetica Chimice Acta, 52(4): 1102-34 (1969) [Chemical Abstract].

Pillai, et al., "Physiochemical Evaluation, in Vitro Human Skin Diffusion, and Concurrent Biotransformation of 3-O-Alkyl Carbonate Prodrugs of Naltrexone," Pharmaceutical Research, 21(7): 1146-52 (2004).

Stinchcomb, et al., Permeation of Burprenorphine and Its 3-Alkyl-Ester Prodrugs Through Human Skin, Pharmaceutical Research, 13(10): 1519-23 (1996).

Weiner, et al., "Monomers and polymers of delta-1(6)-tetrahydrocannabinol and cannabidiol," European Journal of Medicinal Chemistry, 10(1): 79-83 (1975) [Chemical Abstract].

Büyüktimkin, et al., "Synthesis and Enhancing Effect of Dodecyl 2-(N,N-Dimethylamino)propionate on the Transepidermal Delivery of Indomethacin, Clonidine, and Hydrocortisone," Pharmaceutical Research, vol. 10(11), pp. 1632-1637 (1993).

Choi, et al., "Formulation and Evaluation of Ketorolac Transdermal Systems," Drug Delivery, vol. 14, pp. 69-74 (2007).

Gennaro, Alfonso, Remington: The Science and Practice of Pharmacy, 20th ed., pp. 842-843 (2000).

Gwak, et al., "Effect of vehicles and penetration enhancers on the in vitro percutaneous absorption of tenoxicam through hairless mouse skin," International Journal of Pharmaceutics, vol. 236, pp. 57-64 (2002).

Harrison, et al., "The Relative Effect of Azone® and Transcutal® on Permeant Diffusivity and Solubility in Human Stratum Corneum," Pharmaceutical Research, vol. 13(4), pp. 542-546 (1996).

Helton, et al., "Pharmacokinetic profiles in rats after intravenous, oral, or dermal administration of dapsone," Drug Metabolism and Disposition, vol. 28(8), pp. 925-929 (2000).

Møllgaard, et al., "Permeation of estradiol through the skin—effect of vehicles," International Journal of Pharmaceutics, vol. 15, pp. 185-197 (1983).

Puglia, et al., "Evaluation of in vitro percutaneous absorption of lorazepam and clonazepam from hydro-alcoholic gel formulations," International Journal of Pharmaceutics, vol. 228, pp. 79-87 (2001).

Sintov, et al., "Cutaneous biotransformation of N-(4-bromobenzoyl)-S,S-dimethyliminosulfurane and its product, 4-bromobenzamide, leading to percutaneous penetration enhancement of drugs: Initial evidence using hydrocortisone," Journal of Controlled Release, vol. 133, pp. 44-51 (2009).

Walters, Kenneth, "Penetration Enhancers and Their Use in Transdermal Therapeutic Systems," Transderal Drug Delivery Developmental Issues and Research Initiatives, Marcel Dekker, Inc., pp. 197-246.

FDA-approved product label for Marinol®.

Agu, et al., "Permeation of WIN 55,212-2, A Potent Cannabinoid Receptor Agonist, Across Human Tracheo-Broncial Tissue In Vitro and Rat Nasal Epithelium In Vivo", Journal of Pharmacy and Pharmacology, vol. 58, pp. 1459-1465 (2006).

Alsasua Del Valle, "Implication of Cannabinoids in Neurological Diseases", Cellular and Molecular Neurobiology, vol. 26, Nos. 4-6, pp. 579-591 (2006).

Baker, et al., "Cannabinoids Control Spasticity and Tremor in a Multiple Sclerosis Model", Nature, vol. 404, pp. 84-87 (2000).

Ben Amar, "Cannabinoids in Medicine: A Review of Their Therapeutic Potential", Journal of Ethnopharmacology 105, pp. 1-25 (2006).

Ben-Shabat, et al., "New Cannabidiol Deriviatives: Synthesis, Binding to Cannabinoid Receptor, and Evaluation of Their Antiinflammatory Activity", Journal of Medicinal Chemistry, vol. 49, No. 3, pp. 1113-1117 (2006).

Bisogno, et al., "The Endo Cannabinoid Signaling System: Biochemical Aspects", Pharmacology, Biochemistry and Behavior 81, pp. 224-238 (2005).

Bodó, et al., "A Hot New Twist to Hair Biology: Involvement of Vanilloid Receptor-1 (VR1/TRPV1) Signaling in Human Hair Growth Control", American Journal of Pathology, vol. 166, No. 4, pp. 985-998 (Apr. 2005).

Brown, et al., "In Vitro Metabolism of Cannabichromene in Seven Common Laboratory Animals", Drug Metabolism and Disposition, vol. 18, No. 6, pp. 1065-1070 (1990).

Burns, et al., "Cannabinoid Analgesia as a Potential New Therapeutic Option in the Treatment of Chronic Pain", The Annals of Pharmacotherapy, vol. 40, pp. 251-260 (2006).

Carrier, et al., "Inhibition of an Equilibrative Nucleoside Transporter by Cannabidiol: A Mechanism of Cannabinoid Immunosuppression", PNAS, vol. 103, No. 20, pp. 7895-7900 (2006).

Challapalli, et al., "In Vitro Experiment Optimization for Measuring Tetrahydrocannabinol Skin Permeation", International Journal of Pharmaceutics 241, pp. 329-339 (2002).

Clayton, et al., "CB1 and CB2 Cannabinoid Receptors are Implicated in Inflammatory Pain", Pain 96, pp. 253-260 (2002).

Colombo, et al., "Endocannabinoid System and Alcohol Addiction: Pharmacological Studies", Pharmacology Biochemistry and Behavior 81, pp. 369-380 (2005).

Crombie, et al., "Synthesis of Cannabinoids Carrying ω-Carboxy Substituents: The Cannabidiols, Cannabinol, and $\Delta^1$- and $\Delta^3$-Tetrahydrocannabinols of this Series", J. Chem. Perkin Trans. 1, pp. 1255-1262 (1988).

Croxford, "Therapeutic Potential of Cannabinoids in CNS Disease", CNS Drugs, vol. 17(3), pp. 179-202 (2003).

Davis, et al., "The Emerging Role of Cannabinoid Neuromodulators in Symptom Management", Support Care Cancer 15, pp. 63-71 (2007).

Di Marzo, et al., "Plant, Synthetic, and Endogenous Cannabinoids in Medicine", Annual Review of Medicine, vol. 57, pp. 553-574 (2006).

Di Marzo, et al., "The Endocannabinoid System and its Therapeutic Exploitation", Nature Reviews, vol. 3, pp. 771-784 (2004).

Dobrosi, et al., "Endocannabinoids Enhance Lipid Synthesis and Apoptosis of Human Sebocytes via Cannabinoid Receptor-2-Mediated Signaling", The FASEB Journal, vol. 22, pp. 1-11 (Oct. 2008).

Dogrul, et al., "Topical Cannabinoid Antinociception: Synergy With Spinal Sites", Pain 105, pp. 11-16 (2003).

Drysdale, et al., "Cannabinoids: Mechanisms and Therapeutic Applications in the CNS", Current Medicinal Chemistry, vol. 10, No. 24, pp. 2719-2732 (2003).

Felder, et al., "Cannabinoid Biology: The Search for New Therapeutic Targets", Molecular Interventions, vol. 6, No. 3, pp. 149-161 (2006).

Gordon, et al., "Alcohol and Marijuana: Effects on Epilepsy and Use by Patients with Epilepsy", Epilepsia, vol. 42, No. 10, pp. 1266-1272 (2001).

Grotenhermen, "Cannabinoids for Therapeutic Use: Designing Systems to Increase Efficacy and Reliability", American Journal of Drug Delivery, vol. 2(4), pp. 229-240 (2004).

Grotenhermen, "Clinical Pharmacokinetics of Cannabinoids", Journal of Cannabis Therapeutics, vol. 3, No. 1, pp. 3-51 (2003).

Grotenhermen, "Pharmacokinetics and Pharmacodynamics of Cannabinoids", Clinical Pharmacokinetics, vol. 40, No. 4, pp. 327-360 (2003).

Hamelink, et al., "Comparison of Cannabidiol, Antioxidants, and Diuretics in Reversing Binge Ethanol-Induced Neurotoxicity", The Journal of Pharmacology and Experimental Therapeutics, vol. 314, No. 2, pp. 780-788 (2005).

Hampson, et al., "Cannabidiol and (-)$\Delta^9$-tetrahydrocannabinol are Neuroprotective Antioxidants", Proceedings of the National Academy of Sciences, vol. 95, pp. 8268-8273 (1998).

Hohmann, et al., "Endocannabinoid Mechanisms of Pain Modulation", The American Association of Pharmaceutical Scientists Journal, vol. 8(4), Article 79, pp. E693-E708 (2006).

Huskey, "Cannabinoids in Cancer Pain Management", Journal of Pain and Palliative Care Pharmacotherapy, vol. 20(3), pp. 43-46 (2006).

Jiang, et al., "Cannabinoids Promote Embryonic and Adult Hippocampus Neurogenesis and Produce Anxiolytic- and Antidepressant-Like Effects", The Journal of Clinical Investigation, vol. 115, No. 11, pp. 3104-3116 (2005).

Juntunen, et al., "In-Vitro Corneal Permeation of Cannabinoids and Their Water-Soluble Phosphate Ester Prodrugs", Journal of Pharmacy and Pharmacology, vol. 57, pp. 1153-1157 (2005).

Karsak, "Attenuation of Allergic Contact Dermatitis Through the Endocannabinoid System", Science, vol. 316, pp. 1494-1497 (2007).

Kehl, et al., "A Cannabinoid Agonist Differentially Attenuates Deep Tissue Hyperalgesia in Animal Models of Cancer and Inflammatory Muscle Pain", Pain 103, pp. 175-186 (2003).

Klein, "Cannabinoid-Based Drugs as Anti-Inflammatory Therapeutics", Nature Reviews, vol. 5, pp. 400-411 (2005).

Kogan, "Cannabinoids and Cancer", Mini-Reviews in Medicinal Chemistry, vol. 5, No. 10, pp. 941-952 (2005).

Lambert, et al., "The Endocannabinoid System: Drug Targets, Lead Compounds, and Potential Therapeutic Applications", Journal of Medicinal Chemistry, vol. 48, No. 16, pp. 5059-5087 (2005).

Lange, et al., "Recent Advances in $CB_1$ Cannabinoid Receptor Antagonists", Current Opinion in Drug Discovery and Development, vol. 7(4), pp. 498-506 (2004).

Lynch, "Preclinical Science Regarding Cannabinoids as Analgesics: An Overview", Autumn Pain Res Manage, vol. 10, Suppl. A, pp. 7A-14A (2005).

Malan, Jr., et al., "$CB_2$ Cannabinoid Receptor Agonists: Pain Relief Without Psychoactive Effects?", Current Opinion in Pharmacology, vol. 3, pp. 62-67 (2003).

Maldonado, et al., "Involvement of the Endocannabinoid System in Drug Addiction", Trends in Neurosciences, vol. 29, No. 4, pp. 225-232 (2006).

Manzanares, et al., "Interactions Between Cannabinoid and Opioid Receptor Systems in the Mediation of Ethanol Effects", Alcohol & Alcoholism, vol. 40, No. 1, pp. 25-34 (2005).

Marchalant, et al., "Anti-Inflammatory Property of the Cannabinoid Agonist Win-55212-2 in a Rodent Model of Chronic Brain Inflammation", Neuroscience 144, pp. 1516-1522 (2007).

Martinez, et al., "Dendritic Core—Shell Macromolecules Soluble in Supercritical Carbon Dioxide", Macromolecules, vol. 39, pp. 3978-3979 (2006); see also Martinez, et al., Supporting Information (attached).

McKallip, et al., "Cannabidiol-Induced Apoptosis in Human Leukemia Cells: A Novel Role of Cannabidiol in Regulation of $p22^{phox}$ and Nox4 Expression", Molecular Pharmacology, vol. 70, No. 3, pp. 897-908 (2006).

Mechoulan, et al., "Cannabidiol: An Overview of Some Chemical and Pharmacological Aspects. Part I: Chemical Aspects", Chemistry and Physics of Lipids 121, pp. 35-43 (2002).

Michalski, et al., "Cannabinoids Ameliorate Pain and Reduce Disease Pathology in Cerulein-Induced Acute Pancreatitis", Gastroenterology, vol. 132, No. 5, pp. 1968-1978 (2007).

Muccioli, et al., "Current Knowledge on the Antagonists and Inverse Agonists of Cannabinoid Receptors", Current Medicinal Chemistry, vol. 12, No. 12, pp. 1361-1394 (2005).

Pacher, et al., "The Endocannabinoid System as an Emerging Target of Pharmacotherapy", Pharmacological Reviews, vol. 58, No. 3, pp. 389-462 (2006).

Pertwee, "Cannabidiol as a Potential Medicine", Milestones in Drug Therapy: Cannabinoids as Therapeutics, pp. 47-65, Birkhäuser Basel (2005).

Pertwee, "The Therapeutic Potential of Drugs That Target Cannabinoid Receptors or Modulate the Tissue Levels or Actions of Endocannabinoids", The AAPS Journal, vol. 7, No. 3, Article 64, pp. E625-E654 (2005).

Rukwied, et al., "Cannabinoid Agonists Attenuate Capsaicin-Induced Responses in Human Skin", Pain 102, pp. 283-288 (2003).

Russo, "A Tale of Two Cannabinoids: The Therapeutic Rationale for Combining Tetrahydrocannabinol and Cannabidiol", Medical Hypotheses, pp. 1-13 (2005).

Stinchcomb, et al., "Human Skin Permeation of $\Delta^8$-tetrahydrocannabinol, Cannabidiol and Cannabinol", Journal of Pharmacy and Pharmacology, vol. 56, pp. 291-297 (2004).

Tchilibon, et al., "Synthesis of a Primary Metabolite of Cannabidiol", Organic Letters, vol. 2, No. 21, pp. 3301-3303 (2000).

Telek, et al., "Inhibition of Human Hair Follicle Growth by Endo- and Exocannabinoids", The FASEB Journal, vol. 21, pp. 1-8 (Nov. 2007).

Thomas, et al., "Cannabidiol Displays Unexpectedly High Potency as an Antagonist of $CB_1$ and $CB_2$ receptor Agonists In Vitro", British Journal of Pharmacology, vol. 150, pp. 613-623 (2007).

Valiveti, et al., "In Vitro/In Vivo Correlation Studies for Transdermal $\Delta^8$-THC Development", Journal of Pharmaceutical Sciences, vol. 93, No. 5, pp. 1154-1164 (2004).

Valiveti, et al., "Intranasal Absorption of $\Delta^9$-tetrahydrocannabinol and WIN55,212-2 Mesylate in Rats", European Journal of Pharmaceutics and Biopharmaceutics 65, pp. 247-252 (2007).

Valiveti, et al., "Liquid Chromatographic-Mass Spectrometric Qauntitation of $\Delta^9$-tetrahydrocannabinol and Two Metabolites in Pharmacokinetic Study Plasma Samples", Journal of Chromatography B 803, pp. 243-248 (2004).

Valiveti, et al., "Transdermal Delivery of the Synthetic Cannabinoid WIN 55,212-2 In Vitro/in Vivo Correlation", Pharmaceutical Research, vol. 21, No. 7. pp. 1137-1145 (2004).

Valiveti, et al., "Transdermal Permeation of WIN 55,212-2 and CP 55,940 in Human Skin In Vitro", International Journal of Pharmaceutics 278, pp. 173-180 (2004).

Williamson, et al., "Cannabinoids in Clinical Practice", Drugs, vol. 60, No. 6, pp. 1303-1314 (2000).

Fabin B, et al., "Localization of Lipophilic Molecules Penetrating Rat Skin in Vivo by Quantitative Autoradiography", International Journal of Pharmaceutics, Elsevier BV, vol. 74, No. 1, pp. 59-65 (1991); XP025544203 ISSN: 0378-5173.

Extended European Search Report for European Pat. Appl. No. 06 784 961.2 (PCT/US2006/023387), Jul. 23, 2009.

May 9, 2005 Final Office Action filed in U.S. Appl. No. 10/032,163.

Feb. 10, 2005 Amendment and Response filed in U.S. Appl. No. 10/032,163.

Sep. 10, 2004 Non-Final Office Action filed in U.S. Appl. No. 10/032,163.

Jul. 1, 2004 Request for Continued Examination filed in U.S. Appl. No. 10/032,163.

Mar. 2, 2004 Final Office Action filed in U.S. Appl. No. 10/032,163.

Dec. 22, 2003 Amendment and Response to Office Action filed in U.S. Appl. No. 10/032,163.

Sep. 23, 2003 Non-Final Office Action filed in U.S. Appl. No. 10/032,163.

International Search Report for PCT/US06/23387, mailed on Nov. 7, 2006.

Written Opinion of the International Searching Authority for PCT/US06/23387, mailed on Nov. 7, 2006.

"American Cancer Society Funds Research to Study 'Marijuana Patches' for Cancer Patients," Associated Press Release, Jan. 20, 2000.

"Institute of Medicine Releases Report on Medicinal Marijuana," Citation from PROMPT—Predicasts: PMT, PR Newswire, Mar. 17, 1999.

"Institute of Medicine Report: ONDCP and IOM Agree That 'Chemically-Defined Drugs'—Like Marinol—Not Smoked Marijuana is the Future of Cannabinoid Drugs," PR Newswire Assoc., Inc., Mar. 17, 1999.

"Institute of Medicine Report: What Marijuana Legalizers Won't Tell You: Substance Found in Marijuana Can Be Delivered Through Various Legal Means," PR Newswire Assoc., Inc., Mar. 17, 1999.

"ACS Marijuana Patch Research Grant Q&A for American Cancer Society Staff and Volunteers," Statement taken from the Cancer Information Database on Lotus Notes, Jan. 20, 1999.

NCADI: NIH's Workshop on the Medical Utility of Marijuana, available at http://www.health.org/medmarj.htm, 1998, pp. 1-33.

"Therapeutic Uses of *Cannabis*," British Medical Assoc., Harwood Academic Publishers, 1997, pp. 10, 11, 26-45, 75-81.

"Atlantic Report on Potent Analgesic/Anti-Inflammatory Agent Presented at International Conference on Prostaglandins and Related Compounds," Citation from PROMPT—Predicasts: PMT, Business Wire, Sep. 24, 1996.

"Lifegroup's Breakthrough in Inflammation," Pharmaceutical Business News, May 12, 1995.

"Anandamide May be Natural Ligand of Cannabinoid Receptor," Citation from PREDICAST F&S Index (PFS): PFS, Chemical & Engineering News, Dec. 21, 1992, p. 16.

Abraham, M. H. et al., "The Factors that Influence Skin Penetration of Solutes," J. Pharm. Parmacol., vol. 47, 1995, pp. 8-16.

Abraham, M. H. "Application of Solvation Equations to Chemical and Biochemical Processes," Pure and Applied Chem., vol. 65, No. 12, 1993, pp. 2503-2512.

Abrahamov, A. et al., "An Efficient New Cannabinoid Antiemetic in Pediatric Oncology," Life Sciences, vol. 56, Nos. 23/24, 1995, pp. 2097-2102.

Adams, MD et al., "A cannabinoid with cardiovascular activity but no overt behavioral effects" 33(9) Experientia 1204-05 (1977).

Alvarez, F. J. et al., (2008). "Neuroprotective Effects of the Nonpsychoactive Cannabinoid Cannabidiol in Hypoxic-Ischemic Newborn Piglets." Pediatric Research 64(6): 653-658.

Anderson and Raykar, "Solute Structure-Permeability Relationships in Human Stratum Corneum," J Investigative Dermatology, vol. 93 No. 2, 1989, pp. 280-286.

Aragona, M., et al., (2009). "Psychopathological and Cognitive Effects of Therapeutic Cannabinoids in Multiple Sclerosis: A Double-Blind, Placebo Controlled, Crossover Study." Clin Neuropharmacol.

Arthur, C., "Body's Pain Relief Mimics *Cannabis*," The UK Independent vol. 98, No. 572, Jul. 16, 1998.

Attal N. et al., (2004) "Are oral cannbinoids safe and effective in refractory neuropathic pain?" Eur J Pain 8: 173-177.

Aung et al., "Influence of the N-1 Alkyl Chain Length of Cannabimimetic Indoles Upon $CB_1$ and $CB_2$ Receptor Binding," Drug and Alcohol Dependence, vol. 60, 2000, pp. 133-140.

Barak V et al., (1992) "The M20 IL-1 inhibitor prevents onset of adjuvant arthritis." Biotherapy 4: 317-323.

Barnes, M. P. (2006). "Sativex (R): clinical efficacy and tolerability in the treatment of symptoms of multiple sclerosis and neuropathic pain." Expert Opinion on Pharmacotherapy 7(5): 607-615.

Belgrave, B.E. et al., "The effect of cannabidiol, alone and in combination with ethanol, on human performance" Psychopharmacology,64(2) (1979) p. 243-6.

Berman, J. S. et al., (2004). "Efficacy of two cannabis based medicinal extracts for relief of central neuropathic pain from brachial plexus avulsion: results of a randomised controlled trial" Pain 112(3): 299-306.

Bickers, D. R. et al., "Epidermis: A Site of Drug Metabolism in Neonatal Rat Skin, Studies on Cytochrome P-450 Content and Mixed Function Oxidase and Epoxide Hydrolase Activity," Molecular Pharmacology, vol. 21, 1982, pp. 239-247.

Bird, K.D. et al., "Intercannabinoid and cannabinoid-ethanol interactions and their effects on human performance" Psychopharmacology (Berlin, Germany), 1980. 71(2): p. 181-8.

Bisogno, T. et al., (2001). "Molecular targets for cannabidiol and its synthetic analogues: effect on vanilloid VR1 receptors and on the cellular uptake and enzymatic hydrolysis of anandamide" Br J Pharmacol 134(4): 845-52.

Blake, D. R. et al., (2006). "Preliminary assessment of the efficacy, tolerability and safety of a *cannabis*-based medicine (Sativex) in the treatment of pain caused by rheumatoid arthritis" Rheumatology (Oxford, England) 45(1): 50-2.

Bondi, A. "van der Waals Volumes and Radii," J. Physical Chem., vol. 68, No. 3, Mar. 16, 1964, pp. 441-451.

Bornheim, L. M. et al., "Human Hepatic Microsomal Metabolism of Delta-1-Tetrahydrocannabinol," Drug Metabolism and Disposition, vol. 20, No. 2, 1992, pp. 241-246.

Bornheim, L.M. et al., "Effect of cannabidiol on cytochrome P-450 and hexobarbital sleep time" 30(5) Biochem. Pharmacology, pp. 503-507 (1981).

Bornheim, L. M. and M. A. Correia (1989). "Purification and characterization of a mouse liver cytochrome P-450 induced by cannabidiol" Mol Pharmacol 36(3): 377-83.

Bornheim, L. M. and M. A. Correia (1990). "Selective inactivation of mouse liver cytochrome P-450IIIA by cannabidiol" Molecular Pharmacology 38(3): 319-26.

Bornheim, L. M. and M. A. Correia, "Purification and characterization of the major hepatic cannabinoid hydroxylase in the mouse: a possible member of the cytochrome P-450IIC subfamily" 40 2 Molecular Pharmacology 228-34 (1991).

Bornheim, L. M. et al., (1993). "Characterization of cannabidiol-mediated cytochrome P450 inactivation" Biochemical Pharmacology 45(6): 1323-31.
Bornheim, L. M. et al., (1993). "Induction and genetic regulation of mouse hepatic cytochrome P450 by cannabidiol" Biochem Pharmacol 48(1): 161-71.
Bornheim, L. M. and M. P. Grillo (1998). "Characterization of Cytochrome P450 3A Inactivation by Cannabidiol: Possible Involvement of Cannabidiol-Hydroxyquinone as a P450 Inactivator" Chemical Research in Toxicology 11(10): 1209-1216.
Bornheim, L. M. et al., (1994). "The effect of cannabidiol on mouse hepatic microsomal cytochrome P450-dependent anandamide metabolism" Biochemical and Biophysical Research Communications 197(2): 740-6.
Borys, H. K. et al., (1979). "Development of tolerance to the prolongation of hexobarbitone sleeping time caused by cannabidiol" British J. Pharmacology 67(1): 93-101.
Braida, D. et al., (2003). "Post-ischemic treatment with cannabidiol prevents electroencephalographic flattening, hyperlocomotion and neuronal injury in gerbils." Neuroscience Letters 346(1-2): 61-4.
Bright, T.P. et al., "Cardiopulmonary effects of cannabidiol in anesthetized mongrel dogs" 31(3) Toxicology and Applied Pharmvcology 520-26 (1975).
Brady, C. M. et al., (2004). "An open-label pilot study of *cannabis*-based extracts for bladder dysfunction in advanced multiple sclerosis." Multiple Sclerosis 10(4): 425-433.
Bronaugh, R. L., "In Vitro Viable Skin Model," *Models for Assessing Drug Absorption and Metabolism*, vol. 8, Chapter 20, Plenum Press, 1996, pp. 375-386.
Bronaugh and Stewart, "Methods for In Vitro Percutaneous Absorption Studies III: Hydrophobic Compounds," J. Pharmaceutical Sciences, vol. 73, No. 9, Sep. 1984, pp. 1255-1258.
Buckwalter JA and Martin JA (2006) "Osteoarthritis" Adv Drug Deliv Rev 58: 150-167.
Burstein SH and Zurier RB, "Cannabinoids, endocannabinoids, and related analogs in inflammation" 11(1) AAPS 109-19 (2009).
Capasso, R. et al., (2008). "Cannabidiol, extracted from *Cannabis sativa*, selectively inhibits inflammatory hypermotility in mice" British J. Pharmacology 154(5): 1001-1008.
Carlini, E.A. and J.M. Cunha, "Hypnotic and antiepileptic effects of cannabidiol" J. Clinical Pharmacology, 1981. 21(8-9, Suppl.): p. 417-27.
Carney, J.M. et al., "Effects of systemic and intraventricular administration of cannabinoids on schedule-controlled responding in the squirrel monkey" J. pharmacology and experimental therapeutics, 1979. 210(3): p. 399-404.
Chang, M.C. and H. Schuel, "Reduction of the fertilizing capacity of sea urchin sperm by cannabinoids derived from marihuana. II. Ultrastructural changes associated with inhibition of the acrosome reaction" Molecular Reproduction and Development, 1991. 29(1): p. 60-71.
Chang, A. E. et al., "Delta-9-Tetrahydrocannibinol as an Antiemetic in Cancer Patients Receiving High-Dose Methotrexate," Annals of Internal Med., vol. 91, 1979, pp. 819-824.
Cheer et al., "Lack of Response Suppression Follows Repeated Ventral Tegmental Cannabinoid Administration: An In Vitro Electrophysiological Study," Neuroscience, vol. 99, No. 4, 2000, pp. 661-667.
Collier, S. W. et al., "Cutaneous Metabolism," *In Vitro Percutaneous Absorption: Principles and Fundamentals, and Applications*, R. L. Bronaugh and H. I. Maibach, Editors, CRC Press, 1991, pp. 67-83.
Collin, C. et al., (2006). "A randomised controlled study of Sativex (R) in patients with symptoms of spasticity due to multiple sclerosis" Multiple Sclerosis 12: S111-S112 (abstract).
Collin, C. et al., (2007). "Randomized controlled trial of *cannabis*-based medicine in spasticity caused by multiple sclerosis" European J. Neurology 14(3): 290-296.
Collin, C. and P. Duncombe (2006). "Meta-analysis of the effects of Sativex (R) on spasticity associated with multiple sclerosis" Multiple Sclerosis 12: S13-S13 (abstract).
Collin, C. et al., (2007). "Results of an open-label extension trial of sativex (THC : CBD) in patients with multiple sclerosis and symptoms of spasticity" Multiple Sclerosis 13: S129-S129 (abstract).
Collin, C. et al., (2005). "A *cannabis*-based medicine (Sativex) has sustained efficacy in the treatment of spasticity in multiple sclerosis" J. Neurology Neurosurgery and Psychiatry 76(9): 1316-1316 (abstract).
Comelli, F. et al., (2008). "Antihyperalgesic effect of a *Cannabis sativa* extract in a rat model of neuropathic pain: mechanisms involved" Phytotherapy research PTR 22(8): 1017-24.
Consroe, P. et al., (1991). "Assay of plasma cannabidiol by capillary gas chromatography/ion trap mass spectroscopy following high-dose repeated daily oral administration in humans" Pharmacology, Biochem., and Behavior 40(3): 517-22.
Consroe, P. et al., (1991). "Controlled clinical trial of cannabidiol in Huntington's disease" Pharmacology, Biochem., and Behavior 40(3): 701-8.
Consroe et al., "Effects of cannabidiol in animal models of neurological dysfunction," 7 Marijuana: An International Research Report 147 (1988) pp. 147-152.
Consroe, P. et al., (1986). "Open label evaluation of cannabidiol in dystonic movement disorders" Int'l J Neuroscience 30(4): 277-82.
Consroe, P. et al., "Interaction of cannabidiol and alcohol in humans" Psychopharmacology, 1979. 66(1): p. 45-50.
Consroe and Sandyk, "Potential Role of Cannabinoids for Therapy of Neurological Disorders," *Marijuana/Cannabinoids Neurobiology and Neurophysiology*, L. Murphy and A. Bartke, Editors, CRC Press, 1992, pp. 459-524.
Constantinescu, C. S. and N. Sarantis (2006). "Long-term open-label treatment with Sativex (R) in patients with multiple sclerosis" Multiple Sclerosis 12: S111-S111 (abstract).
Costa B. et al., (2003) "Cannabidiol is an oral effective therapeutic agent both in acute inflammation and in chronic FCA-induced arthritis" First Eur. Workshop on Cannabinoid Research. Madrid (Spain), p. 62.
Costa B. et al., (2004) "Oral anti-inflammatory activity of cannabidiol, a non-psychoactive constituent of cannabis, in acute carrageenan-induced inflammation in the rat paw" Naunyn-Schmiedebergs Arch Pharmacol 369: 294-299.
Costa B. et al., (2004) "Vanilloid TRPV1 receptor mediates the antihyperalgesic effect of the nonpsychoactive cannabinoid, cannabidiol, in a rat model of acute inflammation" Br J Pharmacol 143: 247-250.
Costa B et al., (2007) "The non-psychoactive *cannabis* constituent cannabidiol is an orally effective therapeutic agent in rat chronic inflammatory and neuropathic pain" Eur J Pharmacol 556: 75-83.
Courtenay JS et al., "Immunisation against heterologous type II collagen induces arthritis in mice" 283(5748) Nature 666-68 (1980).
Crippa, J.A.d.S. et al., "Effects of Cannabidiol (CBD) on Regional Cerebral Blood Flow" Neuropsychopharmacology, 2004. 29(2): p. 417-426.
Croxford, J. L. et al., (2008). "Cannabinoid-mediated neuroprotection, not immunosuppression, may be more relevant to multiple sclerosis" J. Neuroimmunology 193(1-2): 120-129.
Cunha, J.M., et al., "Chronic administration of cannabidiol to healthy volunteers and epileptic patients" Pharmacology, 1980. 21(3): p. 175-85.
Dajani et al., "1',1'-Dimethylheptyl-Δ-8-tetrahydrocannabinol-11-oic Acid: A Novel, Orally Effective Cannabinoid with Analgesic and Anti-inflammatory Properties," J. Pharmacology and Experimental Therapeutics, vol. 291, No. 1, 1999, pp. 31-38.
Dalterio, S. et al., "Early cannabinoid exposure influences neuroendocrine and reproductive functions in male mice: I. Prenatal exposure" Pharmacology, Biochem., and Behavior, 1984. 20(1): p. 107-13.
Dalterio, S. et al., "Early Cannabinoid Exposure Influences Neuroendocrine and Reproductive Functions in Mice II Postnatal Effects" Pharmacology, Biochem., and Behavior, 1984. 20(1): p. 115-123.
Dalterio, S.L. and D.G. deRooij, "Maternal cannabinoid exposure. Effects on spermatogenesis in male offspring" Int J Androl, 1986. 9(4): p. 250-8.
Dalterio, S.L. et al., "Maternal or paternal exposure to cannabinoids affects central neurotransmitter levels and reproductive function in male offspring" Marihuana and Medicine 1999: p. 441-48.

Dalterio, S. et al., (1986). "Perinatal cannabinoid exposure: effects on hepatic cytochrome P-450 and plasma protein levels in male mice" Teratology 33(2): 195-201.

Dalton et al. "Influence of cannabidiol on delta-9-tetrandrocannbinol effects," 19(3) Clinical Pharmacology and Therapeutics 300-09 (1976).

Debruyne, D. et al., "Comparison of Three Advanced Chromatographic Techniques for *Cannabis* Identification," Bulletin of Narcotics, vol. XLVI, No. 2, 1994, p. 109-121.

Denovan-Wright et al., "Cannabinoid Receptor Messenger RNA Levels Decrease in a Subset of Neurons of the Lateral Striatrum, Cortex and Hippocampus of Transgenic Huntington's Disease Mice," Neuroscience, vol. 98, No. 4, 2000, pp. 705-713.

Dirikoc, S. et al., (2007). "Nonpsychoactive cannabidiol prevents prion accumulation and protects neurons against prion toxicity" J. Neuroscience 27(36): 9537-9544.

de Ridder, D. et al., (2006). "Randomised controlled study of *cannabis*-based medicine (Sativex (R)) in patients suffering from multiple sclerosis associated detrusor overactivity" Multiple Sclerosis 12: S111-S111.

Deutsch, D. G. et al., (1991). "Potentiation of the inductive effect of phenobarbital on cytochrome P450 mRNAs by cannabidiol" Biochem Pharmacol 42(10): 2048-53.

Durst, R. et al., (2007). "Cannabidiol, a nonpsychoactive *Cannabis* constituent, protects against myocardial ischemic reperfusion injury" Am J Physiol Heart Circ Physiol 293(6): H3602-7.

El-Remessy et al., (2006). "Neuroprotective and blood-retinal barrier-preserving effects of cannabidiol in experimental diabetes" Am J Pathol 168(1): 235-44.

El-Remessy et al., (2003). "Neuroprotective effect of (-)Delta9-tetrahydrocannabinol and cannabidiol in N-methyl-D-aspartate-induced retinal neurotoxicity: involvement of peroxynitrite" Am J Pathol 163(5): 1997-2008.

Esposito, G. et al., (2006). "The marijuana component cannabidiol inhibits beta-amyloid-induced tau protein hyperphosphorylation through Wnt/beta-catenin pathway rescue in PC12 cells" J Mol Med 84(3): 253-8.

Esposito, G. et al., (2006). "Cannabidiol inhibits inducible nitric oxide synthase protein expression and nitric oxide production in beta-amyloid stimulated PC12 neurons through p38 MAP kinase and NF-kappa B involvement" Neuroscience Letters 399(1-2): 91-95.

Esposito, G. et al., (2007). "Cannabidiol in vivo blunts beta-amyloid induced neuroinflammation by suppressing IL-1beta and iNOS expression" Br J Pharmacol 151(8): 1272-9.

Flynn, G.L. "Cutaneous and Transdermal Delivery: Process and Systems of Delivery," *Modern Pharmaceutics*, Third Edition, vol. 72 Edited by Gilbert S. Banker and Christopher T. Rhodes, pp. 239-298.

Flynn, G. L. "Physiochemical Determinants of Skin Absorption," *Principals of Route-to-Route Extrapolation for Risk Assessment*, T. R. Gerrity and C. J. Henry, Editors, 1990, pp. 93-127.

Gallate et al., "Increased Motivation for Beer in Rats Following Administration of Cannabinoid CB1 Receptor Agonist," European J. Pharmacology, vol. 370, 1999, pp. 233-240.

Garcia-Arencibia, M. et al., (2007). "Evaluation of the neuroprotective effect of cannabinoids in a rat model of Parkinson's disease: Importance of antioxidant and cannabinoid receptor-independent properties" Brain Research 1134(1): 162-170.

Gattas, G.J.F. et al., "In vitro cytogenetic effects of cannabidiol on human lymphocyte cultures" Revista Brasileira de Genetica, 1989. 12(3): p. 613-23.

Gerostamoulos and Drummer, "Incidence of Psychoactive Cannabinoids in Drivers Killed in Motor Vehicle Accidents," J. Forensic Sciences, JFSCA, vol. 38, No. 3, May 1993, pp. 649-656.

Gerwin N. et al., (2006) "Intraarticular drug delivery in osteoarthritis" Adv Drug Deliv Rev 58: 226-242.

Gilgun-Sherki, Y. et al., (2003). "The CB1 cannabinoid receptor agonist, HU-210, reduces levodopa-induced rotations in 6-hydroxydopamine-lesioned rats" Pharmacology & Toxicology (Oxford, United Kingdom) 93(2): 66-70.

Glasstone, S. *Textbook of Physical Chemistry*, 2nd Edition, D. Van Nostrand, NY, 1946, pp. 529-531.

Gormley, M., "Researchers Test 'Marijuana Patch'," Associated Press Release, Jan. 20 no year referenced.

Green, D. E. et al., "Quantitation of Delta-9-Tetrahydrocannabinol and its Metabolites in Human Urine by Probability Based Matching GC/MS," *Cannabinoid Analysis in Physiological Fluids*, Vinson, J.A. Ed., Amer. Chemical Society, 1979 pp. 93-113.

Gohda, H. et al., (1990). "In vivo and in vitro metabolism of cannabidiol monomethyl ether and cannabidiol dimethyl ether in the guinea pig: on the formation mechanism of cannabielsoin-type metabolite from cannabidiol" Chem Pharm Bull (Tokyo) 38(6): 1697-701.

Giuiliani et al., "Effects of the Cannabinoid Receptor Agonist, HU 210, on Ingestive Behaviour and Body Weight of Rats," European J. Pharmacology, vol. 391, 2000, pp. 275-279.

Guy, G.W. and M.E. Flint, "A single centre, placebo-controlled, four period, crossover, tolerability study assessing, pharmacodynamic effects, pharmacokinetic characteristics and cognitive profiles of a single dose of three formulations of *cannabis* based medicine extracts (CBMEs) (GWPD9901), plus a two period tolerability study comparing pharmacodynamic effects and pharmacokinetic characteristics of a single dose of a cannabis based medicine extract given via two administration routes (GWPD9901 EXT)" J. *Cannabis* Therapeutics, 2003. 3(3): p. 35-77.

Guy, G. W. and P. J. Robson (2003). "A Phase I, double blind, three-way crossover study to assess the pharmacokinetic profile of cannabis based medicine extract (CBME) administered sublingually in variant cannabinoid ratios in normal healthy male volunteers (GWPK0215)." J. *Cannabis* Therapeutics 3(4): 121-152.

Guy, G. W. and P. J. Robson (2003). "A Phase I, open label, four-way crossover study to compare the pharmacokinetic profiles of a single dose of 20 mg of a *cannabis* based medicine extract (CBME) administered on 3 different areas of the buccal mucosa and to investigate the pharmacokinetics of CBME per oral in healthy male and female volunteers (GWPK0112)"J. *Cannabis* Therapeutics 3(4): 79-120.

Guy, G. W. and C. G. Stott (2005). "The development of Sativex—a natural *cannabis*-based medicine" Cannabinoids as Therapeutics: 231-263.

Dana C. Hammell et al, Effect of Cannabidiol Dose in CFA-Induced Mono-Arthritic Rat Model (Apr. 30, 2008) (Abstract).

Hampson, A. J. et al., (2000). "Neuroprotective antioxidants from marijuana." Reactive Oxygen Species: From Radiation to Molecular Biology 899: 274-282.

Han et al., "A Performance-Dependent Adjustment of the Retention Interval in a Delayed Non-Matching-to-Position Paradigm Differentiates Effects of Amnestic Drugs in Rats," European J. Pharmacology, vol. 403, 2000, pp. 87-93.

Hansch, C. et al., "'Aromatic' Substituent Constants for Structure—Activity Correlations," J. Medicinal Chem., vol. 16, No. 11, 1973, pp. 1207-1213.

Hargreaves K. et al., (1988) "A new and sensitive method for measuring thermal nociception in cutaneous hyperalgesia" Pain 32: 77-88.

Harris et al., "Spinal Anandamide Inhibits Nociceptive Transmission via Cannabinoid Receptor. Activation In Vivo," NeuroReport, vol. 11, No. 12, 2000, pp. 2817-2819.

Harvey D.J. and Brown N.K., "Comparative in vitro metabolism of the cannabinoids" 40(3) Pharmacology, Biochem., and Behavior 533-40 (1991).

Harvey D.J. and Mechoulam R., "Metabolites of cannabidiol identified in human urine" 20(3) Xenobiotica 303-20 (1990).

Hayakawa, K. et al., (2004). "Cannabidiol prevents infarction via the non-CBI cannabinoid receptor mechanism" Neuroreport 15(15): 2381-2385.

Hayakawa, K. et al., (2007). "Delayed treatment with cannabidiol has a cerebroprotective action via a cannabinoid receptor-independent myeloperoxidase-inhibiting mechanism" J. Neurochem. 102(5): 1488-1496.

Hayakawa, K. et al., (2007). "Repeated treatment with cannabidiol but not Delta9-tetrahydrocannabinol has a neuroprotective effect without the development of tolerance" Neuropharmacology 52(4): 1079-87.

Hoffman, D. et al., "On the Carcinogenicity of Marijuana Smoke," *Recent Advances in Phytochemistry*, Edited by V. C. Runeckles, Plenum Press, vol. 9, pp. 63-81.

Hollister, L.E., "Cannabidiol and cannabinol in man" Experientia, 1973. 29(7): p. 825-6.

Huestis, M.A., "Human cannabinoid pharmacokinetics" 4(8) Chem. and Biodiversity 1770-804 (2007).

Huffman, J.W. "Cannabimimetic indoles, pyrroles and indenes," 6(8) Current Medicinal Chem. 705-20 (1999).

Iskedjian, M. et al., (2007). "Meta-analysis of *cannabis* based treatments for neuropathic and multiple sclerosis-related pain" Current Medical Research and Opinion 23(1): 17-24.

Iuvone, T. et al., (2004). "Neuroprotective effect of cannabidiol, a non-psychoactive component from *Cannabis sativa*, on beta-amyloid-induced toxicity in PC12 cells." J Neurochem 89(1): 134-41.

Izquierdo, I. et al., Effect of Cannabidiol and of Other *Cannabis sativa* Compounds on Hippocampal Seizure Discharges. Psychopharmacologia, 1973. 28(1): p. 95-102.

Izquierdo, I. and Nasello, A.G., "Effects of Cannabidiol and of Diphenylhydantoin on Hippocampus and on Learning" Psychopharmacologia, 1973. 31(2): p. 167-175.

Izquierdo, I. and Tannhauser, M., "Letter: The effect of cannabidiol on maximal electroshock seizures in rats" 25(11) J. Pharmacy and Pharmacology 916-17 (1973).

Jaeger, W., et al., (1996). "Inhibition of cyclosporine and tetrahydrocannabinol metabolism by cannabidiol in mouse and human microsomes" Xenobiotica 26(3): 275-84.

Jay and Green, "Multiple-Drop Study of Topically Applied 1% Delta-9-Tetrahydrocannabinol in Human Eyes," Arch. Ophtalmol., vol. 101, Apr. 1983, pp. 591-593.

Jones Ca, et al., Health related quality of life outcomes after total hip and knee arthroplasties in a community based population 27(7) J Rheumatology 1745-52 (2000).

Juckel, G. et al., (2007). "Acute effects of Delta9-tetrahydrocannabinol and standardized *cannabis* extract on the auditory evoked mismatch negativity" Schizophrenia research 97(1-3): 109-17.

Juntunen, et al., "Synthesis, in Vitro Evaluation, and Intraocular Pressure Effects of Water-Soluble Prodrugs of Endocannabinoid Noladin Ether," 46(23) J. Medicinal Chem. 5083-86 (2003).

Kao, J. et al., "Cutaneous Metabolism of Xenobiotics," Drug Metabolism Reviews, vol. 22, No. 4, 1990, pp. 363-410.

Kasting, G. B. et al., "Effect of Lipid Solubility and Molecular Size on Percutaneous Absorption," Pharmacol. Skin, vol. 1, 1987, pp. 138-153.

Kavia, R. et al., (2006). "Randomised controlled trial of *cannabis* based medicine (CBM, sativex (R)) to treat detrusor overactivity in multiple sclerosis" Neurourology and Urodynamics 25(6): 622-623.

Kleber, H. D. (2005). "Future advances in addiction treatment" Clinical Neuroscience Research 5(2-4): 201-205.

Langford R. et al., (2006) "Transdermal fentanyl for improvement of pain and functioning in osteoarthritis" Arthritis Rheum 54(6): 1829-1837.

Lastres-Becker, I. et al., (2005). "Cannabinoids provide neuroprotection against 6-hydroxydopamine toxicity in vivo and in vitro: Relevance to Parkinson's disease" Neurobiology of Disease 19(1-2): 96-107.

Lawrence RC et al., (1998) "Estimates of the prevalence of arthritis and selected musculoskeletal disorders in the United States" Arthritis Rheum 41(5): 778-799.

Lawrence RC et al., "Estimates of the prevalence of arthritis and other rheumatic conditions in the United States. Part II" 58(1) Arthritis Rheum. 26-35 (2008).

Leigh JP et al., (2001) "Estimating the costs of job related arthritis" J Rheumatol 28: 1647-1654.

Levitz and Diamond, "Aspergillosis and Marijuana," Annals of Internal Med., vol. 115, No. 7, Oct. 1, 1991, pp. 578-579.

Lichtman, A.H., "SR 141716A Enhances Spatial Memory as Assessed in a Radial-Arm Maze Task in Rats," European J. of Pharmacology, vol. 404, 2000, pp. 175-179.

Lien, E. J. et al., "QSAR Analysis of Skin Permeability of Various Drugs in Man as Compared to in Vivo and in Vitro Studies in Rodents," Pharmaceutical Research, vol. 12, No. 4, 1995, pp. 583-587.

Lindgren, M., "New Light Shed on Cannabinoid Action (Statistical Data Included)," Citation from PROMPT—Predicasts: PMT, World Disease Weekly Plus, Oct. 11, 1999.

List, A. et al., (1977). "The effects of delta9-tetrahydrocannabinol and cannabidiol on the metabolism of gonadal steroids in the rat" Drug metabolism and disposition the biological fate of chemicals 5(3): 268-72.

Liu, P. et al., "Transport of Beta-Estradiol in Freshly Excised Human Skin in Vitro: Diffusion and Metabolism in Each Skin Layer," Pharmaceutical Research, vol. 11, No. 12, 1994, pp. 1777-1784.

Leweke, F.M. et al., "Different Effects of Nabilone and Cannabidiol on Binocular Depth Inversion in Man" Pharmacology, Biochem., and Behavior, (2000), 66(1): p. 175-181.

Lodzki et al., "Cannabidiol—transdermal delivery and anti-inflammatory effect in a murine model," 93 J. Controlled Release 377-87 (2003).

Lowry, O. H. et al., "Protein Measurement with the Folin Phenol Reagent," From the Department of Pharmacology, Washington University School of Medicine, St. Louis, Missouri, 1951, pp. 265-275.

Lu Y, et al., (2008) "Joint capsule treatment with enkephalin-encoding HSV-1 recombinant vector reduces inflammatory damage and behavioural sequelae in rat CFA monoarthritis" Eur J Neurosci 27:1153-1165.

Lyons-Johnson, D., "Cannabinoid Receptors Key to Stress Response," Citation from PROMPT—Predicasts: PMT, Agricultural Research, vol. 45, No. 6, Jun. 1997.

Malfait AM et al., (2000) "The nonpsychoactive *cannabis* constituent cannabidiol is an oral anti-arthritic therapeutic in murine collagen-induced arthritis" Proc Natl Acad Sci USA 97(17): 9561-9566.

Massi, P. et al., (2008). "5-Lipoxygenase and anandamide hydrolase (FAAH) mediate the antitumor activity of cannabidiol, a non-psychoactive cannabinoid" J Neurochem 104(4): 1091-100.

Matsuyama, S.S. and T.K. Fu, "In vivo cytogenetic effects of cannabinoids" J. Clinical Psychopharmacology, 1981. 1(3): p. 135-40.

Mattes, R. D. et al., "Cannabinoids and Appetite Stimulation," Pharmacology Biochem. and Behavior, vol. 49, No. 1, 1994, pp. 187-195.

McAllister et al., "An Aromatic Microdomain at the Cannabinoid CB1 Receptor Constitutes an Agonist/Inverse Agonist Binding Region" 46(24) J Medicinal Chem. 5139-52 (2003).

McArdle, K., et al., (2005). "Cannabidiol: transcriptional and post-transcriptional induction of rat P450s" Toxicology 213(3): 248-249 (Abstract).

McArdle, K. E. et al., (2003). "Cannabidiol (CBD) differentially inhibits Delta(9)-tetrahydrocannabinol (THC) metabolism by human P450s and induces CYP3A23 and CYP2B1/2 in vivo in rat" Toxicology 192(1): 90-91 (Abstract).

McArdle, K. E. et al., (2004). "Differential effects of cannabidiol (CBD) and Delta(9)-tetrahydrocannabinol (THC) on induction of rat cytochrome P450s (CYPs) following in vivo administration" Toxicology 194(3): 237-237 (Abstract).

McPartland, J. M. et al., (2007). "Meta-analysis of cannabinoid ligand binding affinity and receptor distribution: interspecies differences" Br J Pharmacol 152(5): 583-93.

McQueen et al., (2004). "Cannabidiol lacks the vanilloid VR1-mediated vasorespiratory effects of capsaicin and anandarnide in anaesthetised rats" European J. Pharmacology 491(2-3): 181-189.

Mechoulam, R. et al., (2002). "Cannabidiol: an overview of some pharmacological aspects" J. Clinical Pharmacology 42(11, Suppl.): 11S-19S.

Mechoulam and Gaoni., "A Total Synthesis of *dl*-Δ1-Tetrahydrocannabinol, the Active Constituent of Hashish," J. Amer. Chem. Society, vol. 87, 1965, pp. 3273-3275.

Melis et al., "Different Mechanisms for Dopaminergic Excitation Induced by Opiates and Cannabinoids in the Rat Midbrain," Progress in Neuro-Psychopharmacology and Biological Psychiatry, vol. 24 (2000), pp. 993-1006.

Mendizabal et al., "Cannabinoid System as a Potential Target for Drug Development in the Treatment of Cardiovascular Disease," Current Vascular Pharmacology, 2003, vol. 1, No. 3, 301-313.

Mishima, K. et al., (2005). "Cannabidiol Prevents Cerebral Infarction via a Serotonergic 5-Hydroxytryptamine1A Receptor-Dependent Mechanism" Stroke 36(5): 1071-1076.

Murphy, L.L. et al., "Effects of delta-9-tetrahydrocannabinol, cannabinol and cannabidiol, alone and in combinations, on luteinizing hormone and prolactin release and on hypothalamic neurotransmitters in the male rat" Neuroendocrinology, 1990. 52(4): p. 316-21.

Nahas G. and Trouve R., "Effects and interaction of natural cannabinoids on the isolated heart" 180(2) Proceedings Society for Experimental Biology and Med. 312-16 (1985).

Nalluri, Milligan, Chen, Crooks and Stinchcomb "In vitro release studies on matrix type transdermal drug delivery systems of naltrexone and its acetyl prodrug" Drug Development and Industrial Pharmacy 31(9) (2005), pp. 871-877.

Narimatsu, S. et al., (1990). "Inhibition of hepatic microsomal cytochrome P450 by cannabidiol in adult male rats" Chemical & Pharmaceutical Bulletin 38(5): 1365-8.

Narimatsu, S. et al., (1993). "Suppression of liver microsomal drug-metabolizing enzyme activities in adult female rats pretreated with cannabidiol" Biological & Pharmaceutical Bulletin 16(4): 428-30.

Nelson, K. et al., "A Phase II Study of Delta-9-Tetrahydrocannabinol for Appetite Stimulation in Cancer-Associated Anorexia," J. Palliative Care, vol. 10, No. 1, 1994, pp. 14-18.

Netzeband et al., "Cannabinoids Enhance NMDA-Elicited $Ca^{2+}$ Signals in Cerebellar Granule Neurons in Culture," J. Neuroscience, vol. 19, No. 20, Oct. 15, 1999, pp. 8765-8777.

Newhall, W. "Derivatives of (+)-limonene. III. A stereospecific sythesis of cis- and trans-delta-8(9)-p-menthene 1, 2-epoxides" 29 J Organic Chem. 185-86 (1964).

Nocerino et al., "*Cannabis* and Cannabinoid Receptors," Fitoterapia, vol. 71, 2000, pp. S6-S12.

Novak and Salenick., "*Cannabis* XXIV. A New Convenient Synthesis of Cannabinol," Tetrahedron Letters, vol. 23, No. 2, 1982, pp. 253-254.

Noyes, R. et al., "Analgesic Effect of Delta-9-Tetrahydrocannabinol," J. Clinical Pharmacology, Feb.-Mar. 1975, pp. 139-143.

Noyes, R. et al., "The Analgesic Properties of Delta-9-Tetrahydrocannabinol and Codeine," Clinical Pharmacology and Therapeutics, vol. 18, No. 1, 1975, pp. 84-89.

Nurmikko, T. J. et al., (2007). "Sativex successfully treats neuropathic pain characterised by allodynia: A randomised, double-blind, placebo-controlled clinical trial" Pain 133(1-3): 210-220.

Oz et al., "Endogenous Cannabinoid Anandamide Directly Inhibits Voltage-Dependent Ca2+ Fluxes in Rabbit T-Tubule Membranes," European J. Pharmacology, vol. 404, 2000, pp. 13-20.

Page et al., "Effects of Systemic 3-Nitropropionic Acid-Induced Lesions of the Dorsal Striatum on Cannabinoid and Mu-Opioid Receptor Binding in the Basal Ganglia," Experimental Brain Research, vol. 130, 2000, pp. 142-150.

Paria, B.C. et al., "The preim plantation mouse embryo is a target for cannabinoid ligand-receptor signaling" Proc Natl Acad Sci U S A, 1995. 92(21): p. 9460-4.

Patra, P.B. and R.M. Wadsworth, "Quantitative evaluation of spermatogenesis in mice following chronic exposure to cannabinoids" Andrologia, (1991) 23(2): p. 151-6.

Pertwee, R. G. (2004). "Pharmacological and therapeutic targets for Delta(9)-tetrahydrocannabinol and cannabidiol" Euphytica 140(1-2): 73-82.

Pertwee, R. G., "The central neuropharmacology of psychotropic cannabinoids" 36(2-3) Pharmacology and Therapeutics 189-261 (1988).

Pertwee, R.G., "Neuropharmacology and Therapeutic Potential of Cannabinoids," Addiction Biology, vol. 5, 2000, pp. 37-46.

Perez, J. (2006). "Combined cannabinoid therapy via an oromucosal spray" Drugs of today (Barcelona, Spain 1998) 42(8): 495-503.

Perez, J. and M. V. Ribera (2008). "Managing neuropathic pain with Sativex: a review of its pros and cons" Expert Opinion on Pharmacotherapy 9(7): 1189-1195.

Perez-Reyes, M. et al., "Comparison of the pharmacological activity in man of intravenously administered 9-tetrahydrocannabinol, cannabinol, and cannabidiol" Experientia, 1973. 29(11): p. 1368-9.

Perras, C. (2005). "Sativex for the management of multiple sclerosis symptoms" Issues in emerging health technologies(72): 1-4.

Pertwee, R. G. (2005). "Pharmacological actions of cannabinoids" Handb Exp Pharmacol(168): 1-51.

Pertwee, R. G. et al., (2005). "Evidence that (-)-7-hydroxy-4'-dimethylheptyl-cannabidiol activates a non-CB(1), non-Cb(2), non-TRPV1 target in the mouse vas deferens" Neuropharmacology 48(8): 1139-46.

Plasse, T. F. et al., "Recent Clinical Experience With Dronabinol," Pharmacology Biochem., & Behavior, vol. 40, 1991, pp. 695-700.

Pop, E. et al., "Derivatives of Dexanabinol. I. Water-soluble Salts of Glycinate Esters," Pharmaceutical Research, vol. 13, No. 1, 1996, pp. 62-69.

Pop et al., "Amino acid esters of dexanabinol (HU-211); prodrugs and analogs" Book of Abstracts, $210^{th}$ ACS National Meeting, Chicago, IL, Aug. 20-24, 1995 (Pt. 2): IMEDI-155.

Pop, E., "Contributions to the chemistry of synthetic cannabinoids." Roumanian Chemical Quarterly Review vol. 8(1), pp. 19-44 (2001).

Pop et al., "Hydrolytic stability of allylic and phenolic esters of some synthetic cannabinoids: a theoretical (AM1) study." 22 Int'l J Quantum Chem., Quantum Biology Symposium 137-43 (1995).

Potts, R. O. et al., "A Predictive Algorithm for Skin Permeability: The Effects of Molecular Size and Hydrogen Bond Activity," Pharmaceutical Research, vol. 12, No. 11, 1995, pp. 1628-1633.

Potts and Guy, "Predicting Skin Permeability," Pharmaceutical Research, vol. 9, No. 5, 1992, pp. 663-669.

Pugh, Jr., G. et al., "The Roles of Endogenous Opioids in Enhancing the Antinociception Produced by the Combination of the Delta-9-Tetahydrocannabinol and Morphine in the Spinal Cord," J. Pharmacology and Experimental Therapeutics, vol. 279, No. 2, 1996, pp. 608-616.

Reggio, P. H. et al., "Pharmacophores for ligand recognition and activation/inactivation of the cannabinoid receptors" 9(20) Current Pharmaceutical Design 1607-33 (2003).

Reggio et al., "The Bioactive Conformation of Aminoalkylindoles at the Cannabinoid CB1 and CB2 Receptors: Insights Gained from (E)- and (Z)-Naphthylidene Indenes." 41(26) J Medicinal Chem. 5177-87 (1998).

Revuelta, A.V. et al., "Effect of cannabinoids on the turnover rate of acetylcholine in rat hippocampus, striatum and cortex." Naunyn Schmiedebergs Arch Pharmacol, 1978. 304(2): p. 107-10.

Richter A. and Loescher, W. "(+)-WIN 55,212-2, a novel cannabinoid receptor agonist, exerts antidystonic effects in mutant dystonic hamsters" 264(3) European J Pharmacology 371-77 (1994).

Richardson et al., "SR 141716A, A Cannabinoid Receptor Antagonist, Produces Hyperalgesia in Untreated Mice," European J. Pharmacology, vol. 319, 1997, pp. R3-R4.

Rog David, et al., (2005). "Randomized, controlled trial of *cannabis*-based medicine in central pain in multiple sclerosis" Neurology 65(6): 812-9.

Rog, D. J. et al., (2006). "A Randomized controlled trial of sativex, a *cannabis* based medicine (CBM), in central neuropathic pain due to multiple sclerosis, followed by an open-label extension" Neurolooy 66(5): A31-A31 (abstract).

Rog, D. J. et al., (2007). "Long term use of Sativex in multiple sclerosis central pain: Dosing and. changes in concomitant analgesia" European J Pain 11(SI:1B6) (abstract).

Rog, D. J. et al., (2007). "Oromucosal delta9-tetrahydrocannabinol/cannabidiol for neuropathic pain associated with multiple sclerosis: an uncontrolled, open-label, 2-year extension trial" Clin Ther 29(9): 2068-79.

Romero et al., "Loss of Cannabinoid Receptor Binding and Messenger RNA Levels and Cannabinoid Agonist-Stimulated [$^{35}$S]Guanylyl-5'-O-(thio)-Triphosphate Binding in the Basal Ganglia of Aged Rats," Neuroscience, vol. 84, No. 4, 1998, pp. 1075-1083.

Rosenkrantz, H. and Hayden D.W., "Acute and subacute inhalation toxicity of Turkish marihuana, cannabichromene and cannabidiol in rats" 48(3) Toxicology and Applied Pharmacology 375-86 (1979).

Rosenkrantz, H. et al., "Toxicity of short-term administration of cannabinoids to rhesus monkeys" 58(1) Toxicology and Applied Pharmacology 118-31 (1981).

Rubin, A. et al., "Physiologic Disposition of Nabilone, a Cannabinol Derivative, in Man," Clinical Pharmacology and Therapeutics, vol. 22, No. 1, 1977, pp. 85-91.

Russo, E. B. (2003). "Safety, tolerability, and efficacy of orally administered cannabinoids in MS" Neurology 60(4): 729-30; author reply 729-30.

Russo, E. B. (2005). "Sativex *cannabis* based medicine maintains improvements in sleep quality in patients with multiple sclerosis and neuropathic pain" Neurology 64(6): A46-A47.

Russo, E. B. (2008). "Cannabinoids in the management of difficult to treat pain" Therapeutics and Clinical Risk Management 4(1): 245-259.

Russo, E. B. et al., (2007). "*Cannabis*, pain, and sleep: lessons from therapeutic clinical trials of Sativex, a *cannabis*-based medicine" Chem. & Biodiversity 4(8): 1729-1743.

Sagredo, O. et al.: (2007). "Cannabidiol reduced the striatal atrophy caused 3-nitropropionic acid in vivo by mechanisms independent of the activation of cannabinoid, vanilloid TRPV1 and adenosine A2A receptors" Eur J Neurosci 26(4): 843-51.

Sallan, S. F. et al., "Antiemetic Effect of Delta-9-Tetrahydrocannabinol in Patients Receiving Cancer Chemotherapy," New England J. Med., vol. 293, No. 16, Oct. 16, 1975, pp. 795-797.

Salzet et al., "Comparative Biology of the Endocannabinoid System: Possible Role in the Immune Response," European J. Biochem., vol. 267, 2000, pp. 4917-4927.

Sarantis, N. et al., (2005). "The effect of escape analgesia on pain relief produced by sativex" J. Neurology 252: 154-154 (Abstract).

Selvarajah, D. et al., (2006). "Treatment of painful diabetic neuropathy with Sativex (a *cannabis* based medicinal product)—results of a randomised placebo controlled trial" Diabetologia 49: 671-672 (Abstract).

Sepe et al., "Bioactive Long Chain N-Acylethanolamines in Five Species of Edible Bivalve Molluscs, Possible Implications for Mollusc Physiology and Sea Food Industry," Biochimica et Biophysica Acta, vol. 1389, 1998, pp. 101-111.

Serpell, M. G. and N. Sarantis (2006). "Long-term open-label treatment with Sativex (R), a *cannabis* based medicine, in neuropathic pain of various aetiologies, and spasticity due to multiple sclerosis" European J. Neurology 13: 239-239 (abstract).

Serpell, M. G. et al., (2005). "The effect of sativex on the Pain Disability Index and the treatment of neuropathic pain" J. Neurology 252: 155-155 (abstract).

Serpell, M. G. et al., (2004). "Sativex (R) in the treatment of pain of neurological origin or symptoms of multiple sclerosis: Interim analysis of a long-term, open-label, safety and tolerability study" European J. Neurology 11: 148-148 (abstract).

Shen et al., "Cannabinoid Receptor Agonists Protect Cultured Rat Hippocam pal Neurons from Excitotoxicity," Molecular Pharmacology, vol. 54, 1998, pp. 459-462.

Shepard, R. M., "Pharmacokinetics of Levonantradol in Laboratory Animals and Man," J. Clinical Pharmacology, No. 21: 190S-200S, 1981.

Showalter et al., "Evaluation of binding in a transfected cell line expressing a peripheral cannabinoid receptor (CB2): identification of cannabinoid receptor subtype selective ligands" 278(3) J Pharmacology and Experimental Therapeutics 989-99 (1996).

Sibbald, B. (2005). "Conditional okay for cannabis prescription drug" Canadian Medical Assoc. J. 172(13): 1672.

Siegel, C. et al., "An Optically Active Terpenic Synthon for $\Delta^9$-Cannabinoids: Synthesis of (-)-11-Hydroxy-Delta-9-Tetrahydrocannabinol (THC) and its 1',1'-Dimethylheptyl Analogue," J. Organic Chem., vol. 54, 1989, pp. 5428-5430.

Siemens A.J. and Kalant H. "Metabolism of delta-1-tetrahydrocannabinol by rats tolerant to *cannabis*" 52(6) Candian J Physiology and Pharmacology 1154-66 (1974).

Siemens A.J. et al., "Effect of *cannabis* on pentobarbital-induced sleeping time and pentobarbital metabolism in the rat" 23(3) Biochemical Pharmacology 477-88 (1974).

Sluka KA et al., (1993) "Joint inflammation and hyperalgesia are reduced by spinal bicuculline" Neuroreport 5:109-112.

Smith, P. F. (2007). "Symptomatic treatment of multiple sclerosis using cannabinoids: recent advances." Expert Review of Neurotherapeutics 7(9): 1157-1163.

Smiley K.A. et al., "Effects of cannabinoids on the perfused rat heart" 14(4) Research Communications in Chemical Pathology and Pharmacology 659-75 (1976).

Song, Z.H. and Bonner, T.I. "A lysine residue of the cannabinoid receptor is critical for receptor recognition by several agonists but not Win55215-2" 49(5) Molecular Pharmacology 891-96 (1996).

Stinchcomb, A. L. et al., "A Solubility and Related Physicochemical Property Comparison of Buprenorphine and its 3-Alkyl Esters," Pharmaceutical Research, vol. 12, No. 10, 1995, pp. 1526-1529.

Stinchcomb et al., "Straight-chain, naltrexone ester prodrugs: diffusion and concurrent esterase biotransformation in human skin" 91(12) J Pharmaceutical Science, pp. 2571-2578 (2002).

Stott, C. G. et al., (2008). "Comparison of pharmacokinetic profiles of inhaled delta-9-tetrahydrocannabinol (THC) from smoked *cannabis* with Sativex (R) oromucosal spray in humans, implications for possible symptomatic treatment in multiple sclerosis" European J Neurology 15: 365-365 (abstract).

Szallasi et al., "New Perspectives on Enigmatic Vanilloid Receptors," Trends in Neurosciences, vol. 23(10) (2000), pp. 491-497.

Tashkin, D. P. et al., "Bronchial Effects of Aerosolized Delta-9-Tetrahydrocannabinol in Healthy and Asthmatic Subjects," Amer. Review of Respiratory Disease, vol. 115, 1977, pp. 57-65.

Tayar, N. E. et al., "Percutaneous Penetration of Drugs: A Quantitative Structure—Permeability Relationship Study," J. Pharmaceutical Sciences, vol. 80, No. 8, Aug. 1991, pp. 744-749.

Taylor, D. N. et al., "Samonellosis Associated with Marijuana—A Multistate Outbreak Traced by Plasmid Fingerprinting," New England J. Med., vol. 306, No. 21, 1982, pp. 1249-1253.

Thomas and Martin, "In Vitro Metabolism of (-)-cis-3-[2-hydroxy-4-(1,1-dimethylheptyl) phenyl]-trans-4-(3-hydroxypropyl) Cyclohexanol, A Synthetic Bicyclic Cannabinoid Analog," Drug Metab. Dispos., vol. 18, 1990, pp. 1046-1054.

Tomida, I. et al., "Effect of sublingual application of cannabinoids on intraocular pressure: a pilot study" J of Glaucoma, 2006. 15(5): p. 349-53.

Touitou and Fabin, "Altered Skin Permeation of a Highly Lipophilic Molecule: Tetrahydrocannabinol," Int'l J. Pharmaceutics, vol. 43, 1988, pp. 17-22.

Touitou, E. et al., "Transdermal Delivery of tetrahydrocannabinol," Int'l J. Pharmaceutics, vol. 43, 1988, pp. 9-15.

Tramposch, A. et al., "Cannabinoid-induced enhancement and depression of cat monosynaptic reflexes" Neuropharmacology, 1981. 20(6): p. 617-21.

Trouve R. and Nahas G. "Cardiac dynamics of the Langendorff perfused heart" 180(2) Proceedings Society for Experimental Biology and Med. 303-11 (1985).

Turkanis, S.A. and R. Karler, "Excitatory and depressant effects of delta 9-tetrahydrocannabinol and cannabidiol on cortical evoked responses in the conscious rat" Psychopharmacology, 1981. 75(3): p. 294-8.

Ungerleider, et al., "Contamination of Marihuana Cigarettes with Pathogenic Bacteria—Possible Source of Infection in Cancer Patients," Cancer Treatment Reports, vol. 66, No. 3, Mar. 1982, pp. 589-591.

Usami, N. et al., (1999). "A cytochrome P450 enzyme responsible for carbon monoxide formation by cannabidiol in mouse hepatic microsomes" Research Communications in Alcohol and Substances of Abuse 20(1 & 2): 69-77.

Vaddi, H.K., et al., "Human Skin Permeation of Branched-Chain 3-O-Alkyl Ester and Carbonate Prodrugs of Naltrexone" 22(5) Pharmaceutical Research 758-65 (2005).

Valiveti, et al., "LC-MS method for the estimation of D8-THC and 11-nor-D8-THC-9-COOH in plasma" 38(1) J Pharmaceutical and Biomedical Analysis 112-18 (2005).

Valiveti, et al., "In vivo evaluation of 3-O-alky ester transdermal prodrugs of naltrexone in hairless guinea pigs" 102(5) J Controlled Release 509-20 (2005).

Valiveti, et al., "In vitro/In vivo Correlation of Transdermal Naltrexone Prodrugs in Hairless Guinea Pigs" 22(6) Pharmaceutical Research 981-89 (2005).

Van Zadelhoff et al., "With Anandamide As Substrate Plant 5-Lipoxygenases Behave Like 11-Lipoxygenases" Biochemical and Biophysical Research Communications, vol. 248, 1998, pp. 33-38.

Vann, R. E. et al., (2008). "Divergent effects of cannabidiol on the discriminative stimulus and place conditioning effects of Delta(9)-tetrahydrcannabinol" Drug and alcohol dependence 94(1-3): 191-8.

Vinciguerra, V. et al., "Inhalation Marijuana as an Antiemetic for Cancer Chemotherapy," New York State J. Med., Oct. 1988, pp. 525-527.

Wade, D. T. et al., (2004). "Do *cannabis*-based medicinal extracts have general or specific effects on symptoms in multiple sclerosis? A double-blind, randomized, placebo-controlled study on 160 patients" Multiple Sclerosis 10(4): 434-441.

Wade, D. T. et al., (2006). "Long-term use of a cannabis-based medicine in the treatment of spasticity and other symptoms in multiple sclerosis" Multiple sclerosis (Houndmills, Basingstoke, England) 12(5): 639-45.

Waksman et al., "The Central Cannabinoid Receptor (CB1) Mediates Inhibition of Nitric Oxide Production by Rat Microglial Cells," J. Pharmacology Exp. Ther., vol. 288, No. 3, 1999, pp. 1357-1366.

Wang et al., "Stage-Specific Excitation of Cannabinoid Receptor Exhibits Differential Effects on Mouse Embryonic Development," Biology of Reproduction, vol. 60, 1999, pp. 839-844.

Watanabe, K. et al., (1987). "Self-catalyzed inactivation of cytochrome P-450 during microsomal metabolism of cannabidiol" Biochemical Pharmacology 36(20): 3371-7.

Watanabe, K., et al., (1986). "Effects of two cannabinoids on hepatic microsomal cytochrome P-450" J Pharmacobio-Dynamics 9(1): 39-45.

Watanabe, K. et al., (1988). "Formation of similar species to carbon monoxide during hepatic microsomal metabolism of cannabidiol on the basis of spectral interaction with cytochrome P-450" Biochemical Pharmacology 37(24): 4719-26.

Williams et al., "Anandamine Induces Overeating: Mediation by Central Cannabinoid (CB1) Receptors," Psychopharmacology, vol. 143, 1999, pp. 315-317.

Williams, S. J. et al., "Brochodilator Effect on Delta-1-Tetrahydrocannabinol Administered by Aerosol to Asthmatic Patients," Thorax, vol. 31, 1976, pp. 720-723.

Wright, S. et al., (2006). "The use of a *cannabis*-based medicine (Sativex) in the treatment of pain caused by rheumatoid arthritis" Rheumatology (Oxford, England) 45(6): 781; author reply 781.

Wu, T. C. et al., "Pulmonary Hazards of Smoking Marijuana as Compared with Tobacco," New England J. Med., vol. 318, No. 6, 1988, pp. 347-351.

Yamamoto, I. et al., (2003). "Pharmacology and Toxicology of Major Constituents of Marijuana-On the Metabolic Activation of Cannabinoids and Its Mechanism." J Toxicology, Toxin Reviews 22(4): 577-589.

Yamamoto, I. et al, "Recent advances in the metabolism of cannabinoids" 27(8) Int'l J Biochem. and Cell Biology 741-46 (1995).

Yoo, S.D. et al., "Mammary excretion of cannabidiol in rabbits after intravenous administration" J Pharm Pharmacol, 1994. 46(11): p. 926-8.

Yu, C. D. et al:, "Physical Model Evaluation of Topical Prodrug Delivery—Simultaneous Transport and Bioconversion of Vidarabine -5'-valerate I: Physical Model Development," J. Pharmaceutical Sciences, vol. 68, No. 11, Nov. 1979, pp. 1341-1346.

Zhang L et al., (2004) "Restoration of spontaneous exploratory behaviors with an intraecal NMDA receptor antagonist or a PKC inhibitor in rats with acute pancreatitis" Pharmacol Biochem Behav 77: 145-153.

Zimmer A et al., (1999) "Increased mortality, hypoactivity, and hypoalgesia in cannabinoid CB1 receptor knockout mice" Proc Natl Acad Sci USA 96: 5780-5785.

Zimmerman, a.M. et al., "Effects of cannabinoids on sperm morphology" Pharmacology, (1979). 18(3): p. 143-8.

Zimmerman A.M. and Raj A.Y., "Influence of cannabinoids on somatic cells in-vivo" 21(4) Pharmacology 277-87 (1980).

Zuardi, A.W., et al., "Effects of ipsapirone and cannabidiol on human experimental anxiety" J of Psychopharmacology (London, United Kingdom), 1993. 7(1): p. 82-8.

Zuardi, A.W. et al., "Effect of cannabidiol on plasma prolactin, growth hormone and cortisol in human volunteers" Brazilian J of Medical and Biological Research, 1993. 26(2): p. 213-17.

Zuardi, A.W. et al., "Cannabidiol monotherapy for treatment-resistant schizophrenia" J Psychopharmacology (London, United Kingdom), 2006. 20(5): p. 683-686.

Zuardi, A.W. et al., "Action of cannabidiol on the anxiety and other effects produced by delta-9-THC in normal subjects" Psychopharmacology (Berlin, Germany), 1982. 76(3): p. 245-50.

Zuardi, A.W., et al., "Cannabidiol for the treatment of psychosis in Parkinson's disease" European Neuropsychopharmacology, 2008. 18: p. S417-S418.

Zuardi, A., et al., "Cannabidiol was ineffective for manic episode of bipolar affective disorder" J Psychopharmacol, 2008.

Thong, et al, "Percutaneous Penetration Enhancers: An Overview." 20 Skin Pharmacology & Physiology 272-82 (2007).

* cited by examiner

Figure 1. Representative permeation profile of cannabidiol (n=3) and ALL00105 (n=4) in gel formulation
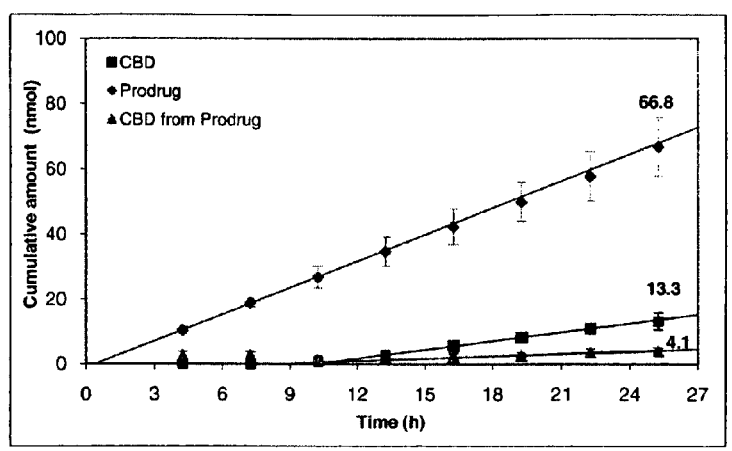
Figure 2. Representative permeation profile of cannabidiol (n=2) and ALL00105 (n=2) in gel formulation
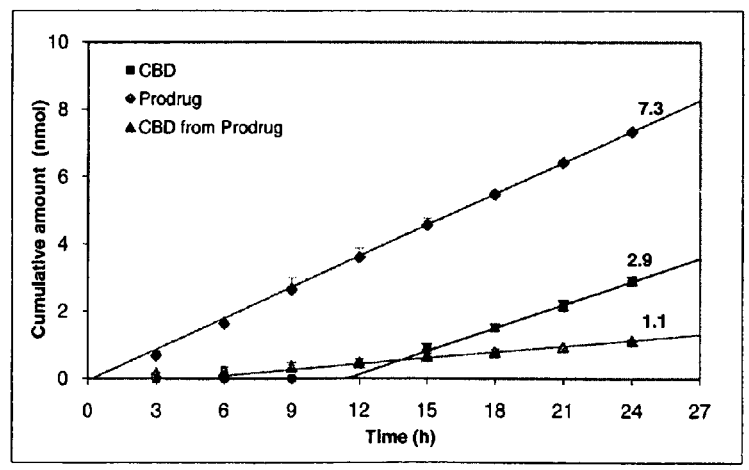

Figure 3. Skin disposition of cannabidiol (n=3) and ALL00101 (n=3) in propylene glycol
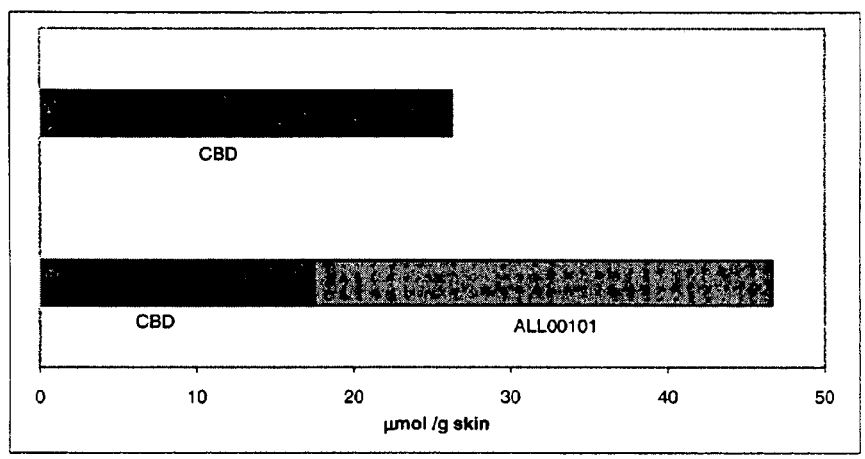
Figure 4. Skin disposition of cannabidiol (n=4) and ALL00102 (n=4) in propylene glycol
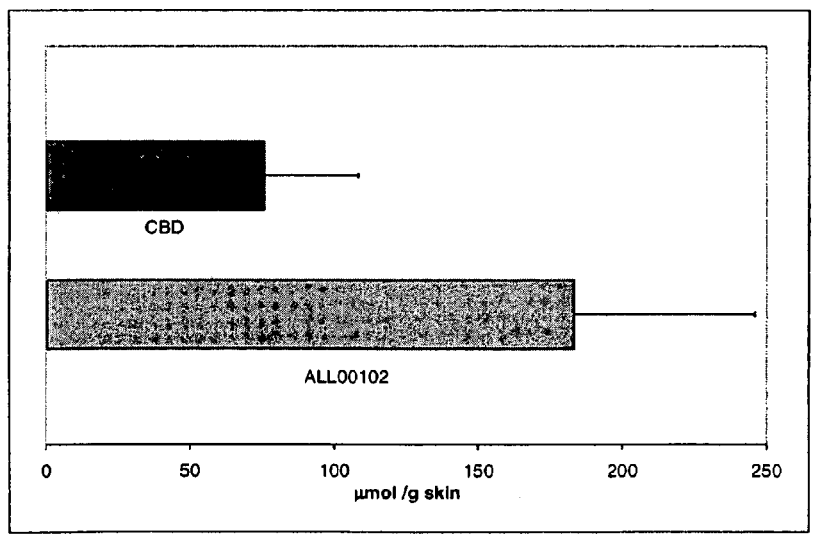

Figure 5. Representative permeation profile of CBD (n=3), ALL00131 (n=3), ALL00132 (n=2), and ALL00140 (n=3) in 90:8:2 PG:H2O:IPM donor solution with 60/40 Hanks'/PEG 400 receiver fluid
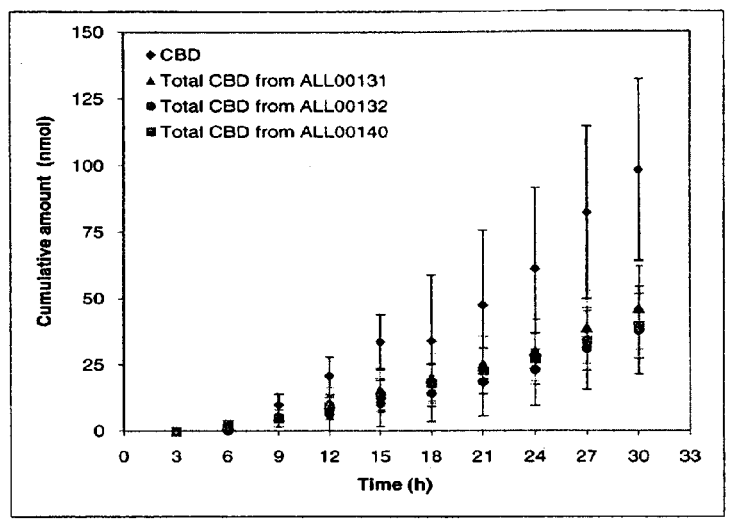
Figure 6. Representative permeation profile of CBD (n=3), ALL00105 (n=1), ALL00145 (n=3), and ALL00147 (n=2) in 90:8:2 PG:H2O:IPM donor solution with 40% aqueous PEG 400 receiver fluid
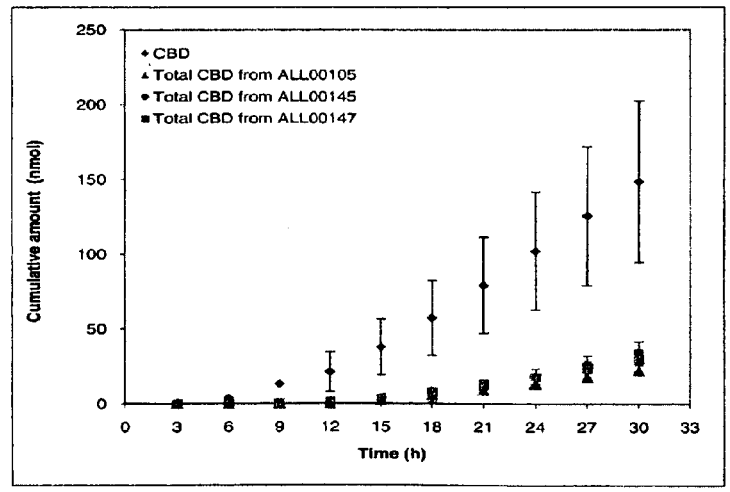

Figure 7. Representative permeation profile of CBD (n=2), ALL00101 (n=2), ALL00146 (n=2), and ALL00148 (n=3) in gel formulation with 40% aqueous PEG 400 receiver fluid
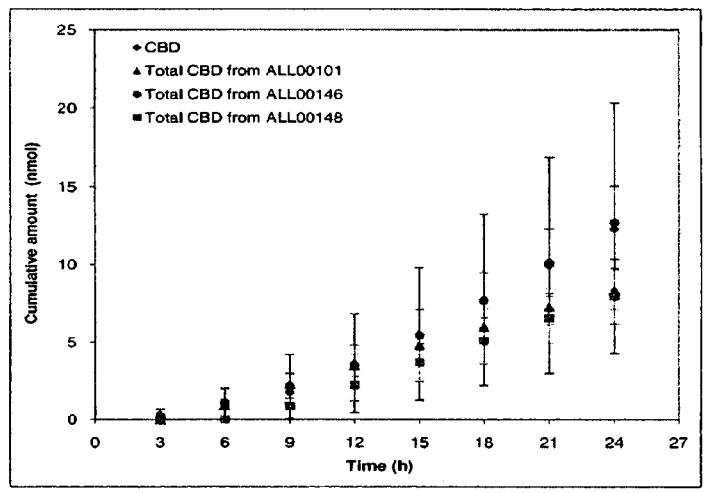
Figure 8. Skin disposition of CBD (n=3), ALL00131 (n=3), ALL00132 (n=2), and ALL00140 (n=3) in 90:8:2 PG:H2O:IPM donor solution with 60/40 Hanks'/PEG 400 receiver fluid
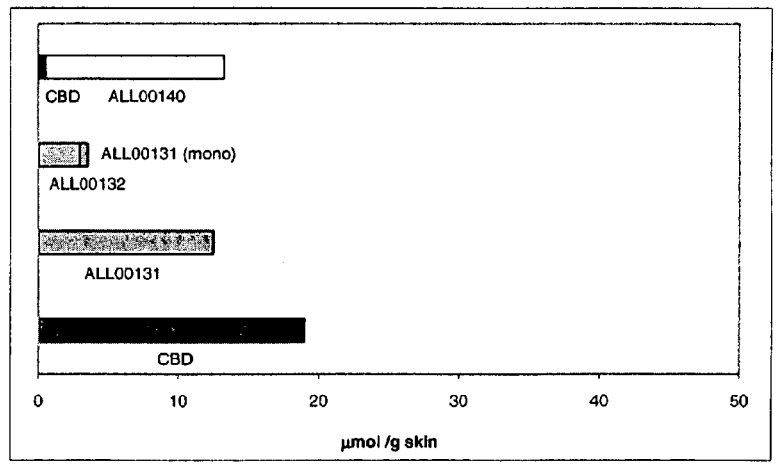

Figure 9 Skin disposition of CBD (n=3), ALL00137 (n=3), ALL00142 (n=3), and ALL00143 (n=3) in 90:8:2 PG:H2O:IPM donor solution with 40% aqueous PEG 400 receiver fluid
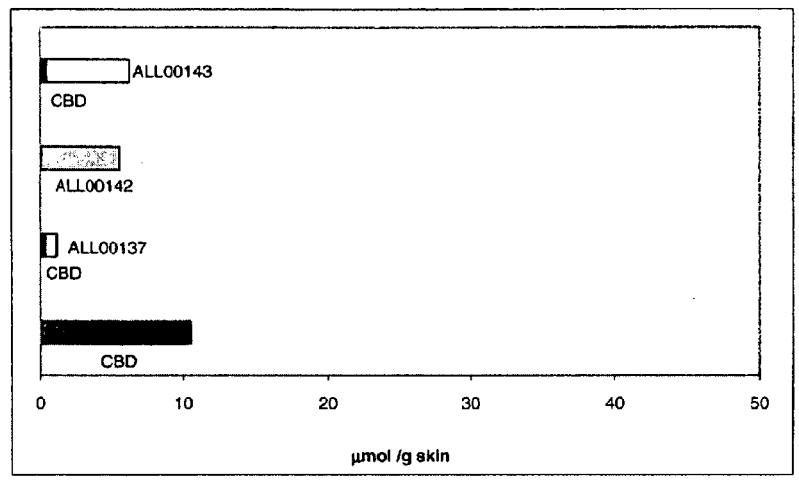
Figure 10. Skin disposition of CBD (n=3), ALL00105 (n=3), ALL00145 (n=3), and ALL00147 (n=2) in 90:8:2 PG:H2O:IPM donor solution with 40% aqueous PEG 400 receiver fluid
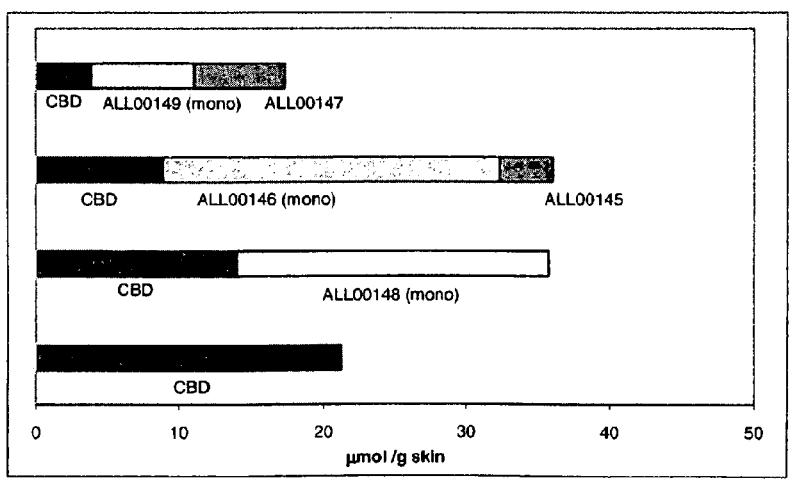

Figure 11  Skin disposition of CBD (n=2), ALL00101 (n=2), ALL00146 (n=2), and ALL00148 (n=3) in gel formulation with 40% aqueous PEG 400 receiver fluid
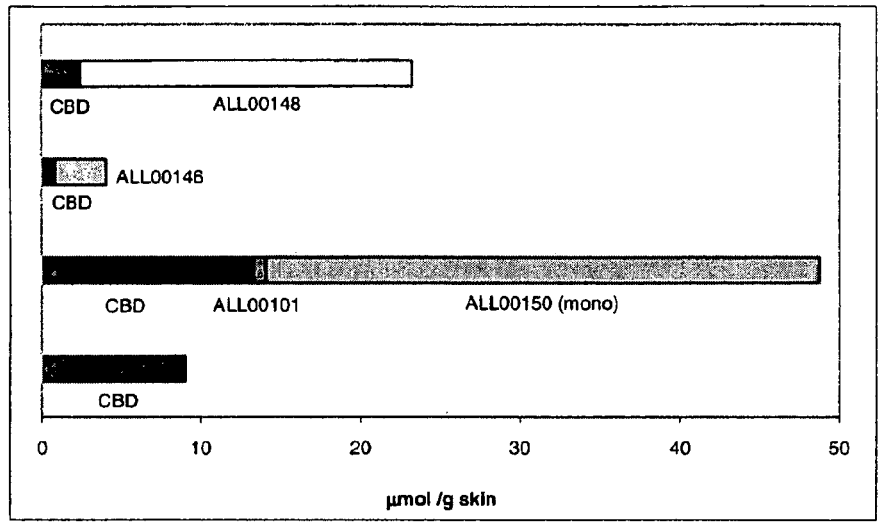
Figure 12.  Representative permeation profile of CBD (n=2), ALL00146 (n=2), and ALL00150 (n=3) in gel formulation with 40% aqueous PEG 400 receiver fluid
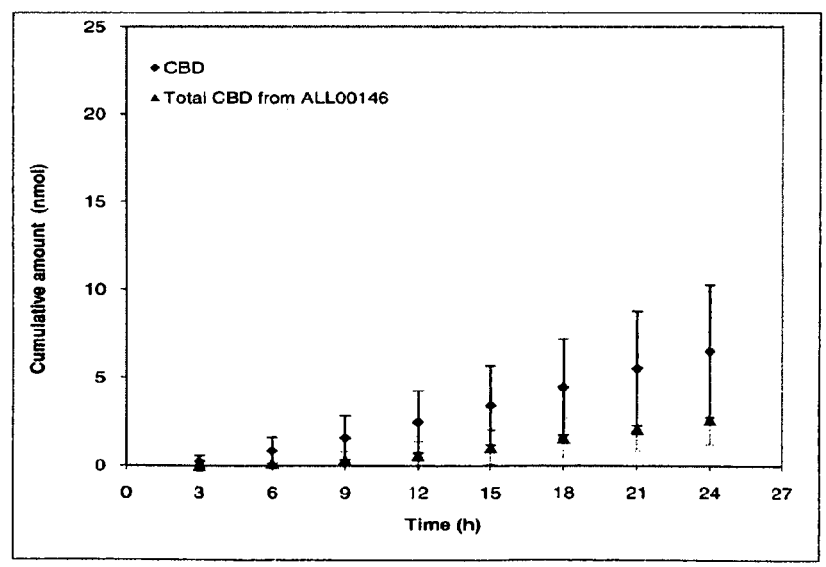

Figure 13. Skin disposition of CBD (n=2), ALL00146 (n=3), and ALL00150 (n=3) in gel formulation with 40% aqueous PEG 400 receiver fluid
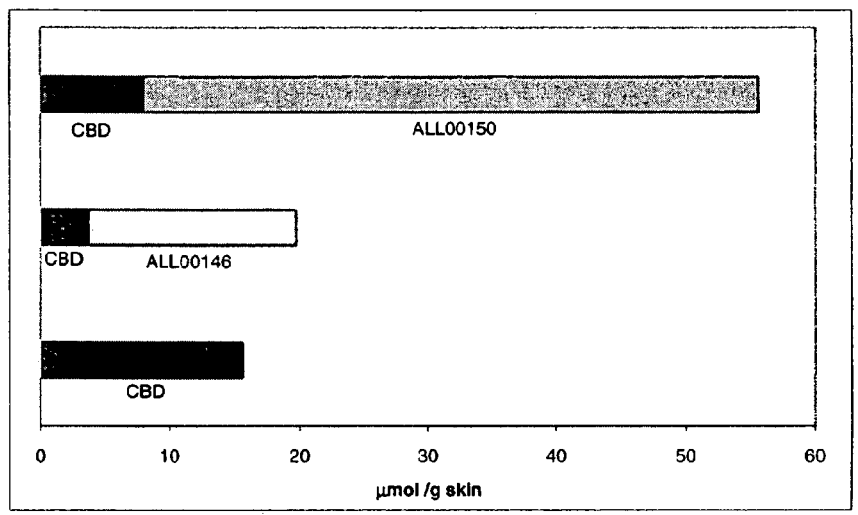
Figure 14. Skin disposition of CBD (n=2) and ALL00150 (n=3) in an anhydrous gel formulation with 40% aqueous PEG 400 receiver fluid
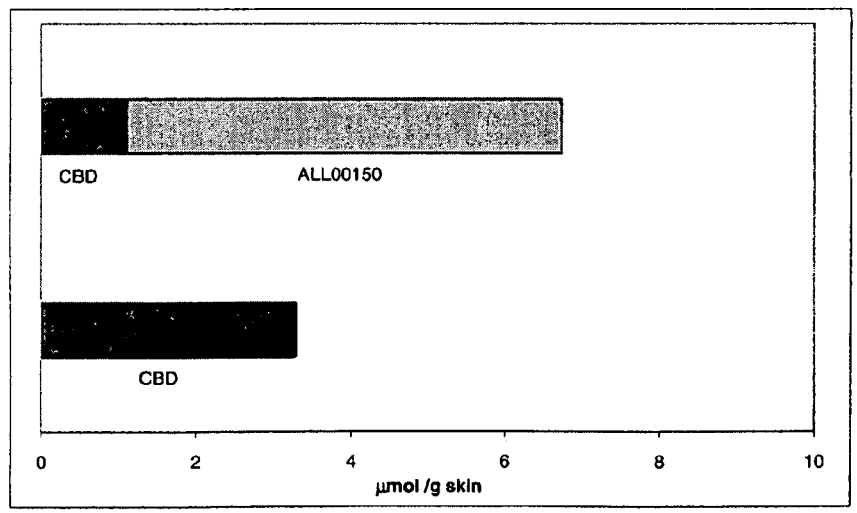

Figure 15. Representative permeation profile of CBD (n=1), ALL00147 (n=1), and ALL00149 (n=1) in gel formulation with 40% aqueous PEG 400 receiver fluid
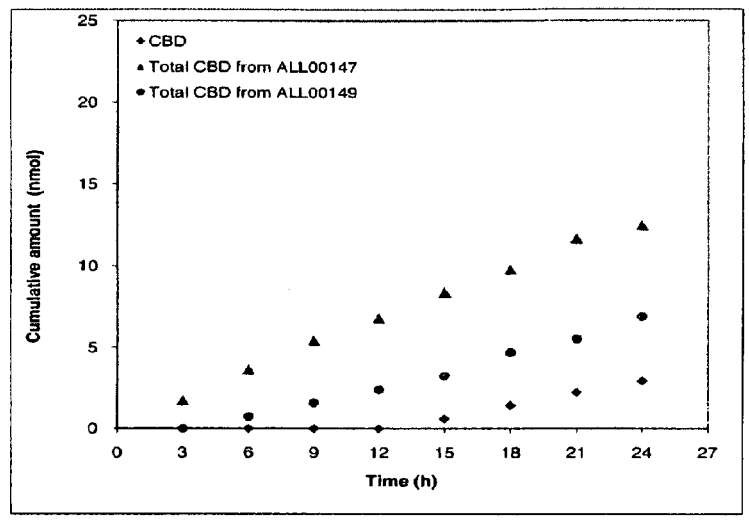
Figure 16. Skin disposition of CBD (n=3), ALL00147 (n=3), and ALL00149 (n=3) in gel formulation with 40% aqueous PEG 400 receiver fluid
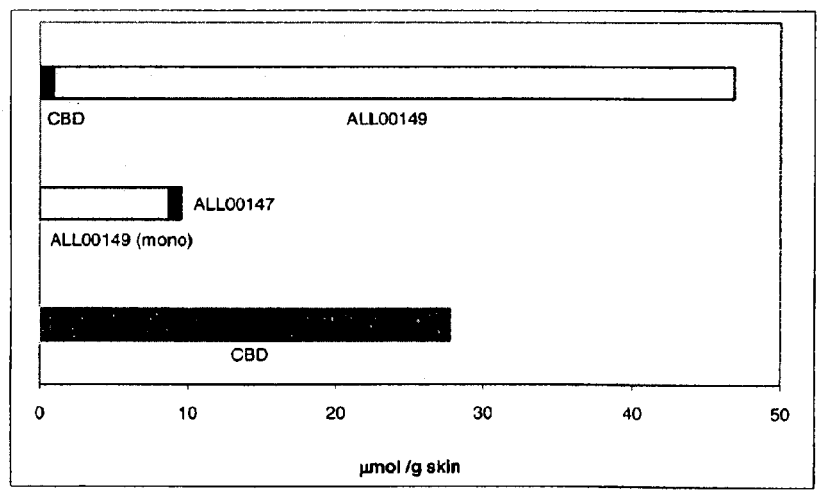

PRODRUGS OF CANNABIDIOL, COMPOSITIONS COMPRISING PRODRUGS OF CANNABIDIOL AND METHODS OF USING THE SAME

CROSS-REFERENCE TO RELATED APPLICATIONS

This application claims the benefit of U.S. Provisional Application Ser. No. 60/952,746 filed on Jul. 30, 2007 and is hereby incorporated by reference.

FIELD

Described herein are pharmaceutically active agents (e.g., prodrugs of cannabidiol) suitable for local and systemic delivery to a mammal, including systemic transdermal delivery and topical delivery; compositions for delivering pharmaceutically active agents both systemically and locally; and the use of such compositions in treating and preventing diseases and disorders, as well as improving cosmetic appearance.

BACKGROUND

The clinical usefulness of the cannabinoids, including cannabidiol ("CBD"), to provide analgesia and neuroprotection, reduce inflammation, help alleviate nausea and emesis, as well as treat epilepsy, anxiety disorders, and glaucoma, has been well-recognized. In addition, it is also well-known that cannabidiol lacks the psychoactive effects seen in many of the other cannabinoids, including $\Delta^9$-tetrahydrocannabinol, which is currently available in an oral dosage, sold under the trade name Marinol®.

Pain is the most frequently reported symptom and it is a common clinical problem which confronts the clinician. Millions of people in the USA suffer from severe pain that, according to numerous recent reports, is chronically under-treated or inappropriately managed. Similarly, millions of people also suffer from severe nausea and/or frequent emesis. Moreover, all too frequently, many patients suffering from chronic, under-treated or unretractable pain also suffer from lack of appetite, nausea and/or frequent emesis, such that a patient is unable to receive effective therapeutic doses of oral pain medications, thereby exacerbating their pain. Cannabinoids, including cannabidiol, are effective in alleviating pain. Moreover, cannabinoids, including cannabidiol, can reduce a patient's nausea and vomiting, independent of any pain relief achieved. Thus cannabinoids are particularly useful in patients experiencing nausea and vomiting secondarily to un- or under-treated pain.

A notable percentage of the U.S. population satisfy the diagnostic criteria for alcohol use disorders ("AUDs"). The consumption of excessive amounts of alcohol results in a complex array of pharmacological effects that directly impact the ability to treat the condition. These effects directly impact the brain and include progressive neurodegeneration, impaired executive function and dependence leading to withdrawal-induced negative effects. It is known that the cannabinoids, including cannabidiol, have neuroprotective, anxiolytic and anti-convulsant effects, which may be effective in preventing additional brain damage in persons with AUDs, while simultaneously decreasing the frequency of relapses.

Dystonia is a neurological movement disorder, with many known causes, and characterized by involuntary, continual muscular contractions causing twisting and repetitive movements or abnormal postures. Cannabinoids have been shown to reduce the symptoms of muscular contractions characterizing this disorder.

The etiological pathology of many diseases relates to the inflammatory processes caused by an individual's immune system. The inflammation may result from (1) an otherwise appropriate immunoresponse to an outside trauma, such as brain swelling secondary to a closed head injury; (2) an overactive immunoresponse such as with an allergic reaction or dermatitis; or (3) an inappropriate auto-immunoresponse such as what causes certain forms of multiple sclerosis, inflammatory bowel disorders and arthritis. Regardless of the underlying cause of the inflammation, it is therapeutically desirable under these circumstances to regulate the immune system and lessen the inflammatory response. Cannabinoids have been shown to regulate various steps in the immune response and could show some therapeutic benefit in treatment of certain inflammatory diseases such as psoriatic arthritis.

Rheumatoid arthritis affects approximately 0.5-1% of the United States population, and autoimmune diseases in general affect more than 20 million Americans. The pain associated with rheumatoid arthritis can often be disabling. Cannabinoids have been found to be useful as adjunct treatment for rheumatoid arthritis and joint pain secondary to other autoimmune diseases, such as inflammatory bowel disease, multiple sclerosis and systemic lupus erythematosus.

In addition to the above-discussed therapeutics benefits, cannabinoids, cannabidiol, and cannabidiol prodrugs present a variety of pharmacological benefits, including, but not limited to, anti-inflammatory, anti-convulsant, anti-psychotic, anti-oxidant, neuroprotective anti-cancer and immunomodulatory effects.

Given these systemic therapeutic benefits, it would be advantageous to develop a composition in which cannabidiol is delivered to achieve a therapeutically effective concentration in a patient. Unfortunately, as with the other cannabinoids, cannabidiol undergoes substantial first-pass metabolism when absorbed from the human gut after oral administration. Further, the oral bioavailability of any product is further diminished when a patient suffers from nausea or emesis, as either they avoid taking their oral medication or the oral dosage form does not remain in the GI tract for a sufficient amount of time to achieve a therapeutic dose.

Therefore, in view of the foregoing, it would be desirable to deliver therapeutically effective amounts of cannabidiol to a mammal in need thereof for the treatment of one or more medical conditions, such as pain, nausea or appetite stimulation, by a route of administration that does not depend upon absorption from the gastrointestinal tract of the mammal and not subject to first-pass metabolism upon absorption from the gastrointestinal tract. One non-oral route of administration for the systemic delivery of cannabidiol is transdermal.

Unfortunately, due to its highly hydrophobic nature, cannabidiol is poorly absorbed through membranes such as the skin of a mammal, such as a human. Therefore, the success of transdermally administering therapeutically effective quantities of cannabidiol to a mammal in need of such treatment within a reasonable time frame and over a suitable surface area has been substantially limited.

However, the epidermis and dermis of many mammals, such as humans and guinea pigs, contains enzymes which are capable of metabolizing active pharmaceutical agents which pass through the stratum corneum. The metabolic process occurring in the skin of mammals, such as humans, can be utilized to deliver pharmaceutically effective quantities of cannanbidiol to the systemic circulation of a mammal in need thereof. Described herein are prodrugs of cannabidiol that can be transdermally administered to a mammal, such as a human, so that the metabolic product resulting from metabolism in the skin is cannabidiol which is systemically available for the treatment of a medical condition such as pain, nausea or appetite stimulation. Also described herein are compositions comprising cannabidiol prodrugs suitable for transdermal delivery to a mammal in need thereof and methods of using cannabidiol prodrugs.

Therefore, a significant advancement in the art would occur with the development of a cannabidiol prodrug capable of transdermal delivery; compositions suitable for transdermal delivery comprising prodrugs of cannabidiol; and methods of using prodrugs of cannabidiol whereby the resulting metabolic product was cannabidiol which is locally or systemically available to a mammal in a therapeutically effective amount.

In addition, pharmaceutical compositions can be systemically administered by other means, including: oral, buccal, sublingual, injection, rectal, vaginal and intranasal. The metabolic process occurring in mammals, such as humans, can also be utilized to deliver pharmaceutically effective quantities of cannabidiol to the systemic circulation of a mammal in need thereof. Described herein are prodrugs of cannabidiol that can be administered to a mammal, such as a human, so that the metabolic product resulting from metabolism in the skin is cannabidiol which is available for the treatment of a medical condition such as pain, nausea or appetite stimulation. Also described herein are compositions comprising cannabidiol prodrugs suitable for delivery to a mammal in need thereof and methods of using cannabidiol prodrugs.

Therefore, a significant advancement in the art would occur if one could develop a prodrug of cannabidiol capable of oral, buccal, sublingual, injectable, topical, follicular, nasal, ocular, rectal or vaginal delivery; compositions suitable for oral, buccal, sublingual, injectable, topical, follicular, nasal, ocular, rectal, vaginal delivery comprising prodrugs of cannabidiol; and methods of using prodrugs of cannabidiol whereby the resulting metabolic product was cannabidiol which is systemically available to a mammal in a therapeutically effective amount.

In addition to the benefits of systemically administered cannabidiol discussed above, cannabinoids, including cannabidiol, have been found to have localized benefits from topical administration. For example, topically administered cannabinoids have been found to be useful to alleviate pain and other conditions originating near the surface of the skin, including but not limited to pain associated with post-herpetic neuralgia, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis and psoriatic arthritis. In addition, topically administered cannabinoids have been found to be useful to alleviate pain and other conditions associated with deeper tissues, such as peripheral neuropathic pain, including but not limited to the peripheral neuropathic pain associated with diabetic neuropathy, ankylosing spondylitis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, synovitis, and juvenile rheumatoid arthritis. When cannabinoids are administered topically to treat pain and other conditions associated with deeper tissues, including peripheral neuropathic pain, it may be useful to co-administer cannabinoids systemically. Also, it has been found that the topical administration of cannabinoids, including cannabidiol, can inhibit the growth of hair.

In order to achieve these local benefits, it is advantageous for cannabidiol or a prodrug thereof to penetrate the stratum corneum but not be absorbed systemically. In such a case, the cannabidiol would concentrate in the skin and/or pilosebaceous unit, thus maximizing its local effect. Not only does the localized effect increase the potential therapeutic benefit, it lessens the frequency and severity of side-effects associated with cannabinoid administration because the amount of active compound circulating in the patient is minimized. The cannabidiol can be incorporated into a prodrug with an active moiety that would improve the appearance and/or hydration of the skin.

Therefore, a significant advancement in the art would occur with the development of a cannabidiol prodrug capable of topical delivery, such that it penetrates the outer layer of the skin but is not absorbed into circulation; compositions suitable for topical delivery comprising prodrugs of cannabidiol and methods of using prodrugs of cannabidiol whereby the resulting metabolic product was cannabidiol which is available at the site of administration in a mammal in a therapeutically effective amount but is not absorbed systemically.

SUMMARY

Described herein are prodrugs of cannabidiol, methods of making prodrugs of cannabidiol, compositions comprising prodrugs of cannabidiol and methods of using prodrugs of cannabidiol.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

BRIEF DESCRIPTION OF THE DRAWINGS

FIG. 1 is a line graph illustrating the representative permeation profile of cannabidiol (n=3) and ALL00105 (n=4) in a gel formulation, wherein "n" is the number of skin samples tested.

FIG. 2 is a line graph illustrating the representative permeation profile of cannabidiol (n=2) and ALL00105 (n=2) in a gel formulation, wherein "n" is the number of skin samples tested.

FIG. 3 is a bar graph illustrating the skin disposition of cannabidiol (n=3) and ALL00101 (n=3) in propylene glycol, wherein "n" is the number of skin samples tested.

FIG. 4 is a bar graph illustrating the skin disposition of cannabidiol (n=4) and ALL00102 (n=4) in propylene glycol, wherein "n" is the number of skin samples tested.

FIG. 5 is a graph illustrating the permeation profile of CBD (n=3), ALL00131 (n=3), ALL00132 (n=2), and ALL00140 (n=3), wherein "n" is the number of skin samples tested.

FIG. 6 is a graph illustrating the permeation profile of CBD (n=3), ALL00105 (n=1), ALL00145 (n=3) and ALL00147

(n=2) in 90:8:2 PG:H2O:IPM donor solution with 40% aqueous PEG 400 receiver fluid, wherein "n" is the number of skin samples tested.

FIG. 7 is a graph illustrating the permeation profile of CBD (n=2), ALL00101 (n=2), ALL00146 (n=2) and ALL00148 (n=3) in gel formulation with 40% aqueous PEG 400 receiver fluid, wherein "n" is the number of skin samples tested.

FIG. 8 is a bar graph illustrating the skin disposition of CBD (n=3), ALL00131 (n=3), ALL00132 (n=2), and ALL00140 (n=3) in 90:8:2 PG:H2O:IPM donor solution with 60/40 Hanks'/PEG 400 receiver fluid, wherein "n" is the number of skin samples tested.

FIG. 9 is a bar graph illustrating the skin disposition of CBD (n=3), ALL00137 (n=3), ALL00142 (n=3), and ALL00143 (n=3) in 90:8:2 PG:H2O:IPM donor solution with 40% aqueous PEG 400 receiver fluid, wherein "n" is the number of skin samples tested.

FIG. 10 is a bar graph illustrating the skin disposition of CBD (n=3), ALL00105 (n=3), ALL00145 (n=3), and ALL00147 (n=2) in 90:8:2 PG:H2O:IPM donor solution with 40% aqueous PEG 400 receiver fluid, wherein "n" is the number of skin samples tested.

FIG. 11 is a bar graph illustrating the skin disposition of CBD (n=2), ALL00101 (n=2), ALL00146 (n=2), and ALL00148 (n=3) in gel formulation with 40% aqueous PEG 400 receiver fluid, wherein "n" is the number of skin samples tested.

FIG. 12 is a graph illustrating the permeation profile of CBD (n=2), ALL00146 (n=2), and ALL00150 (n=3) in gel formulation with 40% aqueous PEG 400 receiver fluid, wherein "n" is the number of skin samples tested.

FIG. 13 is a bar graph illustrating the skin disposition of CBD (n=2), ALL00146 (n=3), and ALL00150 (n=3) in gel formulation with 40% aqueous PEG 400 receiver fluid, wherein "n" is the number of skin samples tested.

FIG. 14 is a bar graph illustrating the skin disposition of CBD (n=2) and ALL00150 (n=3) in an anhydrous gel formulation with 40% aqueous PEG 400 receiver fluid, wherein "n" is the number of skin samples tested.

FIG. 15 shows a representative permeation profile of CBD (n=1), ALL00147 (n=1), and ALL00149 (n=1) in gel formulation with 40% aqueous PEG 400 receiver fluid.

FIG. 16 shows the skin disposition of CBD (n=3), ALL00147 (n=3), and ALL00149 (n=3) in gel formulation with 40% aqueous PEG 400 receiver fluid.

DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Compounds described herein include pharmaceutically acceptable prodrugs of cannabidiol. One embodiment described herein includes pharmaceutically acceptable prodrugs of cannabidiol which are suitable for non-oral administration and are metabolized to cannabidiol. A further embodiment described herein includes pharmaceutically acceptable prodrugs of cannabidiol which are suitable for transdermal administration and are metabolized to cannabidiol. The pharmaceutically acceptable prodrugs of cannabidiol may be in any suitable form for administration to a mammal such as in the form of a free base, free acid, salt, hydrate, anhydrate, enantiomer, isomer, tautomer, polymorph, derivative, or the like, provided that the free base, salt, hydrate, enantiomer, isomer, tautomer, or any other pharmacologically suitable derivative is therapeutically active or undergoes conversion within or outside of the body to a therapeutically active form of cannabidiol.

Compositions described herein comprise at least one pharmaceutically acceptable prodrug of cannabidiol and are suitable for transdermal, oral, buccal, sublingual, injectable, topical, follicular, nasal, ocular, rectal or vaginal administration. The compositions described herein optionally include a vehicle or carrier for the administration of a prodrug of cannabidiol as well as optionally including pharmaceutically acceptable excipients such as solvents, thickening agents, penetration enhancers, wetting agents, lubricants, emollients, binders, taste enhancers, disintegrates, substances added to mask or counteract a disagreeable odor, fragrances or tastes, and substances added to improve appearance or texture of the composition.

The term prodrug as used herein refers to a compound that undergoes a chemical conversion, through a metabolic process or otherwise within the body of the mammal receiving the compound, into its active form that has medical effects.

In one embodiment, illustrative cannabidiol prodrugs include those compounds of Formula (I):

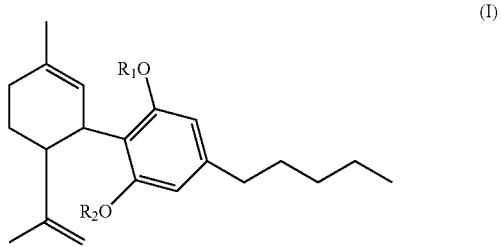

(I)

wherein $R_1$ and $R_2$ can be the same or different and are each independently comprised of a hydrogen and/or a bio-labile linker (e.g. ester, oxygenated ester, oxaester, pegylated ester, hydroxylated ester, alkyl ester, amino ester, alkylamino ester, dialkylamino ester, carbonate, alkyl carbonate, carbamate, alkyl carbamate, amino carbamate, alkylamino carbamate, dialkylamino carbamate, or other suitable bio-labile linking structure) and further comprising moieties which can be selected in order to control the rate and extent of absorption and metabolism, including transdermal absorption and metabolism. However, $R_1$ and $R_2$ cannot both be a hydrogen atom. Several options for $R_1$ and $R_2$ are disclosed herein. Also included herein is the free base, salt, ester, hydrate, amide, enantiomer, isomer, tautomer, polymorph, or derivative thereof of compounds of Formula I.

Additional embodiments contemplated by the present disclosure include, but are not limited to, those described in WO2007044215, WO2007035945, US2007066657, WO2007026215, WO2007020502, WO2007017264, WO2007009720, US2007004772, US2006287324, US2006287323, US2006287342, US2006287341, US2006089378, US2006079556, US2005143441, U.S. Pat. No. 7,109,216, US2004235854, US2005267161, US2005054659, US2007099990, US2006122229, US2006122230, US2004077650, U.S. Pat. No. 6,974,810, US2004248944, U.S. Pat. No. 6,977,266 and US2006052411 and U.S. patent application Ser. No. 10/032,163.

"Pharmaceutically acceptable salts," or "salts," include the salt of a cannabidiol prodrug suitable for administration to a mammal and includes those prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, algenic, beta-hydroxybutyric, galactaric and galacturonic acids. The following list of pharmaceutically acceptable salts is not meant to be exhaustive but merely illustrative as person of ordinary skill in the art would appreciate that other pharmaceutically acceptable salts of cannabidiol and prodrugs of cannabidiol may be prepared.

In one embodiment, acid addition salts are prepared from the free base forms using conventional methodology involving reaction of the free base with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. The following list of organic and inorganic acids is not meant to be exhaustive but merely illustrative as person of ordinary skill in the art would appreciate that other acids may be used to create pharmaceutically acceptable salts of cannabidiol and prodrugs of cannabidiol. In other embodiments, an acid addition salt is reconverted to the free base by treatment with a suitable base. In still other embodiments, the basic salts are alkali metal salts, e.g., sodium salt.

In one embodiment, $R_1$ or $R_2$ is an ester. In a further embodiment both $R_1$ and $R_2$ are esters which can be the same or different. The preparation of CBD esters involves functionalizing the hydroxyl groups that are present within the molecular structure of cannabidiol. In another embodiment, the esters of either or both of $R_1$ and/or $R_2$ are oxygenated. In another embodiment, either or both of $R_1$ and/or $R_2$ are oxygenated esters which are oxaesters. In another embodiment, either or both of $R_1$ and/or $R_2$ are oxaesters which are pegylated. In further embodiments, either or both of $R_1$ and/or $R_2$ are pegylated oxaesters can independently have 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units, 8 ethylene glycol repeat units, 9 ethylene glycol repeat units, 10 ethylene glycol repeat units, 11 ethylene glycol repeat units, 12 ethylene glycol repeat units, 13 ethylene glycol repeat units, 14 ethylene glycol repeat units and 15 ethylene glycol repeat units. In a further embodiment, either or both of $R_1$ and/or $R_2$ are esters which are hydroxylated. In a further embodiment, either or both of $R_1$ and/or $R_2$ are esters which are alkyl ester. In additional embodiments, either or both of $R_1$ and/or $R_2$ are alkyl esters independently having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, 14 alkyl carbons and 15 alkyl carbons. In other embodiments, either or both of $R_1$ and/or $R_2$ are esters which are amino esters independently having 1 amino group, 2 amino groups, 3 amino groups, 4 amino groups and 5 amino groups. In another embodiment, either or both of $R_1$ and/or $R_2$ are amino esters which are alkylamino ester. In a further embodiment, either or both of $R_1$ and/or $R_2$ are alkylamino esters independently having 1 amino group, 2 amino groups, 3 amino groups, 4 amino groups and 5 amino groups and independently having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, 14 alkyl carbons and 15 alkyl carbons. In another embodiment the ester is a glycolic acid ester. In another embodiment the ester is a glycolic acid ester, a hyluronic ester or a lactic acid ester. Esters can be reconverted to the free acids, if desired, by using conventional procedures such as hydrogenolysis or hydrolysis.

In one embodiment, $R_1$ or $R_2$ is a carbamate. In a further embodiment both $R_1$ and $R_2$ are carbamates which can be the same or different. The preparation of CBD carbamates involves functionalizing the hydroxyl groups that are present within the molecular structure of cannabidiol. In another embodiment, the carbamates of either or both of $R_1$ and/or $R_2$ are oxygenated. In another embodiment, either or both of $R_1$ and/or $R_2$ are oxygenated carbamates which are oxacarbamates. In another embodiment, either or both of $R_1$ and/or $R_2$ are oxacarbamates which are pegylated. In further embodiments, either or both of $R_1$ and/or $R_2$ are pegylated oxacarbamates can independently have 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units, 8 ethylene glycol repeat units, 9 ethylene glycol repeat units, 10 ethylene glycol repeat units, 11 ethylene glycol repeat units, 12 ethylene glycol repeat units, 13 ethylene glycol repeat units, 14 ethylene glycol repeat units and 15 ethylene glycol repeat units. In a further embodiment, either or both of $R_1$ and/or $R_2$ are carbamates which are hydroxylated. In a further embodiment, either or both of $R_1$ and/or $R_2$ are carbamates which are alkyl carbamates. In additional embodiments, either or both of $R_1$ and/or $R_2$ are alkyl carbamates independently having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, 14 alkyl carbons and 15 alkyl carbons. In other embodiments, either or both of $R_1$ and/or $R_2$ are carbamates which are amino carbamates independently having 1 amino group, 2 amino groups, 3 amino groups, 4 amino groups and 5 amino groups. In another embodiment, either or both of $R_1$ and/or $R_2$ are amino carbamates which are alkylamino carbamates. In a further embodiment, either or both of $R_1$ and/or $R_2$ are alkylamino carbamates independently having 1 amino group, 2 amino groups, 3 amino groups, 4 amino groups and 5 amino groups and independently having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, 14 alkyl carbons and 15 alkyl carbons. In another embodiment the carbamate is a glycolic acid carbamate, a hyluronic carbamate or a lactic acid carbamate. Carbamates can be reconverted to the free acids, if desired, by using conventional procedures such as hydrogenolysis or hydrolysis.

In one embodiment, $R_1$ or $R_2$ is a carbonate. In a further embodiment both $R_1$ and $R_2$ are carbonates which can be the same or different. The preparation of CBD carbonates involves functionalizing the hydroxyl groups that are present within the molecular structure of cannabidiol. In another embodiment, the carbonates of either or both of $R_1$ and/or $R_2$ are oxygenated. In another embodiment, either or both of $R_1$ and/or $R_2$ are oxygenated carbonates which are oxacarbonates. In another embodiment, either or both of $R_1$ and/or $R_2$ are oxacarbonates which are pegylated. In further embodiments, either or both of $R_1$ and/or $R_2$ are pegylated oxacarbonates can independently have 1 ethylene glycol repeat unit, 2 ethylene glycol repeat units, 3 ethylene glycol repeat units, 4 ethylene glycol repeat units, 5 ethylene glycol repeat units, 6 ethylene glycol repeat units, 7 ethylene glycol repeat units, 8 ethylene glycol repeat units, 9 ethylene glycol repeat units, 10 ethylene glycol repeat units, 11 ethylene glycol repeat units, 12 ethylene glycol repeat units, 13 ethylene glycol repeat units, 14 ethylene glycol repeat units and 15 ethylene glycol repeat units. In a further embodiment, either or both of $R_1$ and/or $R_2$ are carbonates which are hydroxylated. In a further embodiment, either or both of $R_1$ and/or $R_2$ are carbonates which are alkyl carbonates. In additional embodiments, either or both of $R_1$ and/or $R_2$ are alkyl carbonates independently having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, 14 alkyl carbons and 15 alkyl carbons. In other embodiments, either or both of $R_1$ and/or $R_2$ are carbonates which are amino carbonates independently having 1 amino group, 2 amino groups, 3 amino groups, 4 amino groups and 5 amino groups. In another embodiment, either or both of $R_1$ and/or $R_2$ are amino carbonates which are alkylamino carbonates. In a further embodiment, either or both of $R_1$ and/or $R_2$ are alkylamino carbonates independently having 1 amino group, 2 amino groups, 3 amino groups, 4 amino groups and 5 amino groups and independently having 1 alkyl carbon, 2 alkyl carbons, 3 alkyl carbons, 4 alkyl carbons, 5 alkyl carbons, 6 alkyl carbons, 7 alkyl carbons, 8 alkyl carbons, 9 alkyl carbons, 10 alkyl carbons, 11 alkyl carbons, 12 alkyl carbons, 13 alkyl carbons, 14 alkyl carbons and 15 alkyl carbons. In another embodiment the carbonate is a glycolic acid carbonate, a hyluronic carbonate or a lactic acid carbonate. Carbonates can be reconverted to the free acids, if desired, by using conventional procedures such as hydrogenolysis or hydrolysis.

Further embodiments described herein are pharmaceutical compositions comprising:
(a) a cannabidiol prodrug selected from the group consisting of:

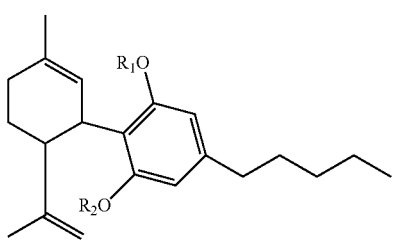

wherein $R_1$ and $R_2$ are independently selected from hydrogen, ester, oxygenated ester, oxaester, pegylated ester, hydroxylated ester, alkyl ester, amino ester, alkylamino ester, dialkylamino ester, glycolic acid ester, hyaluronic acid ester, lactic acid ester, carbonate, oxygenated carbonate, oxacarbonate, pegylated carbonate, hydroxylated carbonate, alkyl carbonate, amino carbonate, alkylamino carbonate, dialkylamino carbonate, glycolic acid carbonate, hyaluronic acid carbonate, lactic acid carbonate, carbamate, oxygenated carbamate, oxacarbamate, pegylated carbamate, hydroxylated carbamate, alkyl carbamate, amino carbamate, alkylamino carbamate, dialkylamino carbamate, glycolic acid carbamate, hyaluronic acid carbamate and lactic acid carbamate; and
wherein $R_1$ and $R_2$ can not both be hydrogen; and
(b) a pharmaceutical excipient.

A method of administering a compound to a mammal comprising the steps of:
(a) combining a compound selected from the group consisting of:

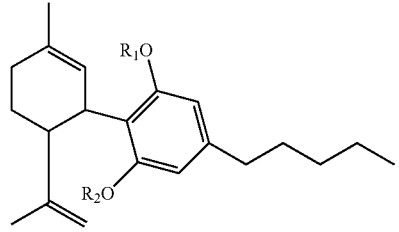

wherein $R_1$ and $R_2$ are independently selected from hydrogen, ester, oxygenated ester, oxaester, pegylated ester, hydroxylated ester, alkyl ester, amino ester, alkylamino ester, dialkylamino ester, glycolic acid ester, hyaluronic acid ester, lactic acid ester, carbonate, oxygenated carbonate, oxacarbonate, pegylated carbonate, hydroxylated carbonate, alkyl carbonate, amino carbonate, alkylamino carbonate, dialkylamino carbonate, glycolic acid carbonate, hyaluronic acid carbonate, lactic acid carbonate, carbamate, oxygenated carbamate, oxacarbamate, pegylated carbamate, hydroxylated carbamate, alkyl carbamate, amino carbamate, alkylamino carbamate, dialkylamino carbamate, glycolic acid carbamate, hyaluronic acid carbamate and lactic acid carbamate; and
wherein $R_1$ and $R_2$ can not both be hydrogen;
with a pharmaceutical excipient to form a pharmaceutical composition;
(b) creating a dosage form suitable for administration to a mammal from the pharmaceutical composition; and
(c) administering the dosage form to a mammal.

Additional embodiments include methods of transdermally delivering a cannabidiol to a mammal comprising the steps of:
(a) selecting a cannabidiol prodrug from the group consisting of:

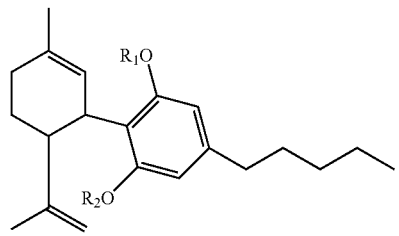

wherein $R_1$ and $R_2$ are independently selected from hydrogen, ester, oxygenated ester, oxaester, pegylated ester, hydroxylated ester, alkyl ester, amino ester, alkylamino ester, dialkylamino ester, glycolic acid ester, hyaluronic acid ester, lactic acid ester, carbonate, oxygenated carbonate, oxacarbonate, pegylated carbonate, hydroxylated carbonate, alkyl carbonate, amino carbonate, alkylamino carbonate, dialkylamino carbonate, glycolic acid carbonate, hyaluronic acid carbonate, lactic acid carbonate, carbamate, oxygenated carbamate, oxacarbamate, pegylated carbamate, hydroxylated carbamate, alkyl carbamate, amino carbamate, alkylamino carbamate, dialkylamino carbamate, glycolic acid carbamate, hyaluronic acid carbamate and lactic acid carbamate; and
wherein $R_1$ and $R_2$ can not both be hydrogen.
(b) combining the selected cannabidiol prodrug with a pharmaceutically acceptable excipient to form a pharmaceutical composition; and
(c) contacting the pharmaceutical composition with the skin of a mammal.

A further embodiment described herein is a method of treating a medical condition in a mammal comprising the steps of administering a cannabidiol prodrug selected from the group consisting of:

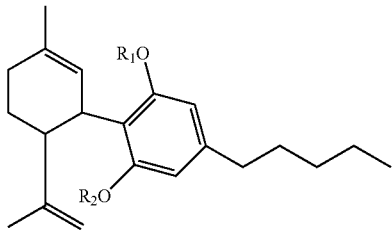

wherein $R_1$ and $R_2$ are independently selected from hydrogen, ester, oxygenated ester, oxaester, pegylated ester, hydroxylated ester, alkyl ester, amino ester, alkylamino ester, dialkylamino ester, glycolic acid ester, hyaluronic acid ester, lactic acid ester, carbonate, oxygenated carbonate, oxacarbonate, pegylated carbonate, hydroxylated carbonate, alkyl carbonate, amino carbonate, alkylamino carbonate, dialkylamino carbonate, glycolic acid carbonate, hyaluronic acid carbonate, lactic acid carbonate, carbamate, oxygenated carbamate, oxacarbamate, pegylated carbamate, hydroxylated carbamate, alkyl carbamate, amino carbamate, alkylamino carbamate, dialkylamino carbamate, glycolic acid carbamate, hyaluronic acid carbamate and lactic acid carbamate;
wherein $R_1$ and $R_2$ can not both be hydrogen; and
wherein the medical condition is selected from the group consisting of: nausea, emesis, pain, wasting syndrome, HIV-wasting, chemotherapy induced nausea and vomiting, alcohol use disorders, dystonia, multiple sclerosis, inflammatory bowel disorders, arthritis, dermatitis, Rheumatoid arthritis, systemic lupus erythematosus, anti-inflammatory, anti-convulsant, anti-psychotic, anti-oxidant, neuroprotective, anti-cancer, immunomodulatory effects, peripheral neuropathic pain, neuropathic pain associated with post-herpetic neuralgia, diabetic neuropathy, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, ankylosing spondylitis, psoriatic arthritis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, synovitis, juvenile rheumatoid arthritis and inhibition of hair growth.

In one embodiment, the resulting prodrug is more hydrophilic than cannabidiol and therefore more water soluble. The $\log_{10}$ values of the water/octanol partition coefficient (log P) for cannabidiol and various prodrugs of cannabidiol are shown in Table 15. A further embodiment is a prodrug of cannabidiol having a log P value less than that of cannabidiol. A further embodiment is a prodrug of cannabidiol having a log P value greater than that of cannabidiol. A further embodiment is a prodrug of cannabidiol having a log P value which is approximately equal to that of cannabidiol.

Pharmaceutical Excipients

The pharmaceutical compositions described herein can, if desired, include one or more pharmaceutically acceptable excipients. The term "excipient" herein means any substance, not itself a therapeutic agent, used as a carrier or vehicle for delivery of a therapeutic agent to a subject or combined with a therapeutic agent (e.g., to create a pharmaceutical composition) to improve its handling or storage properties or to permit or facilitate formation of a dose unit of the composition. Excipients include, by way of illustration and not limitation, binders, disintegrants, taste enhancers, solvents, thickening agents, penetration enhancers, wetting agents, lubricants, emollients, substances added to mask or counteract a disagreeable odor, fragrances or taste, and substances added to improve appearance or texture of the composition. Any such excipients can be used in any dosage forms according to the present disclosure. The foregoing classes of excipients are not meant to be exhaustive but merely illustrative as a person of ordinary skill in the art would recognize that additional types of excipients could be used to achieve the desired goals for delivery of the cannabidiol prodrug.

Compositions of the disclosure containing excipients can be prepared by any technique known to a person of ordinary skill in the art of pharmacy, pharmaceutics, drug delivery, pharmacokinetics, medicine or other related discipline that comprises admixing an excipient with a drug or therapeutic agent.

In one embodiment, the cannabidiol prodrugs described herein can be combined with a penetration enhancing agent for transdermal or topical delivery. Non-limiting examples of penetration enhancing agents include C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyl oleate, isopropyl myristate, butyl stearate, and methyl laurate; di(lower) alkyl esters of C6-C22 diacids such as diisopropyl adipate; monoglycerides of C8-C22 fatty acids such as glyceryl monolaurate; tetrahydrofurfuryl alcohol polyethylene glycol ether; polyethylene glycol, propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes. Additional penetration enhancers suitable for use can also be found in U.S. patent application Ser. No. 10/032,163.

In one embodiment, the cannabidiol prodrugs can be combined with a thickening or gelling agent. Non-limiting examples of thickening agents (aka gelling agents) which ma be used herein include anionic polymers such as polyacrylic acid (CARBOPOL® by Noveon, Inc., Cleveland, Ohio), carboxypolymethylene, carboxymethylcellulose and the like, including derivatives of Carbopol® polymers, such as Carbopol® Ultrez 10, Carbopol® 940, Carbopol® 941, Carbopol® 954, Carbopol® 980, Carbopol® 981, Carbopol® ETD 2001, Carbopol® EZ-2 and Carbopol® EZ-3, and other polymers such as Pemulen® polymeric emulsifiers, and Noveon® polycarbophils. Additional thickening agents, enhancers and adjuvants may generally be found in Remington's The Science and Practice of Pharmacy as well as the Handbook f Pharmaceutical Excipients, Arthur H. Kibbe ed.

2000. Thickening agents or gelling agents are present in an amount sufficient to provide the desired rheological properties of the composition. Illustratively, one or more pharmaceutically acceptable thickening agent or gelling agent are present in a total amount by weight of about 0.1%, about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75%, about 10%, about 11%, about 11.5%, about 12%, about 12.5%, about 13%, about 13.5%, about 14%, about 14.5% or about 15%.

In one embodiment a neutralizing agent is optionally present to assist in forming a gel. Suitable neutralizing agents include sodium hydroxide (e.g., as an aqueous mixture), potassium hydroxide (e.g., as an aqueous mixture), ammonium hydroxide (e.g., as an aqueous mixture), triethanolamine, tromethamine (2-amino 2-hydroxymethyl-1,3 propanediol), aminomethyl propanol (AMP), tetrahydroxypropyl ethylene diamine, diisopropanolamine, Ethomeen C-25 (Armac Industrial Division), Di-2 (ethylhexyl)amine (BASF-Wyandotte Corp., Intermediate Chemicals Division), triamylamine, Jeffamine D-1000 (Jefferson Chemical Co.), b-Dimethylaminopropionitrite (American Cyanamid Co.), Armeen CD (Annac Industrial Division), Alamine 7D (Henkel Corporation), dodecylamine and morpholine. The neutralizing agent is present in an amount sufficient to form a gel which is suitable for contact with the skin of a mammal.

In one embodiment, the formulation is a gel, an ointment, a cream or a patch and comprises a cannabidiol prodrug, optionally a penetration enhancing agent, a thickening agent, a lower alcohol, such as ethanol or isopropanol; and water. In another embodiment, the formulation is a gel, an ointment, a cream or a patch, further comprised of an aqueous solution of sodium hydroxide or triethanolamine or an aqueous solution of potassium hydroxide, or a combination thereof, in an amount sufficient, as is known in the art, to assist the gelling agent in forming a gel.

In one embodiment, a solution of sodium hydroxide is used, such as, e.g., 0.1 N sodium hydroxide solution, 0.2 N sodium hydroxide solution, 0.5 N sodium hydroxide solution, 1.0 N sodium hydroxide solution, 1.5 N sodium hydroxide solution, 2.0 N sodium hydroxide solution, or any other suitable solution for providing an amount sufficient of the aqueous sodium hydroxide to form the desired gel. In one embodiment, the composition results from combining a gelling agent with a neutralizing agent such as about 1% to about 10% (wt/wt) 0.1 N sodium hydroxide. Of course, other suitable neutralizing agents can be used as can other concentrations of aqueous sodium hydroxide so long as there is a sufficient amount of OH⁻ ions to assist in the formation of a gel.

Additional embodiments include the following compositions:

| Gel formulation used with patches (18 mg/mL CBD or cannabidiol prodrug) | |
|---|---|
| 75.2% | propylene glycol, USP |
| 18.8% | sterile water for injection, USP |
| 6.0% | diethylene glycol monoethyl ether (Transcutol HP), EP/USP/NF |
| 5.0% | hydroxyethylcellulose (Natrosol ®), NF based on weight of other three components Gel formulation used for rubbing into skin |
| 72.5-67.5% | absolute ethanol, USP/NF |
| 20.38-15.38% | sterile water for injection, USP |
| 4.72% | 0.1N NaOH (NF) in sterile water for injection, USP |
| 1-10% | cannabidiol or cannabidiol prodrug |
| 0.9% | Carbopol 980 ®, NF |
| 0.5% | isopropyl myristate, USP/NF Gel formulation |
| 78.1% | absolute ethanol, USP/NF |
| 15.3% | sterile water for injection, USP |
| 1.5% | triethanolamine, NF |
| 3.5% | cannabidiol or cannabidiol prodrug |
| 1.0% | Carbopol 980 ®, NF |
| 0.6% | isopropyl myristate, USP/NF Gel formulation |
| 91.75-82.75% | absolute ethanol, USP/NF |
| 5.0% | propylene glycol, USP |
| 1-10% | cannabidiol or cannabidiol prodrug |
| 1.25% | polyoxyethylene (15) cocoalkylamines (Ethomeen ® C/25) |
| 0.5% | Carbopol 980 ®, NF |
| 0.5% | isopropyl myristate, USP/NF |

Compositions described herein optionally comprise one or more pharmaceutically acceptable wetting agents as excipients. Non-limiting examples of surfactants that can be used as wetting agents in compositions of the disclosure include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the composition. Illustratively, one or more pharmaceutically acceptable wetting agents are present in a total amount by weight of about 0.25%, about 0.5%, about 0.75%, about 1%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, about 7.5%, about 7.75%, about 8.0%, about 8.25%, about 8.5%, about 8.75%, about 9.0%, about 9.25%, about 9.5%, about 9.75% or about 10%.

Compositions described herein optionally comprise one or more pharmaceutically acceptable lubricants (including antiadherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition. Illustratively, one or more pharmaceutically acceptable lubricants are present in a total amount by weight of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9% or about 10.0%.

In another embodiment, the compositions described herein optionally comprise an emollient. Illustrative emollients include mineral oil, mixtures of mineral oil and lanolin alcohols, cetyl alcohol, cetostearyl alcohol, petrolatum, petrolatum and lanolin alcohols, cetyl esters wax, cholesterol, glycerin, glyceryl monostearate, isopropyl myristate, isopropyl palmitate, lecithin, allyl caproate, althea officinalis extract, arachidyl alcohol, argobase EUC, butylene glycol dicaprylate/dicaprate, acacia, allantoin, carrageenan, cetyl dimethicone, cyclomethicone, diethyl succinate, dihydroabietyl behenate, dioctyl adipate, ethyl laurate, ethyl palmitate, ethyl stearate, isoamyl laurate, octanoate, PEG-75 lanolin, sorbitan laurate, walnut oil, wheat germ oil, super refined almond, super refined sesame, super refined soyabean, octyl palmitate, caprylic/capric triglyceride and glyceryl cocoate. An emollient, if present, is present in the compositions described herein in an amount of about 1% to about 30%, about 3% to about 25%, or about 5% to about 15%, by weight. Illustratively, one or more emollients are present in a total amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight.

In one embodiment, the compositions described herein comprise an antimicrobial preservative. Illustrative anti-microbial preservatives include acids, including but not limited to benzoic acid, phenolic acid, sorbic acids, alcohols, benzethonium chloride, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, propylparaben, sodium propionate, or thimerosal. The anti-microbial preservative, if present, is present in an amount of about 0.1% to about 5%, about 0.2% to about 3%, or about 0.3% to about 2%, by weight, for example about 0.2%, about 0.4%, about 0.6%, about 0.8%, about 1%, about 1.2%, about 1.4%, about 1.6%, about 1.8%, about 2%, about 2.2%, about 2.4%, about 2.6%, about 2.8%, about 3.0%, about 3.2%, about 3.4%, about 3.6%, about 3.8%, about 4%, about 4.2%, about 4.4%, about 4.6%, about 4.8%, or about 5%.

Compositions described herein optionally compromise one or more emulsifying agents. The term "emulsifying agent" refers to an agent capable of lowering surface tension between a non-polar and polar phase and includes compounds defined elsewhere as "self emulsifying" agents. Suitable emulsifying agents can come from any class of pharmaceutically acceptable emulsifying agents including carbohydrates, proteins, high molecular weight alcohols, wetting agents, waxes and finely divided solids. The optional emulsifying agent, if present, is present in a composition in a total amount of about 1% to about 15%, about 1% to about 12%, about 1% to about 10%, or about 1% to about 5% by weight of the composition. Illustratively, one or more emulsifying agents are present in a total amount by weight of about 1%, about 2%, about 3%, about 4%, about 5%, about 6%, about 7%, about 8%, about 9%, about 10%, about 11%, about 12%, about 13%, about 14%, or about 15%.

In another embodiment, the water immiscible solvent comprises propylene glycol, and is present in a composition in an amount of about 1% to about 99%, by weight of the composition, for example about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99%.

Compositions described herein may optionally comprise one or more binding agents. Binding agents may be either dry or wet. Dry binding agents may include simple and complex carbohydrates (e.g., sucrose, glucose, fructose, maltose, lactose, maltodextrins, starch, modified starches, mannitol, sorbitol, maltitol, xylitol, and erthritol), cellulose, and cellulosic derivatives (e.g., microcrystalline cellulose, carboxymethyl cellulose, and hydroxyethyl cellulose). Wet binder agents may include, polyvinyl pyrrolidone, methycellulose, hydroxypropyl cellulose, hydroxypropyl methylcellulose, carboxymethylcellulose, xanthan gum, carrageenan gum, locust bean gum, alginates, and acacia. Depending on the desired result, a person of ordinary skill in the art of pharmacy, pharmaceutics, drug delivery, pharmacokinetics, medicine or other related discipline that comprises admixing an excipient with a drug or therapeutic agent to a composition would be able to select the appropriate binding agent and the relative concentration of the binding agent.

In another embodiment, the compositions described herein may contain disintegrants, such as sodium starch glycolate, crosspovidone, crosscarmellose, microcrystalline cellulose and starch. Depending on the desired result, a person of ordinary skill in the art of pharmacy, pharmaceutics, drug delivery, pharmacokinetics, medicine or other related discipline that comprises admixing an excipient with a drug or therapeutic agent to a composition would be able to select the appropriate disintegrant and the relative concentration of the disintegrant.

In a further embodiment, the compositions disclosed herein may contain lubricants, such as magnesium stearate, stearic acid and its pharmaceutically acceptable salts, talc, vegetable oils, and waxes. Depending on the desired result, a person of ordinary skill in the art of pharmacy, pharmaceutics, drug delivery, pharmacokinetics, medicine or other related discipline that comprises admixing an excipient with a drug or therapeutic agent to a composition would be able to select the appropriate lubricant and the relative concentration of the lubricant.

Compositions described herein may also optionally comprise one or more taste enhancers, such as sweeteners, including aspartame, acesulfame potassium, sucralose and saccharin or taste masking agents, such as flavorings. Depending on the desired result, a person of ordinary skill in the art of pharmacy, pharmaceutics, drug delivery, pharmacokinetics, medicine or other related discipline that comprises admixing an excipient with a drug or therapeutic agent to a composition would be able to select the appropriate taste enhancer or taste making agent and the relative concentration of the taste enhancer or taste masking agent.

Therapeutic Uses

In one embodiment, compositions disclosed herein comprise one or more cannabidiol prodrugs in a total amount of between about 0.1% and about 95% by weight of the composition, for example about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90% or about 95%.

The term "therapeutically effective amount" or "therapeutically and/or prophylactically effective amount" as used herein refers to an amount of compound or agent that is sufficient to elicit the required or desired therapeutic and/or prophylactic response, as the particular treatment context may require.

It will be understood that a therapeutically and/or prophylactically effective amount of a drug for a subject is dependent inter alia on the body weight of the subject as well as other factors known to a person of ordinary skill in the art. A "subject" herein to which a therapeutic agent or composition thereof can be administered includes mammals such as a human subject of either sex and of any age, and also includes any nonhuman animal, particularly a domestic or companion animal, illustratively a cat, dog or a horse as well as laboratory animals such as guinea pigs.

The terms "treat", "treated", "treating" and "treatment" are to be broadly understood as referring to any response to, or anticipation of, a medical condition in a mammal, particularly a human, and includes but is not limited to:

(i) preventing the medical condition from occurring in a subject, which may or may not be predisposed to the condition, but has not yet been diagnosed with the condition and, accordingly, the treatment constitutes prophylactic treatment for the medical condition;

(ii) inhibiting the medical condition, i.e., arresting, slowing or delaying the onset, development or progression of the medical condition; or (iii) relieving the medical condition, i.e., causing regression of the medical condition.

In one embodiment, a therapeutically effective amount of a cannabidiol prodrug is administered to treat a medical condition selected from the group consisting of: nausea, emesis, pain, wasting syndrome, HIV-wasting, chemotherapy induced nausea and vomiting, alcohol use disorders, dystonia, multiple sclerosis, inflammatory bowel disorders, arthritis, dermatitis, Rheumatoid arthritis, systemic lupus erythematosus, anti-inflammatory, anti-convulsant, anti-psychotic, anti-oxidant, neuroprotective, anti-cancer, immunomodulatory effects, peripheral neuropathic pain, neuropathic pain associated with post-herpetic neuralgia, diabetic neuropathy, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, ankylosing spondylitis, psoriatic arthritis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, synovitis, juvenile rheumatoid arthritis and inhibition of hair growth.

Pharmaceutical Dosage Forms

In one embodiment, a single dosage unit of any formulation comprises a therapeutically effective amount or a therapeutically and/or prophylactically effective amount of a cannabidiol prodrug.

In one embodiment, compositions described herein are suitable for transdermal administration. In another embodiment, transdermally administrable compositions are adapted for administration in and/or around the abdomen, back, chest, legs, arms, scalp or other suitable skin surface and may include formulations in which the cannabidiol prodrug is administered in patches, ointments, creams, suspensions, lotions, pastes, gels, sprays, foams or oils.

In another embodiment, compositions described herein which are transdermally administrable include formulations in which the cannabidiol prodrug is placed in a glycol or gel formulation.

In one embodiment, compositions described herein are suitable for topical administration. In another embodiment, topical administrable compositions are adapted for administration in and/or around the abdomen, back, chest, legs, arms, scalp or other suitable skin surface and may include formulations in which the cannabidiol prodrug is administered in patches, ointments, creams, suspensions, lotions, pastes, gels, sprays, foams or oils.

In another embodiment, the compositions described herein are suitable for oral administration. In another embodiment, compositions described herein that are orally administrable include formulations in which the cannabidiol prodrug is administered in tablets, capsules, suspensions, syrups or liquids. In an additional embodiment, the composition maybe formulated as extended release or long acting tablet or capsule. In a further embodiment, the oral dosage form may be enteric coated using compositions and techniques known to a person of ordinary skill in the art.

In one embodiment, compositions described herein are suitable for buccal administration. In another embodiment, compositions described herein that are bucally administrable may include formulations in which the cannabidiol prodrug is administered in lozenges, sprays, gels, pastes, dissolvable tablets or dissolvable strips.

In one embodiment, compositions described herein are suitable for sublingual administration. In another embodiment, compositions described herein that are sublingually administrable may include formulations in which the cannabidiol prodrug is administered in lozenges, sprays, gels, pastes, dissolvable tablets or dissolvable strips.

In one embodiment, compositions described herein are suitable for injectable administration. In another embodiment, compositions described herein that are injectably administrable may include formulations in which the cannabidiol prodrug is administered as an intravenous, intrathecal, subcutaneous or depot injection.

In one embodiment, compositions described herein are suitable for rectal administration. In another embodiment, compositions described herein that are rectally administrable may include formulations in which the cannabidiol prodrug is placed in suppositories, ointments, creams, suspensions, solutions, lotions, pastes, gels, sprays, foams or oils.

In one embodiment, compositions described herein are suitable for vaginal administration. In another embodiment, compositions described herein that are vaginally administrable may include formulations in which the cannabidiol prodrug is placed in suppositories, ointments, creams, suspensions, solutions, lotions, pastes, gels, sprays, foams or oils.

In one embodiment, compositions described herein are suitable for ocular administration. In another embodiment, compositions described herein that are ocularly administrable may include formulations in which the cannabidiol prodrug is placed in ointments, suspensions, solutions, gels or sprays.

In one embodiment, compositions described herein are suitable for nasal administration. In another embodiment, compositions described herein that are nasally administrable may include formulations in which the cannabidiol prodrug is placed in ointments, suspensions, solutions, lotions, pastes, gels, sprays or mists.

EXAMPLES

Example 1

Section I. Summary

The objective was to synthesize cannabidiol and cannabidiol prodrugs and assess the permeation of cannabidiol and its prodrugs through human abdominal skin in vitro. Cannabidiol and five cannabidiol prodrugs were synthesized and tested. Flow through diffusion cells were used for the permeation studies. HEPES-buffered Hanks' balanced salts containing 40% (polyethylene glycol) PEG 400 with gentamicin was used for the receiver compartment. Donor solution was comprised of either 100% propylene glycol (PG) solution or a rubbed in gel formulation. The flux and lag time values of cannabidiol and cannabidiol prodrugs were obtained from the permeation profiles. Drug accumulation in the skin after a 24 or 36 h diffusion experiment was determined as µmol/g wet tissue weight.

These prodrugs also have improved physiochemical properties that would make them suitable candidates for improved delivery via other routes of administration, including oral, buccal, sublingual, injectable, topical, follicular, nasal, ocular, rectal or vaginal.

Section II. Methodology 1.0 Purpose:

Synthesize Cannabidiol Prodrugs and Assess the Human Skin Permeation of Cannabidiol and Cannabidiol Prodrugs In Vitro.

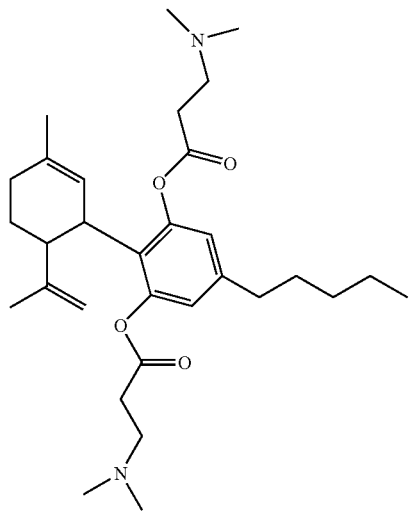

Formula: $C_{31}H_{48}N_2O_6$
MW: 512
ALL00101

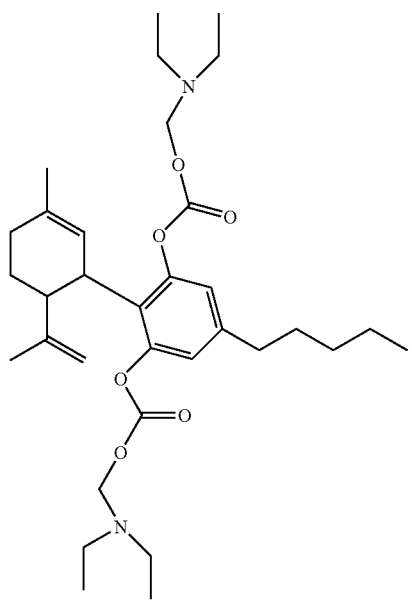

Formula: $C_{33}H_{52}N_2O_6$
MW: 572
ALL00102

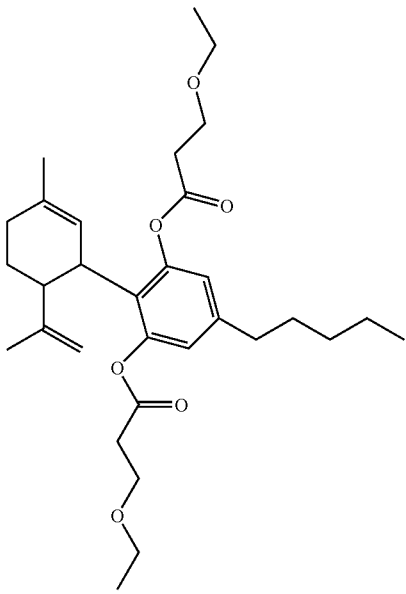

Formula: C₃₁H₄₆O₆
MW: 514
ALL00103

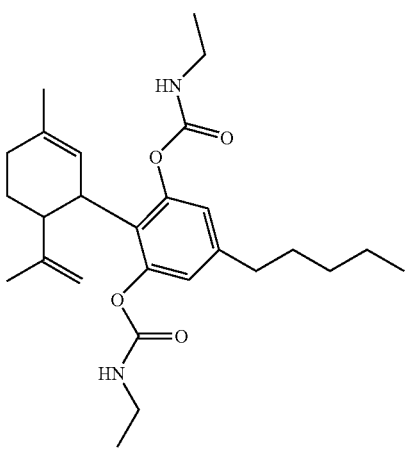

Formula: C₂₇H₄₀N₂O₄
MW: 456
ALL00104

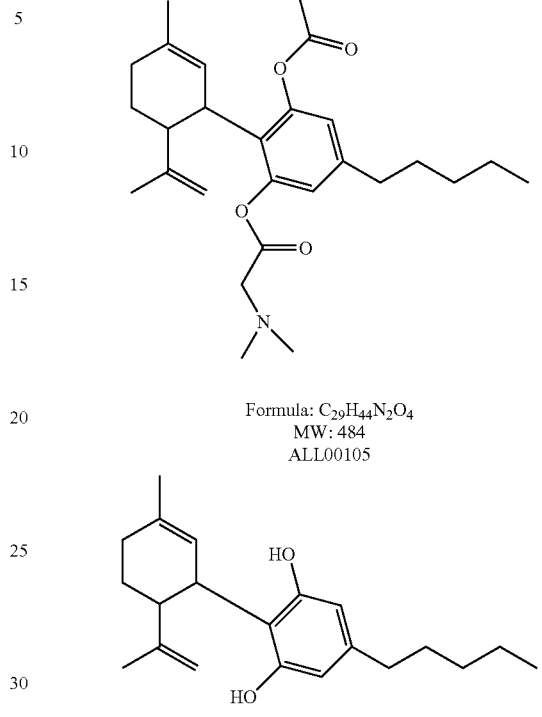

Formula: C₂₉H₄₄N₂O₄
MW: 484
ALL00105

Formula: C₂₁H₃₀N₂
MW: 314
cannabidiol 2.0 Skin Details

The skin samples used in the following experiments were obtained from abdominal reduction surgery and dermatomed to a thickness of approximately 200 μm. The skin samples used herein were frozen at −20° C. for less than six months.

3.0 Chemicals

The chemicals used in the experiment included: acetonitrile (HPLC grade), trifluoroacetic acid, triethylamine, 4-(2-hydroxy ethyl)-piperzine ethane sulfonic acid (HEPES), gentamicin sulfate, p-toluene sulfonic acid, 4-dimethylaminopyridine, isopropyl myristate (IPM), sodium hydroxide, and sodium bicarbonate were purchased through Fisher Scientific (Fairlawn, N.J.). Methanol (HPLC grade), acetonitrile (HPLC grade), 3-O-ethoxy-propionic acid, diethyl ether, N,N¹-dicyclohexyl carbodiimide, N,N-dimethylgylcine, polyethylene glycol 400 (PEG 400), and sodium sulfate anhydrous were purchased through VWR (West Chester, Pa.). Propylene glycol (PG), olivetol, chloromethyl chloroformate, ethyl isocyanate, absolute ethanol, and Hanks' balanced salts modified powder were purchased from Sigma-Aldrich (St. Louis, Mo.). Petroleum ether, ethyl acetate, hexane, chloroform, and dichloromethane were obtained from the University of Kentucky Chemical Stores (Lexington, Ky.). (+)-(1S,4R)-p-Mentha-2,8-dien-1-ol was purchased from Norac, Inc. (Azusa, Calif.). Carbopol® 980 was obtained from Noveon, Inc. (Cleveland, Ohio). Nanopure water was obtained from a Barnstead filtration system (Dubuque, Iowa).

4.0 Synthesis of Cannabidiol and Cannabidiol Prodrugs 4.1 Synthesis of Cannabidiol Olivetol (920 mg, 0.00511 mol) and p-toluene sulfonic acid (PTSA) (110 mg, 0.000578 mol) were dissolved in benzene; the resulting reaction mixture azeotroped for 2.5 h. The reaction mixture was cooled to room temperature and under argon (+)-(1S,4R)-p-Mentha-2,8-dien-1-ol (586 mg, 0.00385 mol) was added and stirred at room temperature for 30 min. After completion of the reaction, the reaction mixture was diluted with diethyl ether and washed with saturated sodium bicarbonate solution. The organic layer separated and was dried on anhydrous sodium sulfate. The ether layer evaporated and purified on silica column by using petroleum ether and diethyl ether as eluent (98:2). Finally 300 mg of cannabidiol (300 mg) was collected (24%).

$^1$HNMR (CDCl$_3$): 6.23-6.41 (m, 2H), 5.99 (s, 1H, D$_2$O exchangeable), 5.66 (s, 1H), 4.56 (s, 1H), 4.49 (bs, 1H, D$_2$O exchangeable) 4.46 (s, 1H), 3.96 (m, 1H), 2.00-2.47 (m, 5H), 1.87 (m, 5H), 1.46-1.83 (m, 6H), 1.23-1.48 (m, 3H), 0.96-1.00 (m, 3H).

4.2 Synthesis of ALL00101

β-alanine,N,N-dimethyl (0.600 mg, 0.00512 mol), N,N'-dicyclohexyl carbodiimide (DCC) (1.05 g, 0.00512 mol), 4-dimethylaminopyridine (DMAP) (85 mg) were dissolved in dichloromethane (DCM) and stirred under nitrogen for 2 h; later cannabidiol (806 mg, 0.00264 mol) in DCM was added. The resulting reaction mixture stirred overnight and the solid was filtered on celite. The crude product was purified on silica column producing 300 mg (26.48%) of final compound (ALL00101).

4.3 Synthesis of ALL00102

Cannabidiol (216 mg, 0.0006878 mol) was dissolved in dichloromethane and reaction mixture cooled to 0° C. on ice bath and chloromethyl chloroformate (177 mg, 0.001375 mol) was added drop wise up to 30 min and the reaction mixture stirred overnight at room temperature. After completion of the reaction, the reaction mixture was washed with water, the combined organic layer dried, evaporated, and purified on silica column by using petroleum ether and diethyl ether (9:1) as eluent. The title compound was as an oil compound (130 mg, 37%). This oily compound (130 mg, 0.000260 mol) was treated with excess of diethylamine to give the target compound (31.5 mg, 21%).

$^1$HNMR (CDCl$_3$): 6.90 (s, 2H), 5.83-5.84 (dd, 4H), 5.19 (S, 1H, cyclic ethylenic), 4.54-4.55 (d, 1H), 4.44-4.44 (d, 1H), 3.50-3.55 (m, 1H) 2.57-2.62 (m, 3H), 1.90-2.12 (m, 2H), 1.34-1.59, 1.62-1.64 (m, 11H), 1.30-1.33 (m, 5H), 0.90-0.92 (m, 3H) $^{13}$C-NMR (CDCl$_3$): 13.89, 19.27, 22.30, 23.31, 28.48, 30.02, 30.22, 31.23, 35.05, 37.87, 45.63, 72.19, 72.23, 72.28, 111.05, 122.12, 122.15, 122.18, 134.28, 142.53, 147.13, 149.10, 151.34 $^1$HNMR (CDCl$_3$): 6.81 (s, 2H), 5.42 (s, 1H), 4.68 (dd, 2H), 3.69 (m, 1H), 3.24-3.47 (m, 10H), 2.49-2.57 (m, 3H), 2.01 (m, 2H), 1.69-1.95 (m, 12H), 1.15-1.46 (m, 17H), 0.93-0.95 (m, 3H) $^{13}$C-NMR (CDCl$_3$): 13.71, 14.35, 14.62, 20.53, 22.76, 23.65, 29.50, 30.82, 30.99, 31.98, 35.62, 38.80, 41.61, 42.20, 46.08, 110.90 125.63, 126.36, 131.61, 141.50, 148.04, 150.30, 153.92.

4.4 Synthesis of ALL00103

3-O-ethoxy-propionic acid (0.507 mg, 0.0042 mol), DCC (889 mg, 0.00429 mol), and DMAP (138 mg) were dissolved in DCM under nitrogen, stirring for 2 h. Cannabidiol (450 mg, 0.00143 mol) was added in DCM for 30 min and resulting reaction mixture stirred overnight. The solid was filtered through celite, filtrate purified by using (75:25) petroleum ether, and diethyl ether was used as eluent giving 210 mg (51.4%) an oily final compound.

$^1$HNMR (CDCl$_3$): 6.78 (s, 2H), 5.20 (s, 1H), 4.45-4.53 (dd, 2H), 3.77-3.80 (m, 4H), 3.58 (m, 1H), 3.50-3.57 (t, 4H), 2.57-2.90 (m, 4H), 2.51-2.56 (t, 2H), 2.10 (m, 1H), 2.00 (m, 1H), 1.61-1.90 (m, 2H), 1.57-1.65 (m, 9H), 1.30-1.32 (m, 1H), 1.21-1.29 (t, 6H), 0.85-0.90 (m, 3H) $^{13}$C-NMR (CDCl$_3$): 14.25, 15.35, 19.84, 22.68, 23.59, 28.97, 30.56, 30.70, 31.67, 35.39, 38.46, 45.82, 65.78, 66.68, 111.13, 124.69, 126.02, 141.94, 147.80, 149.58, 169.78.

4.5 Synthesis of ALL00104

Cannabidiol (284 mg, 0.000904 mol) and triethylamine (0.482 mL, 0.00226 mol) were dissolved in DCM and stirred at room temperature for 1 h. Ethyl isocyanate (0.1419 mL, 0.00180 mol) was added drop wise for 10 min to give the reaction mixture which stirred overnight. The solvents were evaporated and the crude product purified on silica column by using (8:2) hexane:ethyl acetate as eluent. The final compound (260 mg, 63%) collected was a semi solid.

$^1$HNMR (CDCl$_3$): 6.77 (s, 2H), 5.30 (m, 1H), 4.11 (bs, 2H), 4.42 (s, 1H), 4.85 (s, 1H), 3.15 (m, 4H), 2.46-2.64 (m, 3H), 2.10 (m, 2H), 1.88 (2H), 1.25-1.66 (m, 10H), 1.30 (m, 5H), 1.17-1.22 (m, 5H), 0.88 (m, 3H) $^{13}$C-NMR (CDCl$_3$): 14.36, 14.53, 15.53, 19.87, 22.80, 23.71, 25.02, 29.17, 30.75, 30.90, 31.87, 35.61, 36.44, 36.97, 38.26, 46.24, 111.14, 124.60, 127.12, 132.37, 141.76, 147.97, 149.87, 154.26.

4.6 Synthesis of ALL00105

Cannabidiol (280 mg, 0.000890 mol) was added to activate DCC (550 mg, 0.00267 mol), DMAP (429 mg, 0.00133 mol), and N,N-dimethylglycine (275 mg, 0.002678 mol) in DCM at room temperature. After overnight stirring under nitrogen, the solid in the reaction mixture was filtered though celite and the reaction mixture purified on silica column by using chloroform and methanol (97:3) as eluent gave 70 mg of final compound (10.07%).

$^1$HNMR (CDCl$_3$): 6.42 (s, 2H), 5.12 (s, 1H), 4.20-4.40 (dd, 2H), 2.21 (s, 4H), 2.34-2.40 (m, 1H), 2.20-2.34 (m, 13H), 2.00-2.10 (m, 3H), 1.29-1.42 (m, 10H), 1.13-1.26 (m, 4H), 0.91-0.92 (m, 3H) $^{13}$C-NMR (CDCl$_3$): 14.36, 20.16, 22.80, 23.90, 29.12, 30.67, 30.85, 31.75, 35.53, 38.86, 45.57, 45.86, 60.16, 111.23, 124.69, 125.94, 132.71, 142.17, 147.86, 149.38, 168.73.

5.0 In Vitro Skin Permeation Studies

5.1 Preparation of Receiver Fluid

1 L of receiver fluid was prepared by measuring 1 L of nanopure water into a graduated cylinder. 90% of the water was added to an Erlenmeyer flask. Hanks' salts (1 bottle) were added to the water along with 5.96 g of HEPES and 0.35 g of sodium bicarbonate. The pH of the solution was adjusted with 1 N sodium hydroxide solution to pH 7.4. The remaining water was added and the receiver fluid was filtered through a 0.2µ filter (Millipore, Billerica, Mass.). 50 mg of gentamicin was added to the filtered receiver fluid and 400 mL of the receiver fluid was removed and replaced with 400 mL of PEG 400.

5.2 Preparation of Drug Formulations

Two different formulations were used for charging the donor compartment. Drugs were made up in either 100% PG or a gel formulation. For the PG solution, approximately 50-120 mg of the appropriate drug was weighed into a glass silanized culture tube. The gel formulation resulted from the mixing of absolute ethanol, nanopure water, IPM, Carbopol® 980, 0.1 N aqueous sodium hydroxide solution and the respective drug.

5.3 Permeation Experiments

Dermatomed skin harvested from abdominoplasty, stored at −20° C., was used for the experiments. A PermeGear flow-through (In-Line, Riegelsville, Pa.) diffusion cell system was used for the skin permeation studies.

Diffusion cells were kept at 32° C. with a circulating water bath. Human epidermal skin was arranged in the diffusion cell with stratum corneum (upper layer of skin) facing the donor compartment. Permeation area of the skin was 0.95 cm². Data was collected from a human skin donor with three to four diffusion cells per treatment.

Receiver solution was HEPES-buffered Hanks' balanced salts with gentamicin containing 40% PEG 400 at a pH of 7.4 and flow rate was adjusted to 0.8 mL/h. Each cell was charged with 0.050 mL of the respective drug formulation (donor solution) or with 0.035 mL of gel formulation which was rubbed into the skin for 15 sec with a Teflon coated rod. The formulation was applied to ensure complete coverage. Diffusion cells were covered with a cap for the duration of the study.

Samples were collected into scintillation vials in 3 h increments for either 24 h or 36 h. All the samples were stored at 4° C. until extracted. An aliquot (0.5 mL) of the diffusion sample was placed into a silanized HPLC vial and 0.5 mL of acetonitrile was added to the sample, capped and vortexed.

At the end of the experiment, the skin tissue was removed from the diffusion cell, rinsed with nanopure water, and blotted dry with a paper towel. The skin was tape stripped twice using book tape (Scotch™, 3M, St. Paul, Minn.) to remove drug formulation adhering to the tissue surface. The area of skin in contact with the drug was cut out, chopped up and placed in a pre-weighed scintillation vial. Ten mL of acetonitrile was added to the vial and drug was extracted from the skin by shaking at room temperature overnight. The following day a 0.1 mL aliquot was removed and diluted with an additional 0.9 mL of acetonitrile. The diluted sample was added to the silanized HPLC vial for analysis.

At the end of the experiment, a 0.01 mL aliquot of the PG donor solution was removed and added to a scintillation vial containing 10 mL of acetonitrile. The vials were vortexed and then sonicated for 15 min. An aliquot of 1 mL was removed and transferred into a silanized HPLC vial for analysis.

6.0 Analytical Method

Section III. Results

No melting points were reported for cannabidiol or the cannabidiol prodrugs due to all compounds being in oil form. ALL00101 and ALL00102 permeated through the human skin as cannabidiol. No intact prodrug was found in the diffusion samples (receiver samples) for either ALL00101 or ALL00102. Both cannabidiol and intact prodrug were found in the skin disposition (tissue) samples. ALL00101 and ALL00102 did have higher total cannabidiol in the skin compared to cannabidiol. No flux enhancement was seen with ALL00101 or ALL00102 prodrugs. ALL00103 and ALL00104 did not permeate (or were below LOD) through the skin with both the PG donor solution and gel formulation. Some intact prodrug was found in the skin samples but very little cannabidiol was detected for ALL00103 and ALL00104. The mean flux enhancement between the two ALL001005 gel formulation experiments was 2.5. ALL00105 permeated primarily as intact prodrug. The cumulative amount of total cannabidiol equivalents (nmol) delivered from ALL00105 was 3.1-5.9 fold higher when compared to cannabidiol. The same results were not seen with the propylene glycol donor solution which did not show any enhancement. Besides the enhanced flux with ALL00105, the lag time (gel formulation studies) of total cannabidiol was decreased 7-8 h compared to the parent drug. Decreased lag time benefits patients by delivering the drug more quickly which is beneficial for pain management and nausea. The other cannabidiol prodrugs may be successful if drug solutions were formulated with enhancers or may be useful in targeting topical treatment administration instead of transdermal administration (for systemic blood levels of drug).

| | |
|---|---|
| Column | Brownlee ® $C_8$ reversed phase Spheri 5 µm, (4.6 × 220 mm) column with a Brownlee ® $C_8$ reversed phase 7 µm (3.2 × 150 mm) guard column |
| Mobile phase | 85:15 acetonitrile:0.1% trifluroacetic acid with 5% acetonitrile, 85:15 acetonitrile:0.05% trifluroacetic acid with 5% acetonitrile, 80:20 acetonitrile:0.05% trifluroacetic acid with 5% acetonitrile, or 60:40 acetonitrile:0.05% trifluroacetic acid with 5% acetonitrile |
| Flow rate | 1.5 mL/min |
| Wavelength | 215 or 220 nm |
| Injection volume | 100 µL (diffusion samples and respective standards) 10 µL or 20 µL (skin samples, donor samples, and respective standards) |
| Run time | 7-17 min |
| Retention times | cannabidiol = 2.2-9.0 min ALL00101 = 5.3 min ALL00102 = 8.0-11.3 min ALL00103 = 8.4-14 min ALL00104 = 10.5 min ALL00105 = 12.0-16.0 min |

7.0 Data Analysis

Cumulative quantity of drug collected in the receiver compartment was plotted as a function of time. The flux value for a given experiment was obtained from the slope of a steady state portion of the cumulative amount of drug permeated vs. time plot. Lag time was obtained from the x-intercept of the steady state portion of the cumulative amount of drug permeated vs. time plot. In Tables 11-14, the combined results of the delivered prodrug and cannabidiol from the prodrug are listed as "total cannabidiol." These values represent the data as total cannabidiol equivalents delivered in the form of cannabidiol and/or prodrug.

TABLE 1

Cannabidiol and cannabidiol prodrugs

| Compound | Molecular formula | Molecular weight |
|---|---|---|
| cannabidiol | $C_{21}H_{30}O_2$ | 314 |
| ALL00101 | $C_{31}H_{48}N_2O_6$ | 512 |
| ALL00102 | $C_{33}H_{52}N_2O_6$ | 572 |
| ALL00103 | $C_{31}H_{46}O_6$ | 514 |
| ALL00104 | $C_{27}H_{40}N_2O_4$ | 456 |
| ALL00105 | $C_{29}H_{44}N_2O_4$ | 484 |

TABLE 2

Permeation data of cannabidiol (n = 3) in propylene glycol

| Compound | 24 h skin conc. (μmol/g) | 24 h cumulative amt (nmol) | Flux (nmol/cm$^2$/h) | Lag time (h) |
|---|---|---|---|---|
| cannabidiol (CBD) | 190.8 ± 10.7 | 222.7 ± 74.0 | 10.4 ± 2.0 | 12.2 ± 1.8 |

Wherein "n" is the number of skin samples tested.

TABLE 3

Permeation data of CBD-low (n = 2), ALL00101 (n = 2), ALL00102 (n = 2), and CBD-high (n = 3) in propylene glycol

| Compound | 24 h skin conc. (μmol/g) | 24 h cumulative amt (nmol) | Flux (nmol/cm$^2$/h) | Lag time (h) |
|---|---|---|---|---|
| CBD (low conc.) | 26.3 ± 14.1 | 50.1 ± 28.1 | 4.5 ± 2.5 | 12.2 ± 0.0 |
| ALL00101 | 17.4 ± 4.3 (CBD) 29.2 ± 7.6 (PD) | 11.0 ± 0.1 | 1.0 ± 0.4 | 11.7 ± 5.1 |
| ALL00102 | ND | 8.6 ± 6.3 | 0.6 ± 0.5 | NA |
| CBD (high conc.) | 223.1 ± 75.3 | 89.2 ± 15.0 | 7.8 ± 1.1 | 12.0 ± 0.3 |

Wherein "n" is the number of skin samples tested.

TABLE 4

Permeation data of CBD-low (n = 2), ALL00102 (n = 3), and CBD-high (n = 2) in propylene glycol

| Compound | 24 h skin conc. (μmol/g) | 24 h cumulative amt (nmol) | Flux (nmol/cm$^2$/h) | Lag time (h) |
|---|---|---|---|---|
| CBD (low conc.) | 112.5 ± 61.8 | 63.5 ± 47.5 | 6.0 ± 3.3 | 13.6 ± 2.6 |
| ALL00102 | 18.9 ± 9.9 (CBD) 73.4 ± 35.5 (PD) | 9.1 ± 5.0 | 0.7 ± 0.3 | 11.0 ± 2.8 |
| CBD (high conc.) | 167.6 ± 76.7 | 110.4 ± 18.9 | 8.5 ± 2.4 | 11.5 ± 0.4 |

Wherein "n" is the number of skin samples tested.

TABLE 5

Permeation data of CBD-low (n = 4), ALL00102 (n = 2), and CBD-high (n = 2) in propylene glycol

| Compound | 24 h skin conc. (μmol/g) | 24 h cumulative amt (nmol) | Flux (nmol/cm$^2$/h) | Lag time (h) |
|---|---|---|---|---|
| CBD (low conc.) | 75.3 ± 33.1 | 56.9 ± 39.4 | 5.7 ± 3.5 | 13.7 ± 1.2 |
| ALL00102 | 183.1 ± 62.8 (PD) | 13.7 ± 18.6 | 0.3 ± 0.1 | 5.1 ± 0.0 |
| CBD (high conc.) | 104.9 ± 51.0 | 42.4 ± 10.7 | 3.9 ± 0.0 | 10.0 ± 0.0 |

Wherein "n" is the number of skin samples tested.

TABLE 6

Permeation data of CBD (n = 4) in propylene glycol

| Compound | 24 h skin conc. (μmol/g) | 24 h cumulative amt (nmol) | Flux (nmol/cm$^2$/h) | Lag time (h) |
|---|---|---|---|---|
| CBD | 49.2 ± 15.2 | 27.5 ± 32.5 | 4.3 ± 2.4 | 15.1 ± 3.4 |

Wherein "n" is the number of skin samples tested.

TABLE 7

Permeation data of CBD (n = 3) in propylene glycol

| Compound | 36 h skin conc. (μmol/g) | 36 h cumulative amt (nmol) | Flux (nmol/cm$^2$/h) | Lag time (h) |
|---|---|---|---|---|
| CBD | 44.1 ± 15.5 | 15.7 ± 5.4 | 1.0 ± 0.7 | 13.4 ± 9.3 |

Wherein "n" is the number of skin samples tested.

TABLE 8

Permeation data of CBD (n = 3) in gel formulation

| Compound | 36 h skin conc. (μmol/g) | 36 h cumulative amt (nmol) | Flux (nmol/cm$^2$/h) | Lag time (h) |
|---|---|---|---|---|
| CBD | 28.4 ± 8.8 | 52.0 ± 42.7 | 2.0 ± 2.3 | 1.4 ± 1.7 |

Wherein "n" is the number of skin samples tested.

TABLE 9

Permeation data of CBD (n = 3) and ALL00102 (n = 3) in gel formulation

| Compound | 24 h skin conc. (μmol/g) | 24 h cumulative amt (nmol) | Flux (nmol/cm$^2$/h) | Lag time (h) |
|---|---|---|---|---|
| CBD | 24.6 ± 3.6 | 1.9 ± 1.3 | 0.10 ± 0.06 | 3.6 ± 0.1 |
| ALL00102 | 0.4 ± 0.3 (CBD) 22.9 ± 9.3 (PD) | 1.1 ± 0.4 | 0.05 ± 0.02 | 1.6 ± 1.6 |

Wherein "n" is the number of skin samples tested.

TABLE 10

Permeation data of CBD (n = 4) and ALL00102 (n = 4) in propylene glycol

| Compound | 24 h skin conc. (μmol/g) | 24 h cumulative amt (nmol) | Flux (nmol/cm$^2$/h) | Lag time (h) |
|---|---|---|---|---|
| CBD | 85.8 ± 24.3 | 164.5 ± 34.1 | 8.0 ± 0.9 | 14.3 ± 3.1 |
| ALL00102 | 31.3 ± 5.5 (PD) | ND | ND | NA |

Wherein "n" is the number of skin samples tested.

TABLE 11

Permeation data of CBD (n = 3) and ALL00105 (n = 3) in gel formulation

| Compound | 24 h skin conc. (μmol/g) | 24 h cumulative amt (nmol) | Flux (nmol/cm²/h) | Lag time (h) |
|---|---|---|---|---|
| CBD | 29.0 ± 10.2 | 13.3 ± 2.6 | 1.0 ± 0.1 | 10.0 ± 0.9 |
| total CBD* | 84.5 ± 60.7 | 76.5 ± 7.9 | 3.3 ± 0.7 | 1.2 ± 0.1 |
| ALL00105 | 82.1 ± 58.9 | 66.8 ± 9.0 | 2.9 ± 0.5 | 7.9 ± 3.3 |
| CBD from ALL00105 | 2.5 ± 2.1 | 4.1 ± 1.5 | 0.3 ± 0.02 | 0.8 ± 0.4 |

*total CBD = total cannabidiol equivalents delivered in the form of cannabidiol and/or prodrug Wherein "n" is the number of skin samples tested.

TABLE 12

Permeation data of CBD (n = 2) and ALL00105 (n = 2) in gel formulation

| Compound | 24 h skin conc. (μmol/g) | 24 h cumulative amt (nmol) | Flux (nmol/cm²/h) | Lag time (h) |
|---|---|---|---|---|
| CBD | 88.4 ± 36.3 | 2.9 ± 0.1 | 0.24 ± 0.003 | 11.5 ± 0.4 |
| total CBD* | 29.7 ± 9.1 | 8.9 ± 0.04 | 0.41 ± 0.03 | 0.9 ± 1.2 |
| ALL00105 | 27.5 ± 7.4 | 7.3 ± 0.03 | 0.37 ± 0.01 | 3.9 ± 4.8 |
| CBD from ALL00105 | 2.2 ± 2.1 | 1.1 ± 0.02 | 0.06 ± 0.02 | 1.0 ± 0.6 |

Wherein "n" is the number of skin samples tested.

TABLE 13

Permeation data of CBD (n = 1) and ALL00105 (n = 2) in propylene glycol

| Compound | 36 h skin conc. (μmol/g) | 36 h cumulative amt (nmol) | Flux (nmol/cm²/h) | Lag time (h) |
|---|---|---|---|---|
| CBD | 39.4 ± 0.0 | 94.5 ± 0.0 | 4.2 ± 0.0 | 10.9 ± 0.0 |
| total CBD* | 7.2 ± 10.1 | 47.2 ± 0.1 | 1.9 ± 0.2 | 10.0 ± 2.9 |
| ALL00105 | 8.8 ± 0.0 | 14.7 ± 3.2 | 0.5 ± 0.01 | 7.5 ± 0.0 |
| CBD from ALL00105 | 2.8 ± 3.8 | 32.6 ± 3.0 | 1.4 ± 0.2 | 12.6 ± 1.3 |

Wherein "n" is the number of skin samples tested.

TABLE 14

Permeation data of CBD (n = 3) and ALL00103 (n = 4) in propylene glycol

| Compound | 36 h skin conc. (μmol/g) | 36 h cumulative amt (nmol) | Flux (nmol/cm²/h) | Lag time (h) |
|---|---|---|---|---|
| CBD | 92.9 ± 4.8 | 93.6 ± 38.0 | 8.4 ± 2.4 | 10.3 ± 2.0 |
| total CBD* | 9.7 ± 1.0 | ND | ND | ND |
| ALL00103 | 9.7 ± 1.0 | ND | ND | ND |
| CBD from ALL00103 | ND | ND | ND | ND |

Wherein "n" is the number of skin samples tested.

Examples 2, 2A and 2B

Except as where indicated below, the methodology used in Examples 2A and 2B was the same as the methodology used in Example 2.

Section I. Summary

The objective was to synthesize cannabidiol prodrugs and assess the permeation of cannabidiol and various prodrugs of cannabidiol through human abdominal skin in vitro. Cannabidiol and numerous cannabidiol prodrugs were synthesized and several were tested. Flow through diffusion cells were used for the permeation studies. HEPES-buffered Hanks' balanced salts containing 40% PEG 400 with gentamicin or 40% aqueous PEG 400 with gentamicin were used for the receiver compartment. Donor solution was comprised of 90:8:2 PG:H₂O:IPM solution or gel formulation. The flux and lag time values of cannabidiol and cannabidiol prodrugs were obtained from the permeation profiles. Drug accumulation in the skin after a 24, 30 or 42 h diffusion experiment was determined as μmol/g wet tissue weight.

These prodrugs also have improved physicochemical properties that would make them suitable candidates for improved delivery via other routes of administration, including oral, buccal, sublingual, injectable, topical, follicular, nasal, ocular, rectal or vaginal.

Section II. Methodology 1.0 Purpose:

The Purpose of the Example was to Synthesize Cannabidiol Prodrugs and Assess the Human Skin Permeation of Cannabidiol and Cannabidiol Prodrugs In Vitro.

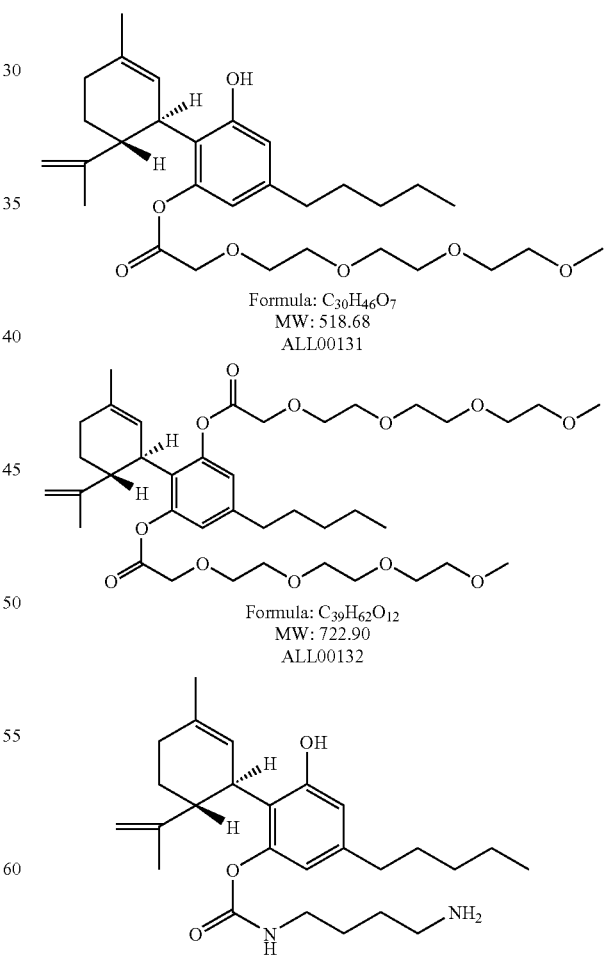

Formula: C₃₀H₄₆O₇
MW: 518.68
ALL00131

Formula: C₃₉H₆₂O₁₂
MW: 722.90
ALL00132

Formula: C₂₆H₄₀N₂O₃
MW: 428.61
ALL00135

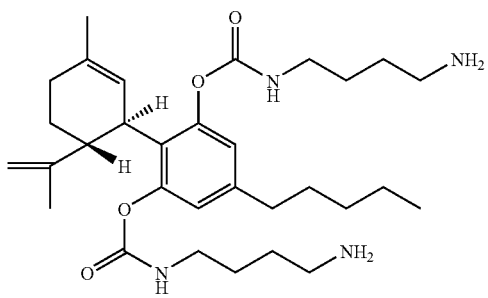
Formula: C₃₁H₅₀N₄O₄
MW: 542.75
ALL00136
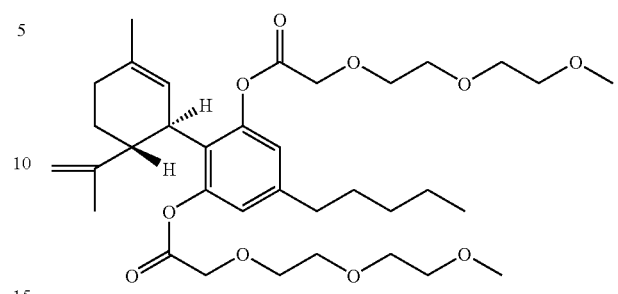
Formula: C₃₅H₅₄O₁₀
MW: 634.80
ALL00141
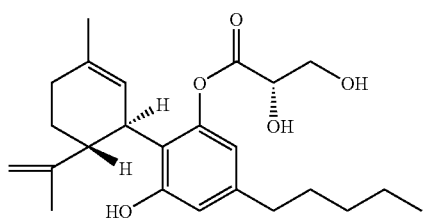
Formula: C₂₄H₃₄O₅
MW: 402.52
ALL00137
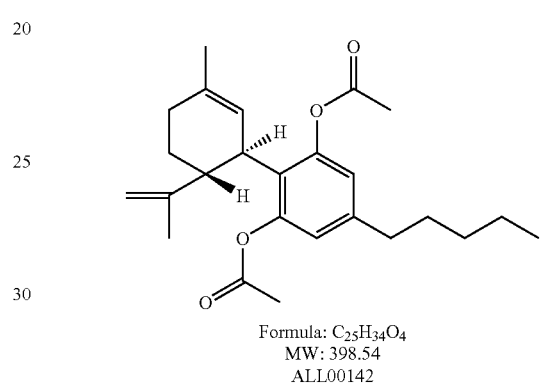
Formula: C₂₅H₃₄O₄
MW: 398.54
ALL00142
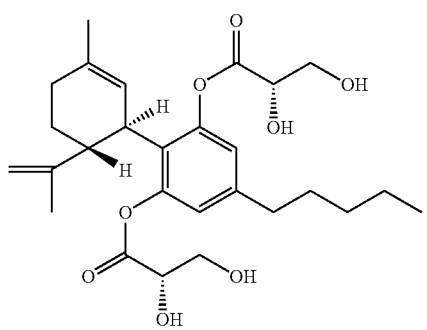
Formula: C₂₇H₃₈O₈
MW: 490.59
ALL00139
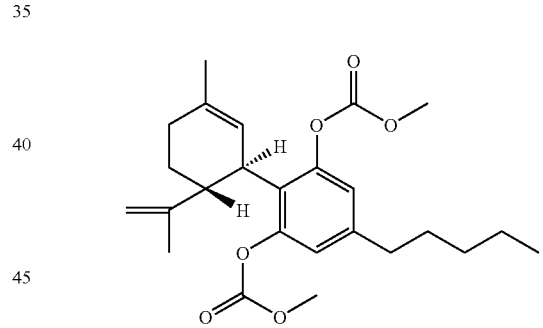
Formula: C₂₅H₃₄O₆
MW: 430.53
ALL00143
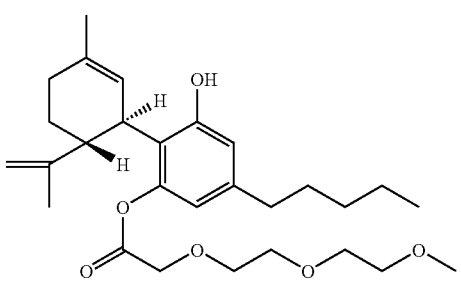
Formula: C₂₈H₄₂O₆
MW: 474.63
ALL00140
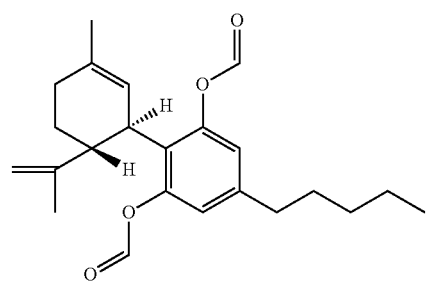
Formula: C₂₃H₃₀O₄
MW: 370.48
ALL00145

-continued

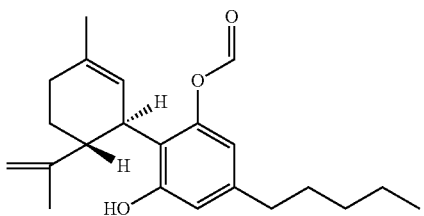

Formula: C₂₂H₃₀O₃
MW: 342.47
ALL00146

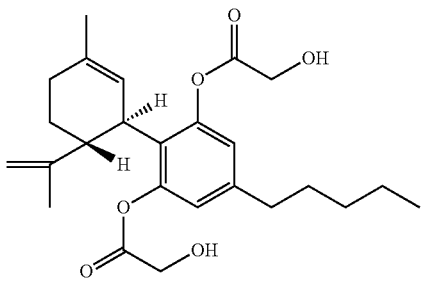

Formula: C₂₅H₃₄O₆
MW: 430.53
ALL00147

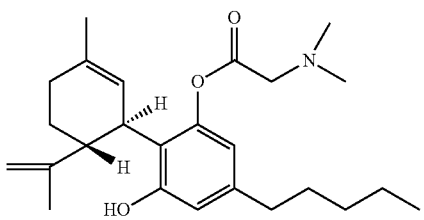

Formula: C₂₅H₃₇NO₃
MW: 399.57
ALL00148

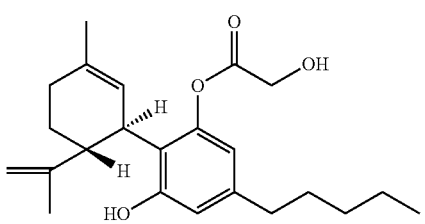

Formula: C₂₃H₃₂O₄
MW: 372.50
ALL00149

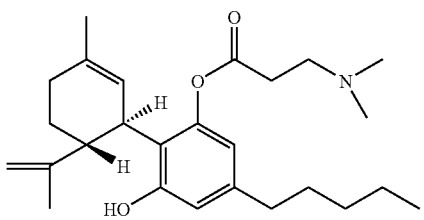

Formula: C₂₆H₃₉NO₃
MW: 413.59
ALL00150

-continued

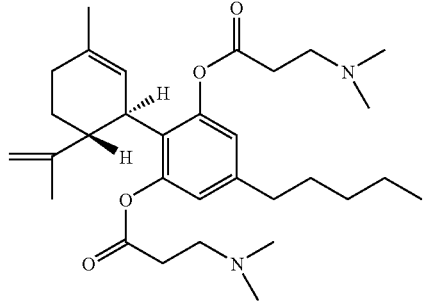

Formula: C₃₁H₄₈N₂O₆
MW: 512.72
ALL00101

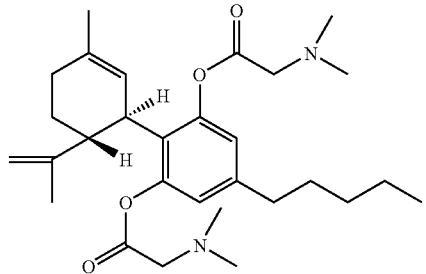

Formula: C₂₆H₄₄N₂O₄
MW: 484.67
ALL00105

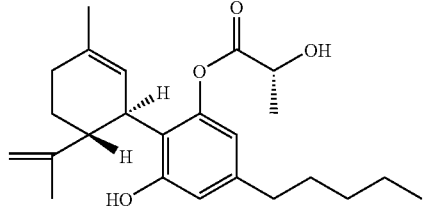

Formula: C₂₄H₃₄O₄
MW: 386.52
ALL00151

2.0 Skin Details

The skin samples used in the following experiments were obtained from abdominal reduction surgery and dermatomed to a thickness of approximately 200 μm. The skin samples used herein were frozen at −20° C. for less than six months.

3.0 Chemicals

Chemicals used in the experiment included: trifluoroacetic acid, triethylamine (TEA), 4-(2-hydroxy ethyl)-piperzine ethane sulfonic acid (HEPES), gentamicin sulfate, isopropyl myristate (IPM), sodium hydroxide, octanethiol, 4-dimethylaminopyridine (DMAP), methyl chloroformate, and sodium bicarbonate (NaHCO₃) were purchased through Fisher Scientific (Fairlawn, N.J.). Methanol (HPLC grade), acetonitrile (HPLC grade), N,N¹-dicyclohexyl carbodiimide (DCC), N,N-dimethylglycine, polyethylene glycol 400 (PEG 400), formic acid, acetyl chloride, 3-dimethylaminopropionic acid hydrochloride, 1,8-diazabicyclo[5.4.0]undec-7-ene (DBU), and sodium sulfate (NaSO₄) anhydrous were purchased through VWR (West Chester, Pa.). Propylene glycol (PG), olivetol, absolute ethanol, triethylamine trihydrofluoride, 2-[2-92-methoxyethoxy)ethoxy]acetic acid, methyl (R)-(+)-2,2-dimethyl-1,3-dioxolane-4-carboxylate, tetrahydrofuran (THF), triphosgene, L-(t-butyldimethylsilyloxy)lactic acid and Hanks' balanced salts modified powder were purchased from Sigma-Aldrich (St. Louis, Mo.). mono-Fmoc-1,4-butanediamine hydrochloride was purchased from Novabiochem (San Diego, Calif.). Ethyl acetate, hexane, and dichloromethane (DCM) were obtained from the University of Kentucky Chemical Stores (Lexington, Ky.). (+)-(1S,4R)-p-Mentha-2,8-dien-1-ol and olivetol were purchased from Norac, Inc. (Azusa, Calif.). Carbopol® 980 was obtained from Noveon, Inc. (Cleveland, Ohio). Cannabidiol was purchased from Cayman Chemical Company (Ann Arbor, Mich.). Nanopure water was obtained from a Barnstead NANOpure® Diamond™ Ultrapure water filtration system (Dubuque, Iowa). Argon and pre-purified nitrogen were purchased from Scott Gross Company (Lexington, Ky.). The compound 3,6,9,12-tetraoxatridecanoic acid was synthesized according to the procedures found in *Macromolecules*, 39 (12), 3978-3979, 2006.

4.0 Synthesis of Cannabidiol Prodrugs 4.1 Synthesis of ALL00101 (CBD bis(3-(dimethylamino) propionate)) and ALL00150 (CBD 3-(dimethylamino)propionate)

Cannabidiol (100 mg, 0.00032 mol), 3-dimethylaminopropionic acid hydrochloride (123 mg, 0.00080 mol), and DMAP (117 mg, 0.00096 mol) were combined in 1 mL dry dichloromethane. The solution was stirred for 5 min at ambient temperature. DCC (198 mg, 0.00096 mol) was added to the mixture. The mixture was allowed to stir for 5 h at ambient temperature. Hexane was added and the precipitate removed by filtration. The solution was reduced to a small volume under nitrogen. ALL00101 and ALL00150 were separated and isolated using a semi-preparatory $C_8$ column with ACN: water (70:30). ACN was removed from the eluent fraction for each fraction by rotary evaporation. The remaining aqueous layer was partitioned with DCM and the DCM dried over sodium sulfate. DCM was removed under a nitrogen stream and vacuum. The purified products appeared as transparent, viscous oil with light amber color.

ALL00101 was analyzed by LC/MS (Waters; Milford, Mass.) in electrospray positive mode. Masses were observed at 513.42 (M+1, 70%), 257.34 (100%) and 123.06 (15%).

For ALL00150, the $^1$H NMR (400 MHz, CDCl$_3$) was as follows: δ=6.55 (1H, br s, ArH); 6.40 (1H, d, J=1.8, ArH); 5.98 (1H, br s, OH); 5.53 (1H, br s, H-2); 4.59-4.62 (1H, m); 4.45 (1H, br s); 3.45-3.59 (1H, m, H-3); 2.60-2.83 (4H, m); 2.41-2.55 (3H, m); 2.30 (6H, s, NMe$_2$); 2.16-2.27 (1H, m); 2.03-2.12 (1H, m); 1.70-1.84 (2H, m); 1.77 (3H, br s, 7-Me); 1.52-1.62 (2H, m); 1.61 (3H, s, 10-Me); 1.24-1.38 (4H, m); 0.88 (3H, t, J=7.0, CH$_2$CH$_3$)

4.2 Synthesis of ALL00105 (CBD bis(N,N-dimethylglycinate)) and ALL00148 (CBD N,N-dimethylglycinate)

Cannabidiol (200 mg, 0.00064 mol), N,N-dimethylglycine (196.8 mg, 0.00191 mol), and DMAP (38.9 mg, 0.00032 mol) were combined in 1 mL dry dichloromethane. The solution was stirred for 5 min at ambient temperature. DCC (459.3 mg, 0.00223 mol) was added to mixture. The mixture was allowed to stir overnight at ambient temperature. Hexane was added and precipitate removed by filtration. The solution was reduced to a small volume under nitrogen. ALL00105 and ALL00148 were separated and isolated using a semi-preparatory $C_8$ column with ACN:water (75:25). ACN was removed from the eluent fraction for each fraction by rotary evaporation. The remaining aqueous layer was partitioned with DCM and DCM dried over sodium sulfate. DCM was removed under a nitrogen stream and vacuum. The purified products appeared as transparent, viscous oil with light amber color.

ALL00105 was analyzed by LC/MS in electrospray positive mode. Masses were observed at 485.31 (M+1).

ALL00148 was analyzed by LC/MS in electrospray positive mode. Masses were observed at 417.15 (M+18, 30%), 315.23 (CBD+1, 100%).

4.3 Synthesis of ALL00131 (CBD 3,6,9,12-tetraoxatridecanoate) and ALL00132 (CBD di(3,6,9,12-tetraoxatridecanoate))

Cannabidiol (100 mg, 0.00033 mol), 3,6,9,12-Tetraoxatridecanoic acid (98.9 mg, 0.00045 mol) prepared according to *Macromolecules*, 39 (12), 3978-3979, 2006, and DMAP (11.7 mg, 0.00010 mol) were combined in 1 mL dry dichloromethane. The solution was stirred for 5 min at ambient temperature. DCC (111.4 mg, 0.00046 mol) was added to the mixture. The mixture was allowed to stir for 2 h at ambient temperature. Hexane was added and precipitate removed by filtration. The solution was reduced to a small volume under nitrogen. ALL00131 and ALL00132 were separated and isolated using a semi-preparatory silica column with hexane: ethyl acetate gradient. Solvent from each collected fraction was removed under vacuum. The purified products appeared as transparent, viscous oil with light amber color.

For ALL00131, the $^1$H NMR (400 MHz, CDCl$_3$) was as follows: δ=6.56 (1H, br s, ArH); 6.43 (1H, d, J=1.8, ArH); 6.01 (1H, br s, OH); 5.53 (1H, br s, H-2); 4.58-4.62 (1H, m); 4.43 (1H, br s); 4.35 (2H, br s, OCH$_2$CO$_2$); 3.76-3.86 (2H, m, PEG); 3.63-3.76 (8H, m, PEG); 3.54-3.57 (2H, m, PEG); 3.47 (1H, br s, H-3); 3.38 (s, 3H, CH$_2$OCH$_3$); 2.47-2.53 (2H, m, benzylic CH$_2$); 2.40-2.47 (1H, m); 2.14-2.25 (1H, m); 2.02-2.14 (1H, m); 1.65-1.86 (2H, m); 1.77 (3H, br s, 7-Me); 1.52-1.64 (2H, m); 1.58 (3H, s, 10-Me); 1.23-1.37 (4H, m); 0.88 (3H, t, J=7.0, CH$_2$CH$_3$).

For ALL00132, the $^1$H NMR (400 MHz, CDCl$_3$) was as follows: δ=6.75 (2H, s, ArH); 5.18 (1H, br s, H-2); 4.52-4.55 (1H, m); 4.42-4.45 (1H, m); 4.37, 4.34 and 4.22 (4H, br singlets, OCH$_2$CO$_2$); 3.76-3.86 (4H, m, PEG); 3.63-3.76 (16H, m, PEG); 3.53-3.57 (4H, m, PEG); 3.43-3.51 (1H, m, H-3); 3.38 (s, 6H, CH$_2$OCH$_3$); 2.51-2.62 (3H, m); 2.07-2.20 (1H, m); 1.97-2.06 (1H, m); 1.67-1.82 (2H, m); 1.66 (3H, br s, 7-Me); 1.52-1.63 (2H, m); 1.54 (3H, s, 10-Me); 1.23-1.38 (4H, m); 0.88 (3H, t, J=7.0, CH$_2$CH$_3$)

4.4 Synthesis of ALL00135 (CBD 4-aminobutyl carbamate) and ALL00136 (CBD bis(4-aminobutyl carbamate))

To a stirred solution of mono-Fmoc-1,4-butanediamine hydrochloride (461 mg, 1.33 mmol) in saturated NaHCO$_3$ aqueous solution (33.3 mL) and dichloromethane (22.2 mL) was added to triphosgene (592 mg, 2.0 mmol) in dichloromethane (5 mL) at ambient temperature. After stirring for 1 h, the product was extracted with dichloromethane (40 mL), and dichloromethane layer was dried over anhydrous Na$_2$SO$_4$ and concentrated. The residue was dissolved in ethyl acetate and product was precipitated with addition of hexane. Fmoc-4-aminobutyl isocyanate was collected by filtration as a white solid (305 mg, 68%).

Cannabidiol (44 mg, 0.00014 mol), Fmoc-4-aminobutyl isocyanate (68.0 mg, 0.00020 mol), and TEA (20 mg, 0.00038 mol) were combined in 2 mL dry dichloromethane under argon. The solution was allowed to stir overnight. The reaction mix was filtered. The protected compounds were separated and isolated using a semi-preparatory silica column with hexane:ethyl acetate gradient. The solvent from each collected fraction was taken to dryness under a nitrogen stream and reconstituted in THF.

Solutions of DBU (diluted 100-fold in THF) and octanethiol (diluted 10-fold in THF) were prepared. DBU solution (0.2 mL) and ocatanethiol solution (0.1 mL) were added to each solution containing a protected compound and stirred for 0.5-1 h. ALL00135 and ALL00136 were isolated using silica column chromatography and eluted with DCM:

methanol (80:20). The purified products appeared as transparent, viscous oil with light amber color.

ALL00135 was analyzed by LC/MS in electrospray positive mode. Masses were observed at 429.26 (M+1, 100%), 315.16 (CBD+1, 65%), and 153.13 (22%).

ALL00136 was analyzed by LC/MS in electrospray positive mode. Masses were observed at 543.32 (M+1, 30%), 315.16 (CBD+1, 70%), 292.76 (100%) and 272.24 (45%).

4.5 Synthesis of ALL00137 (CBD (S)-2,3-dihydroxypropanoate) and ALL00139 (CBD bis((S)-2,3-dihydroxypropanoate))

Cannabidiol (100 mg, 0.00032 mol), (S)-2,2-dimethyl-1,3-dioxalane-4-carboxylate (151.4 mg, 0.00035 mol), and DMAP (11.7 mg, 0.00010 mol) were combined in 1 mL dry dichloromethane. The solution was stirred for 5 min at ambient temperature. DCC (92.3 mg, 0.00045 mol) was added to the mixture. The mixture was allowed to stir overnight at ambient temperature. Hexane was added and precipitate removed by filtration. The solution was reduced to a small volume under nitrogen. Acetonides of ALL00137 and ALL00139 were separated and isolated using a semi-preparatory silica column with hexane:ethyl acetate gradient. The solvent from each collected fraction was removed under vacuum. The purified products appeared as transparent, viscous oil with light amber color. Acetonides of ALL00137 and ALL00139 were deprotected using 1-octanethiol/zinc triflate and purified using silica column chromatography (HPLC) with hexane:ethyl acetate (7:3).

ALL00137 was analyzed by LC/MS in electrospray positive mode. Masses were observed at 420.25 (M+18, 100%), 403.18 (M+1, 65%), 315.23 (CBD+1, 15%).

ALL00139 was analyzed by LC/MS in electrospray positive mode. Masses were observed at 508.23 (M+18, 100%), 491.15 (M+1, 18%), 315.16 (CBD+1, 5%).

4.6 Synthesis of ALL00140 (CBD 2-[2-(2-methoxyethoxy)ethoxy]acetate) and ALL00141 (CBD bis(2-[2-(2-methoxyethoxy)ethoxy]acetate))

Cannabidiol (105 mg, 0.00033 mol), 2-[2-(2-methoxyethoxy)ethoxy]acetic acid (83.3 mg, 0.00047 mol), and DMAP (12.3 mg, 0.00011 mol) were combined in 1 mL dry dichloromethane. The solution was stirred for 5 min at ambient temperature. DCC (117 mg, 0.00056 mol) was added to the mixture. The mixture was allowed to stir for 5 h at ambient temperature. Hexane was added and precipitate removed by filtration. The solution was reduced to a small volume under nitrogen. ALL00140 and ALL00141 were separated and isolated using a semi-preparatory silica column with hexane:ethyl acetate gradient. The solvent from each collected fraction was removed under vacuum. The purified products appeared as transparent, viscous oil with light amber color.

ALL00140 was analyzed by LC/MS in electrospray positive mode. Masses were observed at 492.37 (M+18, 100%) and 475.37 (M+1, 35%).

ALL00141 was analyzed by LC/MS in electrospray positive mode. Masses were observed at 652.51 (M+18, 100%) and 635.52 (M+1, 10%).

4.7 Synthesis of ALL00142 (CBD Diacetate)

Cannabidiol (42 mg, 0.00013 mol), acetyl chloride (26.3 mg, 0.00033 mol), and TEA (35 mg, 0.00039 mol) were combined in 0.5 mL dry dichloromethane. The solution was allowed to stir overnight. Hexane was added and reaction mix filtered. ALL00142 was isolated using silica column chromatography and hexane:ethyl acetate (9:1). The purified product appeared as transparent, viscous oil with light amber color.

ALL00142 was analyzed by LC/MS in electrospray positive mode. Masses were observed at 416.22 (M+18, 100%), 399.14 (M+1, 10%).

4.8 Synthesis of ALL00143 (CBD Bis(Methyl Carbonate))

Cannabidiol (44 mg, 0.00013 mol), methyl chloroformate (31.7 mg, 0.00034 mol), and TEA (18.4 mg, 0.00035 mol) were combined in 2 mL dry dichloromethane. The solution was allowed to stir overnight. Hexane was added and the reaction mix filtered. ALL00143 was isolated using silica column chromatography and hexane:ethyl acetate (9:1). The purified product appeared as transparent, viscous oil with light amber color.

For ALL00143, the $^1$H NMR (400 MHz, CDCl$_3$) was as follows: δ=6.82 (2H, s, ArH); 5.17-5.21 (1H, m, H-2); 4.51-4.55 (1H, m); 4.42-4.46 (1H, m); 3.86 (6H, s, OCO$_2$CH$_3$); 3.60-3.68 (1H, m, H-3); 2.65-2.73 (1H, m); 2.53-2.59 (2H, m, benzylic CH$_2$); 2.16-2.28 (1H, m); 1.93-2.01 (1H, m); 1.66-1.81 (2H, m); 1.65 (3H, br s, 7-Me); 1.54-1.63 (2H, m); 1.58-1.60 (3H, m, 10-Me); 1.24-1.37 (4H, m); 0.88 (3H, t, J=7.0, CH$_2$CH$_3$).

4.9 Synthesis of ALL00145 (CBD Diformate) and ALL00146 (CBD Formate)

Cannabidiol (150 mg, 0.00043 mol), formic acid (59.25 mg, 0.00129 mol), and DMAP (36.6 mg, 0.00030 mol) were combined in 1 mL dry dichloromethane. The solution was stirred for 5 min at ambient temperature. DCC (150 mg, 0.00142 mol) was added to the mixture. The mixture was allowed to stir for 4 h at ambient temperature. Hexane was added and precipitate removed by filtration. The solution was reduced to a small volume under nitrogen. ALL00145 and ALL00146 were separated and isolated using a semi-preparatory silica column with hexane:ethyl acetate (97:3). The solvent from each collected fraction was removed under vacuum. The purified products appeared as transparent, viscous oil with light amber color.

For ALL00145, the $^1$H NMR (400 MHz, CDCl$_3$) was as follows: δ=8.16 (2H, br s, CHO); 6.78 (2H, s, ArH); 5.09-5.13 (1H, m, H-2); 4.52-4.56 (1H, m); 4.41-4.45 (1H, m); 3.60-3.69 (1H, m, H-3); 2.64-2.72 (1H, m); 2.54-2.62 (2H, m, benzylic CH$_2$); 2.08-2.20 (1H, m); 1.96-2.05 (1H, m); 1.75-1.82 (1H, m); 1.66-1.75 (1H, m); 1.654 (3H, br s, 7-Me); 1.65-1.54 (2H, m); 1.58-1.60 (3H, m, 10-Me); 1.24-1.39 (4H, m); 0.89 (3H, t, J=7.0, CH$_2$CH$_3$).

For ALL00146, the $^1$H NMR (400 MHz, CDCl$_3$) was as follows: δ=8.18 (1H, s, CHO); 6.78 (1H, br s, ArH); 6.37 (1H, d, J=1.5, ArH); 6.10 (1H, br s, OH); 5.53 (1H, br s, H-2); 4.55-4.58 (1H, m); 4.36 (1H, br s); 3.62-3.72 (1H, m, H-3); 2.48-2.54 (2H, m, benzylic CH$_2$); 2.41-2.46 (1H, m); 2.17-2.30 (1H, m); 2.05-2.15 (1H, m); 1.68-1.86 (2H, m); 1.79 (3H, br s, 7-Me); 1.53-1.63 (2H, m); 1.60 (3H, br s, 10-Me); 1.24-1.38 (4H, m); 0.88 (3H, t, J=7.0, CH$_2$CH$_3$).

4.10 Synthesis ALL00147 (CBD Diglycolate)

To a stirred solution of cannabidiol (31.4 mg, 0.1 mmol) and (t-butyldimethylsilyloxy)acetic acid (57.5 mg, 0.26 mmol) in dichloromethane (0.4 mL), 4-dimethylaminopyridine (10.3 mg, 0.05 mmol) was added followed by N,N'-dicyclohexylcarbodiimide (61.9 mg, 0.3 mmol). The mixture was stirred at ambient temperature for 4 h. The mixture was diluted with hexane (0.4 mL), filtered, concentrated under a reduced pressure, and chromatographed on silica gel with hexane-ethyl acetate (gradient 40:1, 20:1, 10:1) to afford CBD bis((t-butyldimethylsilyloxy)acetate) (44.4 mg, 67.4%) as an oil.

Cannabidiol bis((t-butyldimethylsilyloxy)acetate) was dissolved in dichloromethane (0.2 mL), cooled to −15° C. and treated with 0.2 mL of cold 2 M solution of triethylamine trihydrofluoride. The reaction mixture was left at 5° C. for 65 h. The mixture was poured into an excess of aqueous saturated sodium bicarbonate/ethyl acetate cooled to 0° C. with vigorous stirring. The aqueous layer was extracted twice with ethyl acetate, combined organic extracts were dried over anhydrous sodium sulfate and concentrated. Residue was chromatographed on silica gel with hexane-ethyl acetate (gradient 3:1, 2:1, 1:1) to afford 18.9 mg (65%) of cannabidiol diglycolate (ALL00147) as an oil.

For ALL00147, the $^1$H NMR (400 MHz, CDCl$_3$) was as follows: δ=6.79 (2H, s, ArH); 5.17 (1H, br s, H-2); 4.52-4.57 (1H, m); 4.41-4.47 (1H, m); 4.39, 4.36 and 4.22 (4H, br singlets, OCH$_2$CO$_2$); 3.42-3.50 (1H, m, H-3); 2.48-2.62 (3H, m); 2.36 (2H, t, J=5.6, OH); 2.08-2.20 (1H, m); 1.99-2.08 (1H, m); 1.68-1.83 (2H, m); 1.66 (3H, br s, 7-Me); 1.57-1.65 (2H, m); 1.52-1.54 (3H, s, 10-Me); 1.26-1.38 (4H, m); 0.89 (3H, t, J=7.0, CH$_2$CH$_3$).

4.11 Synthesis ALL00149 (CBD Glycolate)

To a stirred solution of cannabidiol (125.8 mg, 0.4 mmol) and (t-butyldimethylsilyloxy)acetic acid (112.9 mg, 0.51 mmol) in dry dichloromethane (1 mL) was added of 4-dimethylaminopyridine (6.2 mg, 0.03 mmol) followed by N,N'-dicyclohexylcarbodiimide (123.8 mg, 0.6 mmol). The mixture was stirred at ambient temperature for 1 h. Additional amounts of the acid (26.6 mg) and N,N'-dicyclohexylcarbodiimide (31 mg) were added and stirring was continued for 1 h. Mixture was diluted with hexane (2 mL), filtered, and concentrated. The crude product was purified by preparative reverse phase HPLC (C8 column) with acetonitrile-water to afford cannabidiol (t-butyldimethylsilyloxy)acetate as an oil.

Cannabidiol (t-butyldimethylsilyloxy)acetate (80 mg) was dissolved in dry dichloromethane (0.25 mL), cooled to −15° C. and treated with 0.25 mL of cold 2 M solution of triethylamine trihydrofluoride in dichloromethane. The reaction mixture was left at 5° C. for 65 h. The mixture was poured to an excess of aqueous saturated sodium bicarbonate/ethyl acetate cooled to 0° C. with vigorous stirring. Aqueous layer was extracted twice with ethyl acetate, the combined organic extracts were washed with brine, dried over anhydrous sodium sulfate and concentrated. The residue was chromatographed on silica gel with hexane-ethyl acetate (gradient 10:1, 4:1, 3:1) to afford 58 mg (95%) of cannabidiol glycolate (ALL00149) as an oil.

For ALL00149, the $^1$H NMR (400 MHz, CDCl$_3$) was as follows: δ=6.59 (1H, br s, ArH); 6.43 (1H, d, J=1.8, ArH); 6.03 (1H, br s, OH); 5.53 (1H, br s, H-2); 4.59-4.62 (1H, m); 4.44 (1H, br s); 4.30-4.40 (2H, m, OCH$_2$CO$_2$); 3.46 (1H, br s, H-3); 2.48-2.54 (2H, m, benzylic CH$_2$); 2.40-2.47 (1H, m); 2.39 (2H, t, J=5.6, OH); 2.15-2.29 (1H, m); 2.04-2.14 (1H, m); 1.67-1.86 (2H, m); 1.78 (3H, br s, 7-Me); 1.53-1.63 (2H, m); 1.57 (3H, br s, 10-Me); 1.23-1.37 (4H, m); 0.88 (3H, t, J=7.0, CH$_2$CH$_3$).

4.12 Synthesis ALL00151 (CBD L-Lactate)

To a stirred solution of cannabidiol (220.1 mg, 0.7 mmol) and L-(t-butyldimethylsilyl)lactic acid (299.4 mg, 1.26 mmol) in dry dichloromethane (2 mL) was added 4-dimethylaminopyridine (14.4 mg, 0.07 mmol) followed by N,N'-dicyclohexylcarbodiimide (310.5 mg, 1.505 mmol). The mixture was stirred at ambient temperature for 1 h. Additional amounts of the acid (45 mg) and N,N'-dicyclohexylcarbodiimide (60 mg) were added and stirring was continued for 1.5 h. The mixture was diluted with hexane (3 mL), filtered, and concentrated. The crude product was purified by preparative reverse phase HPLC (C8 column) with acetonitrile-water to afford cannabidiol L-(t-butyldimethylsilyl)lactate as an oil and cannabidiol bis(L-(t-butyldimethylsilyl))lactate (an intermediate for cannabidiol di(L-lactate)).

Cannabidiol L-(t-butyldimethylsilyl)lactate (15.1 mg) was dissolved in dry dichloromethane (0.1 mL), cooled to −15° C. and treated with 0.1 mL of cold 2M solution of triethylamine trihydrofluoride in dichloromethane. The reaction mixture was left at 5° C. for 65 h. The mixture was poured to an excess of aqueous saturated sodium bicarbonate/ethyl acetate cooled to 0° C. with vigorous stirring. The aqueous layer was extracted twice with ethyl acetate. The combined organic extracts were washed with brine, dried over anhydrous sodium sulfate and concentrated. The residue was chromatographed on silica gel with hexane-ethyl acetate (gradient 10:1, 6:1, 4:1) to afford 9.8 mg (82%) of CBD L-lactate (ALL00151) as an oil.

For ALL00151, the $^1$H NMR (400 MHz, CDCl$_3$) was as follows: δ=6.59 (1H, br s, ArH); 6.37 (1H, d, J=1.8, ArH); 6.02 (1H, br s, OH); 5.52 (1H, br s, H-2); 4.60-4.63 (1H, m); 4.44-4.52 (1H, m, OCHCO$_2$); 4.44 (1H, br s); 3.41 (1H, br s, H-3); 2.77 (1H, d, J=5.4, OH); 2.47-2.53 (2H, m, benzylic CH$_2$); 2.40-2.48 (1H, m); 2.15-2.29 (1H, m); 2.03-2.14 (1H, m); 1.67-1.86 (2H, m); 1.78 (3H, br s, 7-Me); 1.53-1.64 (5H, m, aliphatic H and OCH(CH$_3$)CO$_2$); 1.59 (3H, br s, 10-Me); 1.23-1.38 (4H, m); 0.88 (3$\overline{H}$, t, J=7.0, CH$_2$CH$_3$).

4.13 Proposed CBD-Hyaluronic Acid

One or both of the hydroxyl groups on the cannabidiol molecule can be functionalized with various substituents (e.g., hyaluronic acid, lactic acid and glycolic acid) and optionally combined with dermatologically acceptable vehicles to form a cosmetic composition for application to the skin of mammal, such as a human. The scheme below represents a possible method for attachment of cannabidiol to hyaluronic acid using carbonate linkage and the TBDMS ether as a protective group. It may be anticipated that most of the primary hydroxyl group of the polymer would be involved in the formation of the linkage to the drug. Additional and/or different sets of protective group/deprotection methods could be used.

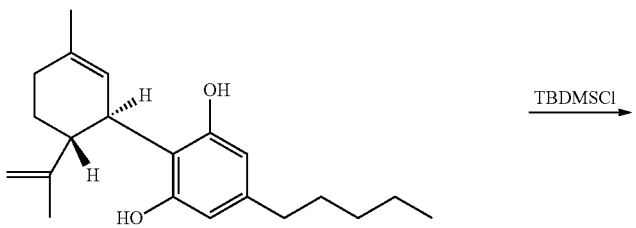

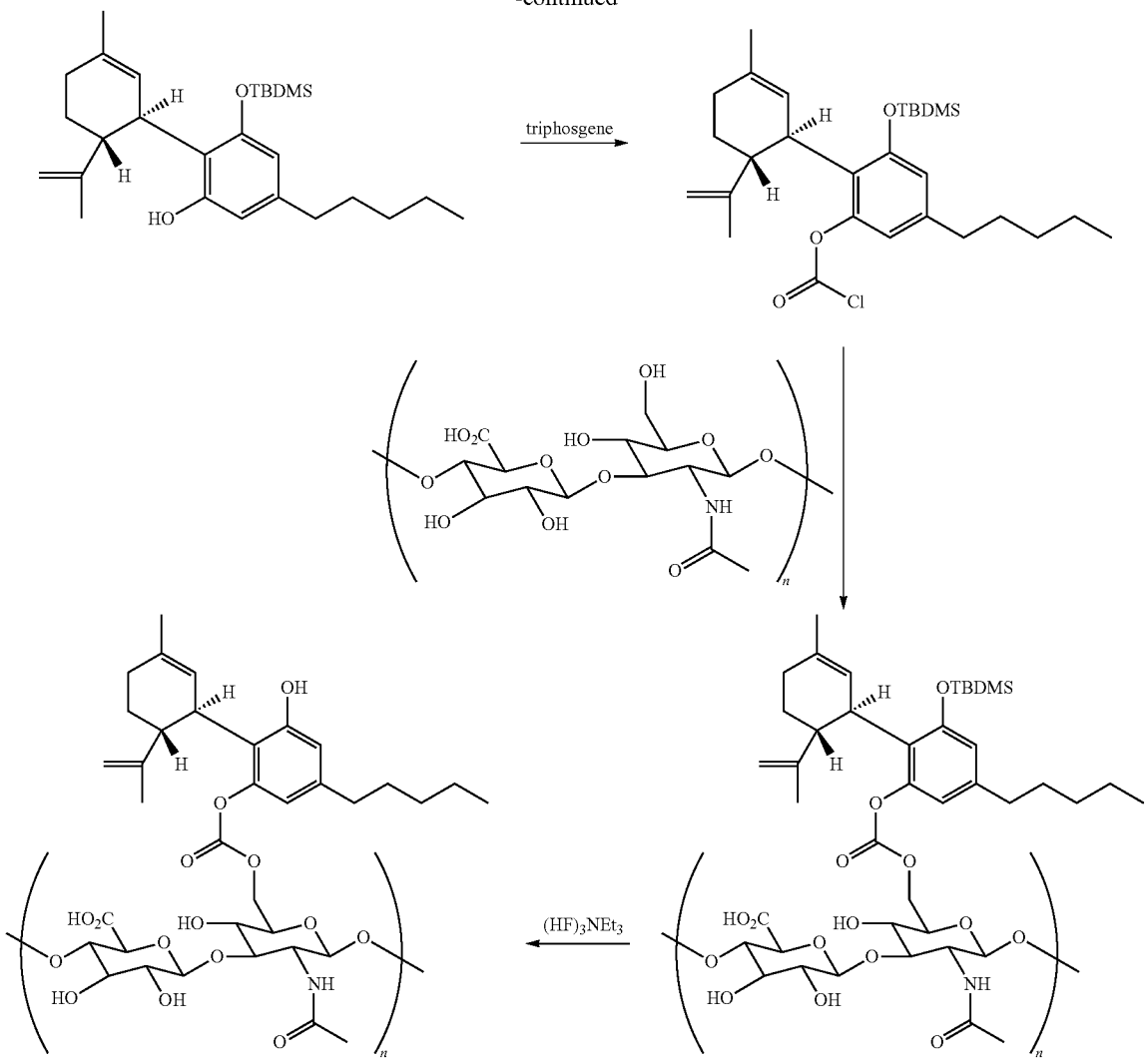

Also, glycolic acid and lactic acid could be attached to either or cannabidiol hydroxyl groups through an ester linkage or with the carbonate linkage by use of the 2-hydroxy group of acids. Cannabidiol could be also attached in a similar manner to a polymeric compound, such as hyaluronic acid. Using an additional spacer (e.g. 2-aminoethanol or glycine), the attachment in all cases could also be achieved through a carbamate linkage.

One of skill in the art would also recognize that, for example, cannabidiol may be attached to carboxylic groups of hyaluronic acid through the ester linkage or through a carbamate linkage through the use of an additional spacer (e.g. 2-aminoethanol). In a further embodiment, an additional spacer may also be used when attaching cannabidiol to hydroxyl groups of hyaluronic acid.

5.0 Plasma Stability Studies

An approximated 1 mg/mL stock solution of each prodrug was prepared in 100 μL of ethanol and 900 μL of acetonitrile. Ten (10) μL of stock was spiked into 1 mL of plasma and vortexed. The samples were kept sealed in an amber vial and samples were obtained to analyze for bioconversion to parent drug.

6.0 In Vitro Skin Permeation Studies 6.1 Preparation of Receiver Fluid 1

One (1) L of receiver fluid was prepared by measuring 1 L of nanopure water into a graduated cylinder. 90% of the water was added to an Erlenmeyer flask. Hanks' salts (1 bottle) were added to the water along with 5.96 g of HEPES and 0.35 g of sodium bicarbonate. The pH of the solution was adjusted with 1 N sodium hydroxide solution to pH 7.4. The remaining water was added and the receiver fluid was filtered through a 0.2μ filter (Millipore, Billerica, Mass.). Fifty (50) mg of gentamicin was added to the filtered receiver fluid and 400 mL of the receiver fluid was removed and replaced with 400 mL of PEG 400.

6.2 Preparation of Receiver Fluid 2

The receiver fluid was prepared by measuring 600 mL of nanopure $H_2O$ into a graduated cylinder. The $H_2O$ was filtered through a 0.2μ filter (Millipore, Billerica, Mass.). Fifty (50) mg of gentamicin was added to the filtered $H_2O$ and 400 mL of PEG 400 was added.

6.3.1 Preparation of Drug Formulation (Example 2)

The prodrugs were made up in a solution of 45:4:1 PG:$H_2O$:IPM. For this solution, the appropriate amount of drug was weighed into a glass silanized culture tube and IPM was added, the 50 μL of PG to coat the drug, then an additional 247 μL PG was added and the donor solution was vortexed again. Finally 26 μL of water was added. The gel formulation resulted from the mixing of absolute ethanol, nanopure water, IPM, Carbopol® 980, 0.1 N sodium hydroxide solution and the respective drug.

6.3.2 Preparation of Drug Formulation (Example 2A)

The gel formulation was comprised of absolute ethanol, nanopure water, IPM, Carbopol® 980, 0.1 sodium hydroxide solution and respective drug. The anhydrous gel was comprised of absolute ethanol, PEG monoethyl ether 550, Klucel® hydroxypropylcellulose, and respective drug.

6.4 Permeation Experiments

Dermatomed skin harvested from abdominoplasty, stored at −20° C., was used for the experiments. A PermeGear flow-through (In-Line, Hellertown, Pa.) diffusion cell system was used for the skin permeation studies.

Diffusion cells were kept at 32° C. with a circulating water bath. Human epidermal skin was arranged in the diffusion cell with stratum corneum (upper layer of skin) facing the donor compartment. The permeation area of the skin was 0.95 cm². The data was collected from a human skin donor with three diffusion cells per treatment.

The receiver solution was HEPES-buffered Hanks' balanced salts with gentamicin containing 40% PEG 400 at a pH of 7.4 or 40% aqueous PEG 400 and flow rate was adjusted to 0.8 mL/h. Each cell was charged with 0.10 mL of the respective drug formulation (donor solution) or 50 μL of gel formulation which was rubbed into the skin for 15 sec with a Teflon coated rod. The formulation was applied to ensure complete coverage. The formulation was applied to ensure complete coverage. Diffusion cells were covered with a stopper or cap for the duration of the study.

Samples were collected into scintillation vials in 3 h increments for either 24, 30, or 42 h. All the samples were stored at 4° C. until extracted. An aliquot (0.5 mL) of the diffusion sample was placed into a silanized HPLC vial and 0.5 mL of acetonitrile was added to the sample, capped and vortexed.

At the end of the experiment, the skin tissue was removed from the diffusion cell, rinsed with nanopure water, and blotted dry with a paper towel. The skin was tape stripped twice using book tape (Scotch™, 3M, St. Paul, Minn.) to remove drug formulation adhering to the tissue surface. The area of skin in contact with the drug was cut out, chopped up and placed in a pre-weighed scintillation vial. Ten (10) mL of acetonitrile was added to the vial and drug was extracted from the skin by shaking at room temperature overnight. The following day a 1 mL aliquot was removed transferred into a silanized HPLC vial for analysis. At the end of the experiments dosed with a gel, the skin tissue was rinsed 3 times with nanopure water for 10 s each and wiped off with an alcohol pad. The entire piece of skin was blotted dry and tape stripped twice using book tape 845 (Scotch™, 3M, St. Paul, Minn.) to remove any drug formulation adhering to the surface. The skin was rinsed an additional time with nanopure water and blotted dry again. The area of skin in contact with the drug was removed, minced with a scalpel, and placed in a pre-weighed scintillation vial. Drug was extracted from the area of skin in contact with the drug by equilibrating with 10 mL of ACN while shaking in a water bath overnight.

At the end of the experiment, a 0.01 mL aliquot of the donor solution was removed and added to a scintillation vial containing 10 mL of acetonitrile. The vials were vortexed and an aliquot of 1 mL was removed and transferred into a silanized HPLC vial for analysis. At the end of the experiments dosed with a gel, the donor compartment was rinsed 5 times with a known amount of nanopure water or ACN and then an aliquot of the nanopure water or ACN were diluted with ACN. The vials were vortexed and an aliquot of 1 mL was removed and transferred into a silanized HPLC vial for analysis.

7.0.1 Analytical Method (Example 2)

| | |
|---|---|
| Column | Brownlee ® $C_8$ reversed phase Spheri 5 μm, (4.6 × 220 mm) column with a Brownlee ® $C_8$ reversed phase 7 μm (3.2 × 150 mm) guard column |
| Mobile phase | 55:45 acetonitrile:0.05% trifluroacetic acid with 5% acetonitrile, 60:40 acetonitrile:0.05% trifluroacetic acid with 5% acetonitrile, 65:35 acetonitrile:0.1% trifluroacetic acid with 5% acetonitrile 70:30 acetonitrile:0.05% trifluroacetic acid with 5% acetonitrile, and 70:30 acetonitrile:0.1% trifluroacetic acid with 5% acetonitrile |
| Flow rate | 1.5 mL/min |
| Wavelength | 210 nm |
| Injection volume | 100 μL (diffusion samples and respective standards) 20 μL (skin samples, donor samples, and respective standards) |
| Run time | 14-18 min |
| Retention times | cannabidiol = 6.3, 7.0, 7.9, 9.2, 12.2, 16.3 min ALL00101 = 6.2 min ALL00105 = 5.9 min ALL00131 = 11.0 min ALL00132 = 12.9 min ALL00140 = 15.3 min ALL00145 = 13.8 min ALL00146 = 8.3, 10.2 min ALL00147 = 4.2 min ALL00148 = 6.6, 7.9 min ALL00149 = 5.2 min ALL00150 = 7.9 min |

7.0.2 Analytical Method (Example 2A)

| | |
|---|---|
| Column | Brownlee ® $C_8$ reversed phase Spheri 5 μm, (4.6 × 220 mm) column with a Brownlee ® $C_8$ reversed phase 7 μm (3.2 × 150 mm) guard column |
| Mobile phase | 65:35 acetonitrile:0.1% trifluroacetic acid with 5% acetonitrile and 75:25 acetonitrile:0.1% trifluroacetic acid with 5% acetonitrile |
| Flow rate | 1.5 mL/min |
| Wavelength | 210 nm |
| Injection volume | 100 μL (diffusion samples and respective standards) 20 μL (skin samples, donor samples, and respective standards) |

-continued

| | |
|---|---|
| Run time | 8-12 min |
| Retention times | cannabidiol = 4.8, 10.1 min |
| | ALL00146 = 6.1 min |
| | ALL00150 = 7.8 min |

7.0.3 Analytical Method (Example 2B)

| | |
|---|---|
| Column | Brownlee ® C₈ reversed phase Spheri 5 μm, (4.6 × 220 mm) column with a Brownlee ® C₈ reversed phase 7 μm (3.2 × 150 mm) guard column |
| Mobile phase | 65:35 acetonitrile:0.1% trifluroacetic acid with 5% acetonitrile |
| Flow rate | 1.5 mL/min |
| Wavelength | 210 nm |
| Injection volume | 100 μL (diffusion samples and respective standards) 20 μL (skin samples, donor samples, and respective standards) |
| Run time | 12 min |
| Retention times | cannabidiol = 10.2 min |
| | ALL00147 = 4.3 min |
| | ALL00149 = 5.6 min |

8.0 Data Analysis

The cumulative quantity of drug collected in the receiver compartment was plotted as a function of time. The flux value for a given experiment was obtained from the slope of a steady-state portion of the cumulative amount of drug permeated vs. time plot. Lag time was obtained from the x-intercept of the steady state portion of the cumulative amount of drug permeated vs. time plot. In Tables 16-19 and 21-23, the combined results of the delivered prodrug and cannabidiol from the prodrug are listed as "total cannabidiol." These values represent the data as total cannabidiol equivalents delivered in the form of cannabidiol and/or prodrug.

Section III. Results

The cannabidiol prodrugs synthesized in Example 2 were all oily compounds.

In gel formulation, ALL00101 permeated through the skin as mono-substituted prodrug (ALL00150) only. ALL00101 did not increase the flux compared to cannabidiol. ALL00101 was detected in the skin as trace small amounts of intact prodrug but mostly as mono-substituted prodrug, ALL00150, and cannabidiol. Total skin concentrations were higher compared to cannabidiol. Lag time was decreased compared to cannabidiol.

In donor solution, ALL00105 permeated through the skin as mono-substituted prodrug (ALL00148) and cannabidiol. ALL00105 did not increase the flux compared to cannabidiol. ALL00105 was detected in the skin as mono-substituted prodrug, ALL00148, and cannabidiol. Total skin concentrations were higher compared to cannabidiol. Lag time was not decreased compared to cannabidiol.

In donor solution, ALL00131 permeated through the skin as intact prodrug and cannabidiol. ALL00131 did not increase the flux compared to cannabidiol. ALL00131 was detected in the skin only as prodrug. Total skin concentrations were not higher compared to cannabidiol. Lag time was similar to cannabidiol.

In donor solution, ALL00132 permeated through the skin as intact prodrug, mono-substituted prodrug (ALL00131), and cannabidiol. ALL00132 did not increase the flux compared to cannabidiol. ALL00132 was detected in the skin as prodrug and small amounts as mono-substituted prodrug, ALL00131. Total skin concentrations were not higher compared to cannabidiol. Lag time wasn't decreased compared to cannabidiol.

In donor solution, ALL00137 did not permeate through the skin or was below detection in the receiver samples. ALL00137 was detected in the skin as prodrug and trace amounts of cannabidiol. Total skin concentrations were not higher compared to cannabidiol.

In donor solution, ALL00140 permeated through the skin as intact prodrug and cannabidiol. ALL00140 did not increase the flux compared to cannabidiol. ALL00140 was detected mostly as prodrug in the skin with small amounts of cannabidiol. Total skin concentrations were not higher compared to cannabidiol. Lag time was slightly decreased compared to cannabidiol.

In donor solution, ALL00142 did not permeate through the skin or was below detection in the receiver samples. ALL00142 was detected in the skin only as intact prodrug. Total skin concentrations were not higher compared to cannabidiol.

In donor solution, ALL00143 did not permeate through the skin or was below detection in the receiver samples. ALL00143 was detected in the skin as prodrug and trace amounts of cannabidiol. Total skin concentrations were not higher compared to cannabidiol.

In donor solution, ALL00145 permeated through the skin as approximately 50% mono-substituted prodrug (ALL00146) and approximately 50% cannabidiol. ALL00145 did not increase the flux compared to cannabidiol. ALL00145 was detected in the skin as prodrug, mono-substituted prodrug, ALL00146, and cannabidiol. Total skin concentrations were higher compared to cannabidiol. Lag time wasn't decreased compared to cannabidiol.

In gel formulation, ALL00146 permeated through the skin through the skin as intact prodrug and cannabidiol. ALL00146 did slightly increase the flux compared to cannabidiol. ALL00146 was detected in the skin as intact prodrug and cannabidiol. Total skin concentrations were not higher compared to cannabidiol. Lag time was similar to cannabidiol.

In donor solution, ALL00147 permeated through the skin as intact prodrug, mono-substituted prodrug (ALL00149), and cannabidiol. ALL00147 did not increase the flux compared to cannabidiol. ALL00147 was detected in the skin as prodrug, mono-substituted prodrug, ALL00149, and cannabidiol. Total skin concentrations were not higher compared to cannabidiol. Lag time was not decreased compared to cannabidiol.

In gel formulation, ALL00148 permeated through the skin through the skin as intact prodrug only. ALL00148 did not increase the flux compared to cannabidiol. ALL00148 was detected in the skin as mostly intact prodrug and small amounts of cannabidiol. Total skin concentrations were higher compared to cannabidiol. Lag time was similar to cannabidiol.

Decreased lag time may benefit patients by delivering the drug more quickly which is beneficial for pain management and nausea. Long lag times are more useful for topical and follicular therapies where drug absorption is attenuated. Cannabidiol prodrugs may increase permeation more if drug solution solvent systems were optimized or if they were formulated with enhancers. Many of these prodrugs may be useful in targeting topical/follicular applications instead of transdermal applications. By targeting topical administration, drug delivery could focus on a localized delivery compared to a systemic delivery. Also, follicular delivery may be targeted for administration with or without microparticle formulations.

In gel formulation, ALL00146 permeated through the skin as cannabidiol only, no prodrug was detected in the receiver fluid. ALL00146 didn't increase the flux compared to cannabidiol. ALL00146 was detected in the skin as small amount of cannabidiol with the remaining being prodrug. Total skin concentrations were slightly higher compared to cannabidiol. Lag time was higher compared to cannabidiol.

In gel formulation, ALL00150 did not permeate through the skin. ALL00150 was detected in the skin as primarily ALL00150 with a small amount of cannabidiol. Total skin concentrations were higher compared to cannabidiol.

In an anhydrous gel formulation, ALL00150 did not permeate through the skin. ALL00150 was detected in the skin as ALL00150 and cannabidiol. Total skin concentrations were higher compared to cannabidiol.

Overall, concentrations of cannabidiol and ALL00150 in the skin treated with the anhydrous gel formulation were much lower compared to the ethanol based gel formulation.

In gel formulation for cannabidiol, ALL00147, and ALL00149 only one cell of each drug had detectable levels in the receiver fluid of the respective drug. However all three cells of each drug had detectable skin concentrations. Therefore the diffusion data reported here reflects the data collected.

ALL00147 permeated through the skin as cannabidiol (47.2%) and mono-prodrug, ALL00149 (45.6%) with a trace amount of ALL00147 (7.2%). ALL00147 did increase the flux compared to cannabidiol by 2 fold. ALL00147 was detected in the skin primarily as mono-prodrug, ALL00149 with a trace amount of ALL00147. Total skin concentrations weren't higher compared to cannabidiol.

ALL00149 permeated through the skin as primarily ALL00149 with a trace amount of cannabidiol. ALL00149 did increase the flux compared to cannabidiol by 1.4. ALL00149 was detected in the skin as primarily ALL00149 with a trace amount of cannabidiol. Total skin concentrations were higher compared to cannabidiol. Lag time of ALL00149 was lower compared to cannabidiol.

Section IV. Tables

TABLE 15

Cannabidiol and cannabidiol prodrugs

| Compound | LogP* | Molecular formula | Molecular weight |
|---|---|---|---|
| cannabidiol | 7.03 ± 0.37 | $C_{21}H_{30}O_2$ | 314.46 |
| ALL00101 | 7.47 ± 0.43 | $C_{31}H_{48}N_2O_6$ | 512.72 |
| ALL00105 | 7.14 ± 0.49 | $C_{29}H_{44}N_2O_4$ | 484.67 |
| ALL00131 | 6.57 ± 0.59 | $C_{30}H_{46}O_7$ | 518.68 |
| ALL00132 | 5.30 ± 0.78 | $C_{39}H_{62}O_{12}$ | 722.90 |
| ALL00135 | 6.82 ± 0.37 | $C_{26}H_{40}N_2O_3$ | 428.61 |
| ALL00136 | 6.28 ± 0.38 | $C_{31}H_{50}N_4O_4$ | 542.75 |
| ALL00137 | 6.40 ± 0.43 | $C_{24}H_{34}O_5$ | 402.52 |
| ALL00139 | 4.86 ± 0.52 | $C_{27}H_{38}O_8$ | 490.59 |
| ALL00140 | 6.93 ± 0.54 | $C_{28}H_{42}O_6$ | 474.63 |
| ALL00141 | 6.02 ± 0.69 | $C_{35}H_{54}O_{10}$ | 634.80 |
| ALL00142 | 7.16 ± 0.37 | $C_{25}H_{34}O_4$ | 398.54 |
| ALL00143 | 7.04 ± 0.51 | $C_{25}H_{34}O_6$ | 430.53 |
| ALL00145 | 6.57 ± 0.47 | $C_{23}H_{30}O_4$ | 370.48 |
| ALL00146 | 6.97 ± 0.41 | $C_{22}H_{30}O_3$ | 342.47 |
| ALL00147 | 5.57 ± 0.44 | $C_{25}H_{34}O_6$ | 430.53 |
| ALL00148 | 7.49 ± 0.42 | $C_{25}H_{37}NO_3$ | 399.57 |
| ALL00149 | 6.71 ± 0.40 | $C_{23}H_{32}O_4$ | 372.50 |
| ALL00150 | 7.66 ± 0.42 | $C_{26}H_{39}NO_3$ | 413.59 |
| ALL00151 | 7.05 ± 0.41 | $C_{24}H_{34}O_4$ | 386.52 |

*LogP calculated by ChemSketch 10.02 (Advanced Chemistry Development, Inc; Canada)

TABLE 16

Permeation data of CBD (n = 3), ALL00131 (n = 3), ALL00132 (n = 2), and ALL00140 (n = 3) in 90:8:2 PG:H2O:IPM donor solution with 60/40 Hanks'/PEG 400 receiver fluid

| Compound | 42 h skin conc (μmol/g) | 42 h cumulative amt (nmol) | Flux (nmol/cm$^2$/h) | Flux enhancement | Lag time (h) |
|---|---|---|---|---|---|
| cannabidiol (CBD) | 19.0 ± 12.8 | 154.4 ± 39.5 | 6.5 ± 0.7 | — | 14.2 ± 4.1 |
| total cannabidiol* | 12.5 ± 5.5 | 70.3 ± 20.4 | 2.8 ± 0.7 | 0.43 | 12.9 ± 1.6 |
| ALL00131 | 12.5 ± 5.5 | 54.9 ± 22.1 | 2.3 ± 0.8 | | 13.7 ± 1.9 |
| CBD from ALL00131 | ND | 15.4 ± 2.0 | 0.6 ± 0.1 | | 9.6 ± 3.0 |
| total cannabidiol* | 3.5 ± 1.7 | 59.5 ± 23.8 | 2.6 ± 0.5 | 0.40 | 14.9 ± 3.8 |
| ALL00132 | 2.9 ± 1.3 | 26.4 ± 17.0 | 1.4 ± 0.4 | | 19.2 ± 4.9 |
| ALL00131 from ALL00132 | 0.6 ± 0.1 | 23.0 ± 7.1 | 0.8 ± 0.2 | | 9.1 ± 3.3 |
| CBD from ALL00132 | ND | 10.0 ± 0.4 | 0.4 ± 0.1 | | 11.8 ± 4.2 |
| total cannabidiol* | 13.2 ± 6.9 | 58.1 ± 15.5 | 2.2 ± 0.5 | 0.33 | 11.2 ± 2.2 |
| ALL00140 | 12.7 ± 6.6 | 34.3 ± 15.5 | 1.3 ± 0.5 | | 12.6 ± 2.5 |
| CBD from ALL00140 | 0.5 ± 0.3 | 24.1 ± 3.3 | 0.9 ± 0.1 | | 9.0 ± 2.7 |

*total CBD = total cannabidiol equivalents delivered in the form of cannabidiol and/or prodrug Wherein "n" equals the number of skin samples tested.

TABLE 17

Permeation data of CBD (n = 3), ALL00137 (n = 3), ALL00142 (n = 3), and ALL00143 (n = 3) in 90:8:2 PG:H2O:IPM donor solution with 40% aqueous PEG 400 receiver fluid

| Compound | 30 h skin conc (μmol/g) | 30 h cumulative amt (nmol) | Flux (nmol/cm$^2$/h) | Flux enhancement | Lag time (h) |
|---|---|---|---|---|---|
| cannabidiol (CBD) | 10.5 ± 6.5 | 51.6 ± 9.1 | 3.9 ± 0.2 | — | 16.2 ± 1.9 |
| total cannabidiol* | 1.0 ± 0.5 | ND | ND | — | — |
| ALL00137 | 0.9 ± 0.3 | ND | ND | | — |
| CBD from ALL00137 | 0.3 ± 0.0 | ND | ND | | — |
| total cannabidiol* | 5.5 ± 0.3 | ND | ND | — | — |
| ALL00142 | 5.5 ± 0.3 | ND | ND | | — |
| CBD from ALL00142 | ND | ND | ND | | — |
| total cannabidiol* | 6.0 ± 3.2 | ND | ND | — | — |

TABLE 17-continued

Permeation data of CBD (n = 3), ALL00137 (n = 3), ALL00142 (n = 3), and ALL00143 (n = 3) in 90:8:2 PG:H2O:IPM donor solution with 40% aqueous PEG 400 receiver fluid

| Compound | 30 h skin conc (μmol/g) | 30 h cumulative amt (nmol) | Flux (nmol/cm$^2$/h) | Flux enhancement | Lag time (h) |
|---|---|---|---|---|---|
| ALL00143 | 5.8 ± 3.0 | ND | ND | | — |
| CBD from ALL00143 | 0.5 ± 0.0 | ND | ND | | — |

*total CBD = total cannabidiol equivalents delivered in the form of cannabidiol and/or prodrug Wherein "n" equals the number of skin samples tested.

TABLE 18

Permeation data of CBD (n = 3), ALL00105 (n = 1) ALL00145 (n = 3), and ALL00147 (n = 2) in 90:8:2 PG:H2O:IPM donor solution with 40% aqueous PEG 400 receiver fluid

| Compound | 30 h skin conc (μmol/g) | 30 h cumulative amt (nmol) | Flux (nmol/cm$^2$/h) | Flux enhancement | Lag time (h) |
|---|---|---|---|---|---|
| cannabidiol (CBD) | 21.2 ± 4.8 | 148.6 ± 54.0 | 8.2 ± 2.6 | — | 11.0 ± 1.2 |
| total cannabidiol* | 70.2 ± 0.0 | 22.3 ± 0.0 | 1.6 ± 0.0 | 0.19 | 15.2 ± 0.0 |
| ALL00105 | ND | — | — | | — |
| ALL00148 from ALL00105 | 40.2 ± 0.0 | 15.4 ± 0.0 | 1.0 ± 0.0 | | 13.0 ± 0.0 |
| CBD from ALL001105 | 30.0 ± 0.0 | 6.9 ± 0.0 | 0.6 ± 0.0 | | 18.6 ± 0.0 |
| total cannabidiol* | 36.1 ± 28.2 | 34.7 ± 7.0 | 2.9 ± 0.7 | 0.35 | 17.2 ± 2.5 |
| ALL00145 | 3.8 ± 2.1 | — | — | | — |
| ALL00146 from ALL00145 | 23.5 ± 19.3 | 17.5 ± 6.1 | 1.5 ± 0.6 | | 19.0 ± 1.9 |
| CBD from ALL00145 | 8.8 ± 7.0 | 17.2 ± 4.5 | 1.4 ± 0.1 | | 17.4 ± 3.3 |
| total cannabidiol* | 17.3 ± 12.6 | 29.0 ± 3.4 | 1.9 ± 0.8 | 0.24 | 13.3 ± 5.0 |
| ALL00147 | 6.3 ± 5.6 | 11.7 ± 3.8 | 0.7 ± 0.01 | | 13.0 ± 5.9 |
| ALL00149 from ALL00147 | 7.1 ± 6.3 | 9.1 ± 0.2 | 0.6 ± 0.2 | | 11.8 ± 5.9 |
| CBD from ALL00147 | 3.9 ± 0.8 | 8.2 ± 7.0 | 0.7 ± 0.6 | | 16.7 ± 0.7 |

*total CBD = total cannabidiol equivalents delivered in the form of cannabidiol and/or prodrug Wherein "n" equals the number of skin samples tested.

TABLE 19

Permeation data of CBD (n = 2), ALL00101 (n = 2) ALL00146 (n = 2), and ALL00148 (n = 3) in gel formulation with 40% aqueous PEG 400 receiver fluid

| Compound | 24 h skin conc (μmol/g) | 24 h cumulative amt (nmol) | Flux (nmol/cm$^2$/h) | Flux enhancement | Lag time (h) |
|---|---|---|---|---|---|
| cannabidiol (CBD) | 9.0 ± 2.2 | 12.3 ± 8.1 | 0.8 ± 0.4 | — | 8.5 ± 2.1 |
| total cannabidiol* | 48.7 ± 38.6 | 8.4 ± 1.3 | 0.4 ± 0.03 | 0.52 | 2.9 ± 1.9 |
| ALL00101 | 0.8 ± 0.6 | ND | — | | — |
| ALL00150 from ALL00101 | 34.7 ± 27.7 | 8.4 ± 1.3 | 0.4 ± 0.03 | | 2.9 ± 1.9 |
| CBD from ALL00101 | 13.2 ± 10.4 | ND | — | | — |
| total cannabidiol* | 4.1 ± 0.4 | 12.7 ± 2.3 | 0.9 ± 0.1 | 1.09 | 8.9 ± 1.1 |
| ALL00146 | 3.3 ± 0.5 | 4.0 ± 0.0 | 0.3 ± 0.0 | | 7.0 ± 0.0 |
| CBD from ALL00146 | 0.8 ± 0.1 | 10.7 ± 0.5 | 0.8 ± 0.1 | | 9.1 ± 0.9 |
| total cannabidiol* | 23.2 ± 23.2 | 8.0 ± 1.8 | 0.5 ± 0.1 | 0.63 | 7.6 ± 2.1 |
| ALL00148 | 20.8 ± 21.1 | 8.0 ± 1.8 | 0.5 ± 0.1 | | 7.6 ± 2.1 |
| CBD from ALL00148 | 2.4 ± 2.1 | ND | — | | — |

*total CBD = total cannabidiol equivalents delivered in the form of cannabidiol and/or prodrug Wherein "n" equals the number of skin samples tested.

TABLE 20

Plasma stability of cannabidiol prodrugs

| | % Prodrug at time (h) | | | | | | | | | |
|---|---|---|---|---|---|---|---|---|---|---|
| | 0 | 0.5 | 1 | 2 | 2.5 | 3 | 4 | 6 | 10 | 20 | 24 |

Mono-prodrug

| | | | | | | | | | | | |
|---|---|---|---|---|---|---|---|---|---|---|---|
| ALL00131 | 100 | — | 64 | 42 | — | — | 24 | 14 | — | — | 14 |
| ALL00140 | 100 | — | — | 0 | — | — | — | — | — | 0 | 0 |
| ALL00137 | 89 | — | 73 | — | — | 60 | — | — | — | — | 4 |

TABLE 20-continued

Plasma stability of cannabidiol prodrugs

% Di-prodrug/% mono-prodrug at time (h)

| | 0 | 1 | | 2 | | 4 | | 6 | | 24 | |
|---|---|---|---|---|---|---|---|---|---|---|---|
| Di-prodrug | | | | | | | | | | | |
| ALL00132 | 100 | 28 | 52 | 15 | 44 | 0 | 24 | 0 | 15 | 0 | 2 |

| | 0 | 1 | | 2 | | 4 | | 20 | | 24 | |
|---|---|---|---|---|---|---|---|---|---|---|---|
| ALL00101 | 100 | 75 | 22 | — | — | — | — | 1 | 11 | — | — |
| ALL00141 | 98 | — | — | 71 | 1 | — | — | 46 | 2 | — | — |

| | 0 | 0.5 | | 2 | | 4 | | 22 | | 24 | |
|---|---|---|---|---|---|---|---|---|---|---|---|
| ALL00105 | 100 | — | — | 92 | 0 | 88 | 0 | 58 | 0 | 55 | 0 |
| ALL00145 | 60:40 | 45 | 44 | — | — | — | — | 37 | 23 | 13 | 11 |
| ALL00147 | 100 | 55 | 0 | 32 | 0 | — | — | 13 | 0 | 12 | 0 |

| | 0 | 1 | | 2 | | 3 | | 6 | | 24 | |
|---|---|---|---|---|---|---|---|---|---|---|---|
| ALL00142 | 100 | 98 | 0 | — | — | 90 | 0 | — | — | 10 | 0 |
| ALL00143 | 100 | 82 | 0 | — | — | 76 | 0 | — | — | 65 | 0 |

TABLE 21

Permeation data of CBD (n = 2), ALL00146 (n = 2), and ALL00150 (n = 3) in gel formulation with 40% aqueous PEG 400 receiver fluid.

| Compound | 24 h skin conc (μmol/g) | 24 h cumulative amt (nmol) | Flux (nmol/cm$^2$/h) | Flux enhancement | Lag time (h) |
|---|---|---|---|---|---|
| cannabidiol (CBD) | 15.6 ± 4.2 | 6.5 ± 3.8 | 0.4 ± 0.2 | — | 5.3 ± 1.7 |
| total cannabidiol* | 19.7 ± 11.9 | 2.7 ± 1.4 | 0.2 ± 0.1 | 0.53 | 9.8 ± 3.7 |
| ALL00146 | 16.0 ± 9.8 | ND | ND | | — |
| CBD from ALL00146 | 3.7 ± 2.1 | 2.7 ± 1.4 | 0.2 ± 0.1 | | 9.8 ± 3.7 |
| total cannabidiol* | 55.6 ± 5.3 | ND | ND | — | — |
| ALL00150 | 47.7 ± 3.0 | ND | ND | | — |
| CBD from ALL00150 | 7.9 ± 2.3 | ND | ND | | — |

*total CBD = total cannabidiol equivalents delivered in the form of cannabidiol and/or prodrug Wherein "n" equals the number of skin samples tested.

TABLE 22

Permeation data of CBD (n = 2) and ALL00150 (n = 3) in an anhydrous gel formulation with 40% aqueous PEG 400 receiver fluid.

| Compound | 24 h skin conc (μmol/g) | 24 h cumulative amt (nmol) | Flux (nmol/cm$^2$/h) | Flux enhancement | Lag time (h) |
|---|---|---|---|---|---|
| cannabidiol (CBD) | 3.3 ± 1.3 | ND | ND | — | — |
| total cannabidiol* | 6.7 ± 3.8 | ND | ND | — | — |
| ALL00150 | 5.6 ± 3.1 | ND | ND | | — |
| CBD from ALL00150 | 1.1 ± 0.8 | ND | ND | | — |

*total CBD = total cannabidiol equivalents delivered in the form of cannabidiol and/or prodrug Wherein "n" equals the number of skin samples tested.

TABLE 23

Permeation data of CBD (n = 1), ALL00146 (n = 1), and ALL00150 (n = 1) in gel formulation with 40% aqueous PEG 400 receiver fluid.

| Compound | 24 h skin conc (μmol/g) | 24 h cumulative amt (nmol) | Flux (nmol/cm$^2$/h) | Flux enhancement | Lag time (h) |
|---|---|---|---|---|---|
| cannabidiol (CBD) | 27.7 ± 24.6 | 3.0 | 0.29 | — | 12.8 |
| total cannabidiol* | 9.5 ± 7.3 | 12.5 | 0.58 | 2.0 | — |

TABLE 23-continued

Permeation data of CBD (n = 1), ALL00146 (n = 1), and ALL00150 (n = 1) in gel formulation with 40% aqueous PEG 400 receiver fluid.

| Compound | 24 h skin conc (μmol/g) | 24 h cumulative amt (nmol) | Flux (nmol/cm$^2$/h) | Flux enhancement | Lag time (h) |
|---|---|---|---|---|---|
| ALL00147 | 0.8 ± 0.7 | 0.9 | — | | — |
| ALL00149 from ALL00147 | 8.7 ± 6.6 | 5.7 | 0.25 | | — |
| CBD from ALL00146 | ND | 5.9 | 0.26 | | 0.4 |
| total cannabidiol* | 46.3 ± 11.8 | 6.9 | 0.40 | 1.4 | 6.2 |
| ALL00149 | 46.0 ± 11.5 | 5.8 | 0.29 | | 6.4 |
| CBD from ALL00149 | 0.9 ± 0.0 | 1.2 | — | | — |

*total CBD = total cannabidiol equivalents delivered in the form of cannabidiol and/or prodrug

TABLE 24

Plasma stability of cannabidiol prodrugs

% Prodrug at time (h)

| Mono-prodrug | 0 | 0.5 | 1 | 2 | 2.5 | 3 | 4 | 6 | 10 | 20 | 24 |
|---|---|---|---|---|---|---|---|---|---|---|---|
| ALL00149 | 100 | 31 | 12 | 0 | — | — | — | — | — | — | — |

% Di-prodrug/% mono-prodrug at time (h)

| Di-prodrug | 0 | 0.5 | 1 | 2 | 6 | 24 |
|---|---|---|---|---|---|---|
| ALL00147 | 97 3 | 0 37 | 0 10 | 0 2 | — | — |

All references, including publications, patent applications, and patents, cited herein are hereby incorporated by reference to the same extent as if each reference were individually and specifically indicated to be incorporated by reference and were set forth in its entirety herein.

The use of the terms "a," "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

We claim:
1. A compound selected from the group consisting of:
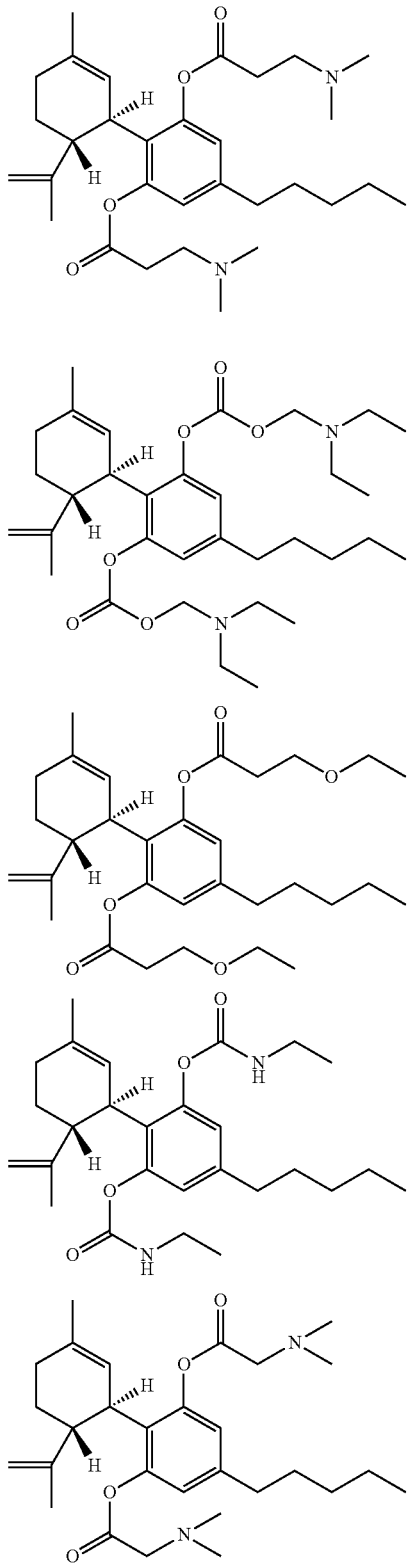
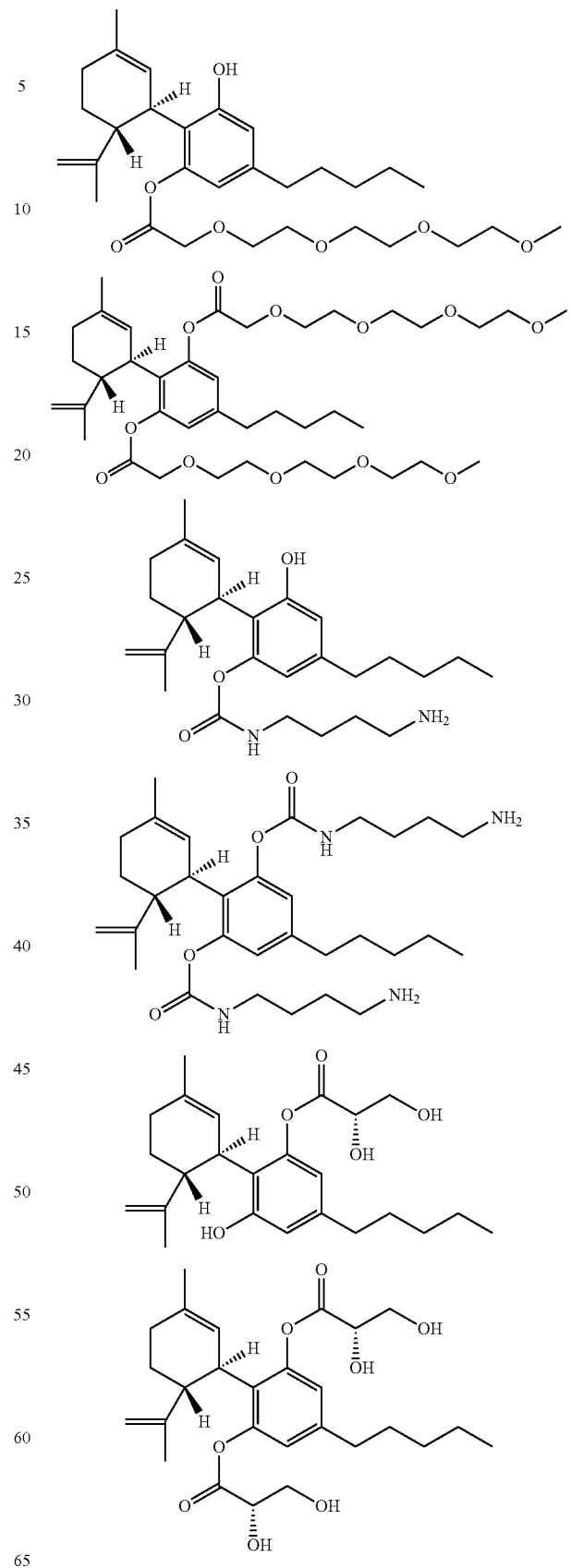

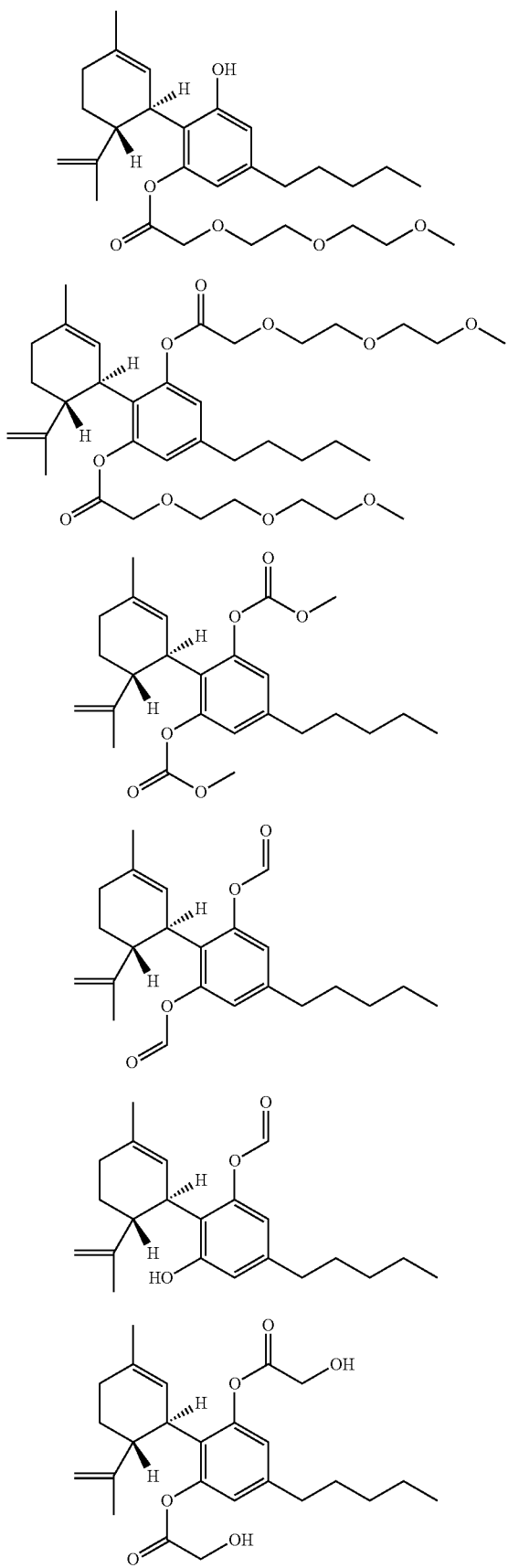

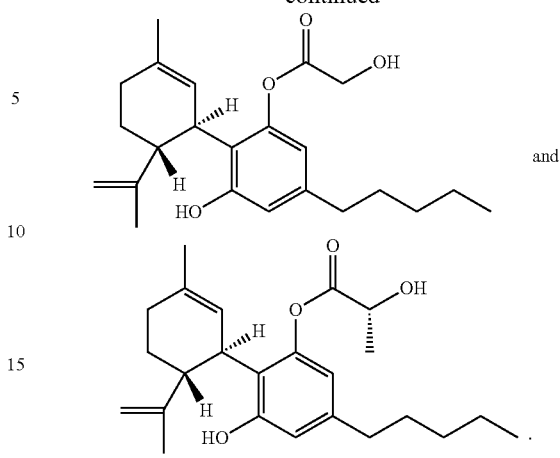

and

2. A pharmaceutical composition comprising:
(a) a compound as described in claim 1; and
(b) a pharmaceutically acceptable excipient.

3. A method of treating a medical condition in a mammal comprising the step of administering a compound as described in claim 1, wherein the medical condition is selected from the group consisting of: nausea, vomiting, emesis, pain, wasting syndrome, HIV-wasting, chemotherapy induced nausea and vomiting, alcohol use disorders, dystonia, multiple sclerosis, inflammatory bowel disorders, arthritis, dermatitis, Rheumatoid arthritis, systemic lupus erythematosus, anti-inflammatory, anti-convulsant, anti-psychotic, anti-oxidant, neuroprotective, anti-cancer, immunomodulatory effects, peripheral neuropathic pain, neuropathic pain associated with post-herpetic neuralgia, diabetic neuropathy, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, ankylosing spondylitis, psoriatic arthritis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, synovitis, juvenile rheumatoid arthritis and inhibition of hair growth.

4. The method of claim 3 wherein the cannabidiol prodrug is administered transdermally.

5. The method of claim 3 wherein the cannabidiol prodrug is administered topically.

6. A method of administering a compound to a mammal comprising the steps of:
(a) combining a compound of claim 1 with a pharmaceutical excipient to form a pharmaceutical composition;
(b) creating a dosage form suitable for administration to a mammal from the pharmaceutical composition; and
(c) administering the dosage form to a mammal.

7. The method of claim 6 wherein the compound is administered by a route selected from the group consisting of: transdermal, topical, oral, buccal, sublingual, intra venous, intra muscular, vaginal, rectal, ocular, nasal and follicular.

8. The compound of claim 1, which is:
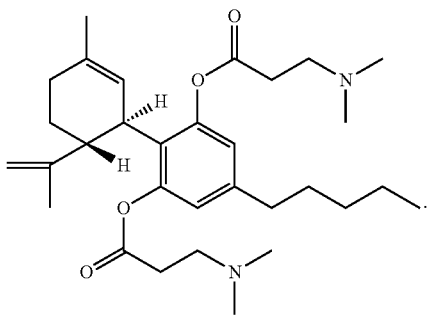
9. The compound of claim 1, which is:
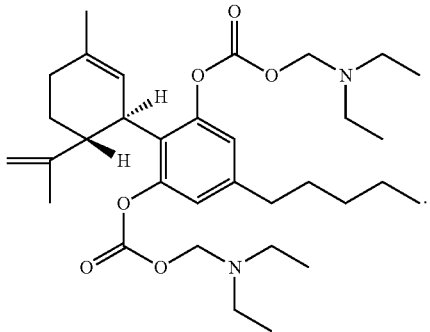
10. The compound of claim 1, which is:
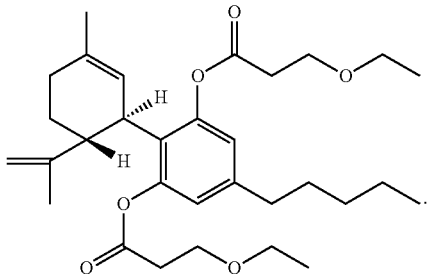
11. The compound of claim 1, which is:
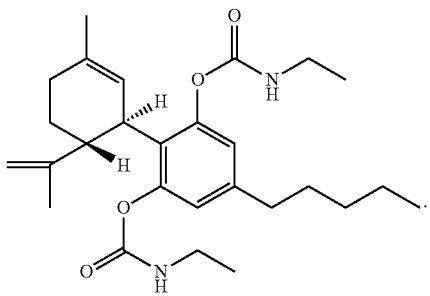
12. The compound of claim 1, which is:
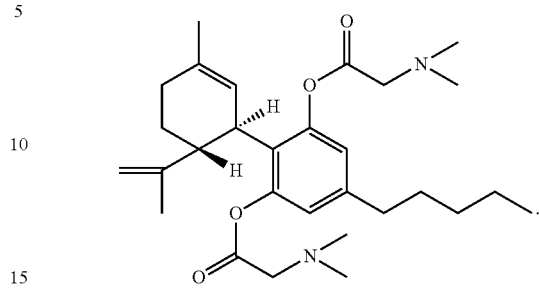
13. The compound of claim 1, which is:
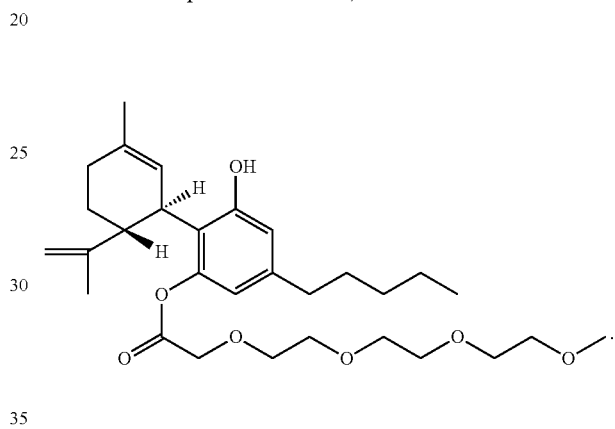
14. The compound of claim 1, which is:
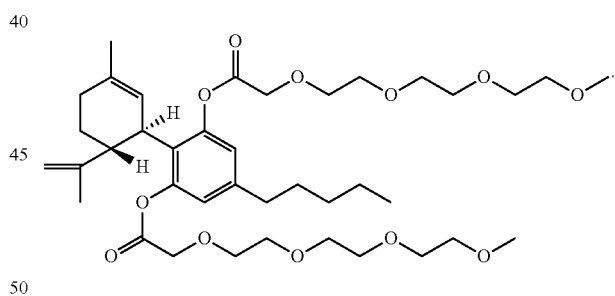
15. The compound of claim 1, which is:
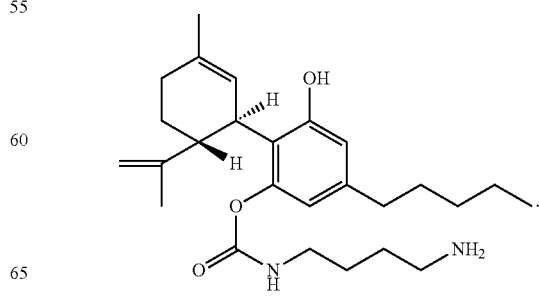

16. The compound of claim 1, which is:
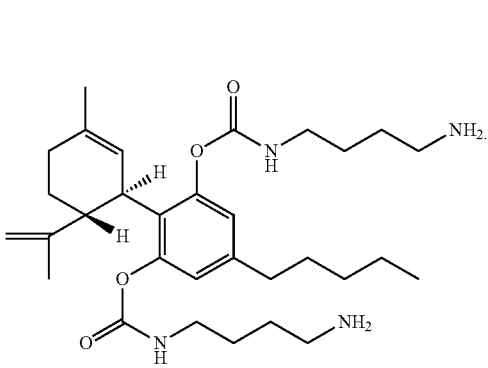
17. The compound of claim 1, which is:
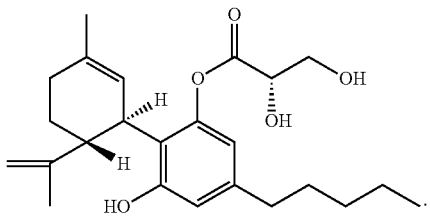
18. The compound of claim 1, which is:
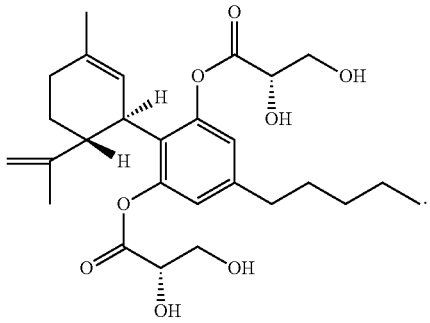
19. The compound of claim 1, which is:
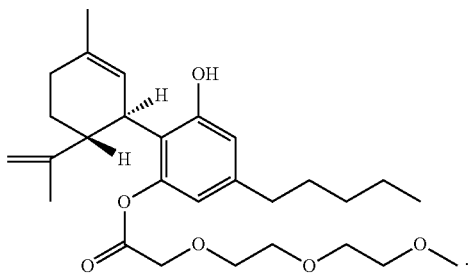
20. The compound of claim 1, which is:
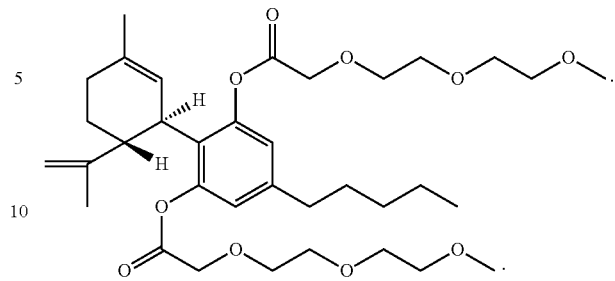
21. The compound of claim 1, which is:
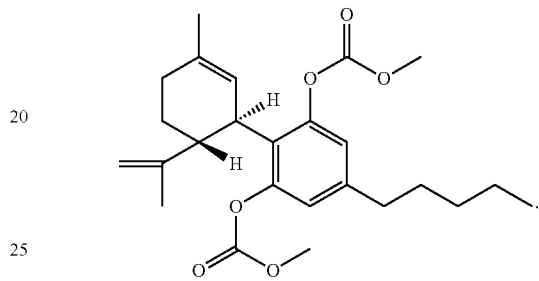
22. The compound of claim 1, which is:
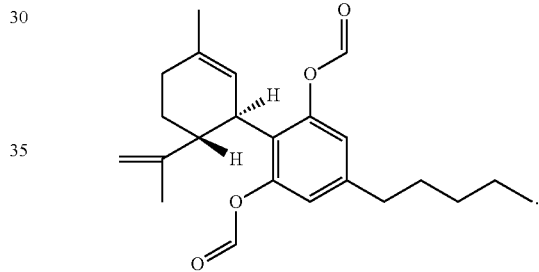
23. The compound of claim 1, which is:
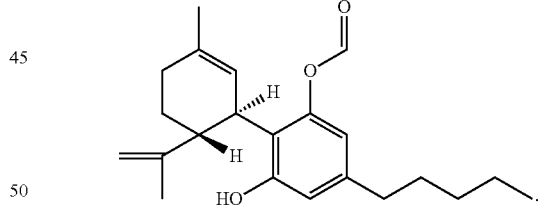
24. The compound of claim 1, which is:
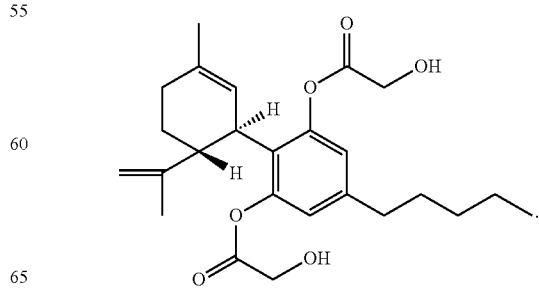

25. The compound of claim 1, which is:
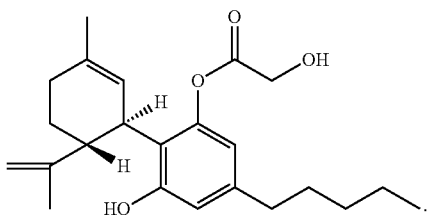
26. The compound of claim 1, which is:
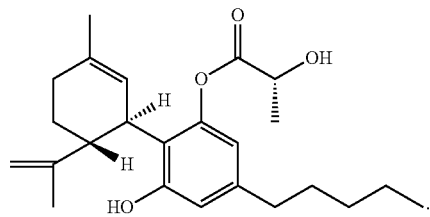
* * * * *